US011180550B2

(12) United States Patent
Powell et al.

(10) Patent No.: US 11,180,550 B2
(45) Date of Patent: *Nov. 23, 2021

(54) COMPOSITIONS AND METHODS FOR TREATING CANCER

(71) Applicants: The Trustees of the University of Pennsylvania, Philadelphia, PA (US); Fondazione IRCCS Istituto Nazionale dei Tumori, Milan (IT)

(72) Inventors: Daniel J. Powell, Bala Cynwyd, PA (US); George Coukos, Wynnewood, PA (US); Mariangela Figini, Milan (IT); Silvana Canevari, Milan (IT)

(73) Assignees: The Trustees of the University of Pennsylvania, Philadelphia, PA (US); Fondazione IRCCS Istituto Nazionale dei Tumori, Milan (IT)

( * ) Notice: Subject to any disclaimer, the term of this patent is extended or adjusted under 35 U.S.C. 154(b) by 22 days.

This patent is subject to a terminal disclaimer.

(21) Appl. No.: 16/594,871

(22) Filed: Oct. 7, 2019

(65) Prior Publication Data

US 2020/0270341 A1    Aug. 27, 2020

Related U.S. Application Data

(63) Continuation of application No. 15/212,916, filed on Jul. 18, 2016, now Pat. No. 10,457,729, which is a continuation of application No. 13/979,927, filed as application No. PCT/US2012/021738 on Jan. 18, 2012, now Pat. No. 9,402,865.

(60) Provisional application No. 61/433,731, filed on Jan. 18, 2011.

(51) Int. Cl.
| | |
|---|---|
| *C07K 16/28* | (2006.01) |
| *A61K 39/00* | (2006.01) |
| *A61K 39/395* | (2006.01) |
| *C07K 14/705* | (2006.01) |
| *A61K 35/17* | (2015.01) |
| *C07K 14/725* | (2006.01) |
| *A61K 35/12* | (2015.01) |

(52) U.S. Cl.
CPC .............. *C07K 16/28* (2013.01); *A61K 35/17* (2013.01); *A61K 39/0011* (2013.01); *A61K 39/39558* (2013.01); *C07K 14/705* (2013.01); *C07K 14/7051* (2013.01); *C07K 14/70517* (2013.01); *C07K 14/70578* (2013.01); *A61K 2035/124* (2013.01); *A61K 2039/505* (2013.01); *A61K 2039/5156* (2013.01); *A61K 2039/5158* (2013.01); *C07K 2317/622* (2013.01); *C07K 2318/20* (2013.01); *C07K 2319/02* (2013.01); *C07K 2319/03* (2013.01); *C07K 2319/30* (2013.01); *C07K 2319/74* (2013.01)

(58) Field of Classification Search
CPC ...................................................... C07K 16/28
See application file for complete search history.

(56) References Cited

U.S. PATENT DOCUMENTS

| | | |
|---|---|---|
| 5,199,942 A | 4/1993 | Gillis et al. |
| 5,326,193 A | 7/1994 | Peterson |
| 5,350,674 A | 9/1994 | Boenisch et al. |
| 5,399,346 A | 3/1995 | Anderson et al. |
| 5,580,849 A | 12/1996 | Dyet et al. |
| 5,585,362 A | 12/1996 | Wilson et al. |
| 5,589,466 A | 12/1996 | Felgner et al. |
| 5,858,358 A | 1/1999 | June et al. |
| 5,883,223 A | 3/1999 | Gray |
| 6,120,766 A | 9/2000 | Hale et al. |
| 6,352,694 B1 | 3/2002 | June et al. |
| 6,534,055 B1 | 3/2003 | June et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 8,399,645 B2 | 3/2013 | Campana et al. |
| 9,402,865 B2 * | 8/2016 | Powell ............... C07K 14/7051 |
| 10,457,729 B2 * | 10/2019 | Powell .................. A61K 35/17 |
| 2002/0168719 A1 | 11/2002 | Kwon |

(Continued)

FOREIGN PATENT DOCUMENTS

| | | |
|---|---|---|
| WO | 0129058 A1 | 4/2001 |
| WO | 0196584 A2 | 12/2001 |

(Continued)

OTHER PUBLICATIONS

Canadian Patent Application No. 2,824,997—Office Action dated Jan. 28, 2019.
Chinese Patent Application No. 201280013888.1—first Office Action dated Aug. 20, 2014.
Chinese Patent Application No. 201280013888.1—third Office Action dated Nov. 18, 2015.

(Continued)

*Primary Examiner* — Scott Long
(74) *Attorney, Agent, or Firm* — Saul Ewing Arnstein & Lehr LLP; Kathryn Doyle

(57) ABSTRACT

The invention provides compositions and methods for treating ovarian cancer. Specifically, the invention relates to administering a genetically modified T cell having α-folate receptor (FRα) binding domain and 4-1BB (CD137) costimulatory domain to treat ovarian cancer.

22 Claims, 38 Drawing Sheets

Specification includes a Sequence Listing.

(56) References Cited

U.S. PATENT DOCUMENTS

| | | |
|---|---|---|
| 2003/0082157 A1 | 5/2003 | Kwon et al. |
| 2004/0043401 A1 | 3/2004 | Sadelain et al. |
| 2004/0091476 A1 | 5/2004 | Kwon |
| 2004/0101519 A1 | 5/2004 | June et al. |
| 2004/0235108 A1 | 11/2004 | Grasso et al. |
| 2005/0113564 A1 | 5/2005 | Campana et al. |
| 2005/0232919 A1 | 10/2005 | Grasso et al. |
| 2006/0002904 A9 | 1/2006 | Kwon |
| 2006/0029595 A1 | 2/2006 | Kwon |
| 2006/0034810 A1 | 2/2006 | Riley et al. |
| 2006/0063923 A1 | 3/2006 | Kwon |
| 2006/0121005 A1 | 6/2006 | Berenson et al. |
| 2006/0239910 A1 | 10/2006 | Nicolaides et al. |
| 2009/0274697 A1 | 11/2009 | Grasso et al. |
| 2009/0324594 A1 | 12/2009 | Nicolaides et al. |
| 2010/0055034 A1 | 3/2010 | Martin et al. |
| 2012/0282256 A1 | 11/2012 | Campana et al. |
| 2013/0216509 A1 | 8/2013 | Campana et al. |
| 2013/0266551 A1 | 10/2013 | Campana et al. |

FOREIGN PATENT DOCUMENTS

| | | |
|---|---|---|
| WO | 0233101 A1 | 4/2002 |
| WO | 02072850 A1 | 9/2002 |
| WO | 2005044996 A2 | 5/2005 |
| WO | 2010025177 A1 | 3/2010 |

OTHER PUBLICATIONS

Eurasian Patent Application No. 201391059/28—Office Action dated Dec. 16, 2016.
European Patent Application No. 12736801.7—European Search Report dated Jul. 31, 2014.
Indian Patent Application No. 6337/DELNP/2013—Office Action dated Aug. 23, 2018.
Japanese Patent Application No. 2013-550567—Office Action dated Dec. 3, 2015.
PCT/US2012/21738—International Search Report dated Jul. 13, 2012.
Singapore Patent Application No. 2013054689—Search Report and Written Opinion dated Oct. 10, 2014.
Singapore Patent Application No. 2013054689—Search Report and Written Opinion dated Sep. 18, 2014.
Berge, et al., "Selective Expansion of a Peripheral Blood CD8+ Memory T Cell Subset Expressing Both Granzyme B and L-Selectin During Primary Viral Infection in Renal Allograft Recipients.", Transplant Proc. 30(8):3975-3977, 1998.
Berger, et al., "Nonmyeloablative Immunosuppressive Regimen Prolongs In Vivo Persistence of Gene-Modified Autologous T Cells in Nonhuman Primate Model", 2001, J Virol 75(2):799-808.
Bierer, et al., "Cyclosporin A and FK506: molecular mechanisms of immunosuppression and probes for transplantation biology", Curr. Opin. Immun. 5:763-773, 1993.
Bird, et al., "Single-chain antigen-binding proteins", 1988, Science 242:423-426.
Canevari, et al., "Anti-ovarian carcinoma anti-T3 heteroconjugates or hybrid antibodies induce tumor cell lysis by cytotoxic T-cells.", Int J. Cancer Suppl 1988;2:18-21 (Abstract).
Canevari, et al., "Regression of advanced ovarian carcinoma by intraperitoneal treatment with autologous T lymphocytes retargeted by a bispecific monoclonal antibody.", 1995, J Natl Cancer Inst 87(19):1463-9 (Abstract).
Carpenito, et al., "Control of large, established tumor xenografts with genetically retargeted human T cells containing CD28 and CD137 domains.", 2009, PNAS 106(9):3360-3365.
Craddock, et al., "Enhanced Tumor Trafficking of GD2 Chimeric Antigen Receptor T Cells by Expression of Chemokine Receptor CCR2b.", 2010, J Immunother 33(8):780-788.
Dotti, et al., "Fifteen Years of Gene Therapy Based on Chimeric Antigen Receptors: 'Are We Nearly There Yet'", 2009, Human Gene Therapy 20:1229-1239.

Dudley, et al., "Cancer regression and autoimmunity in patients after clonal repopulation with antitumor lymphocytes", Science. 298(5594), Oct. 25, 2002, 850-854.
Dull, et al., "A third-generation lentivirus vector with a conditional packaging system.", 1998, J Virol 72 (11):8463-8471.
Duong, et al., "Enhancing the specificity of T-cell cultures for adoptive immunotherapy of cancer.", Immunotherapy. 3(1):33-48 (2011).
Figini, et al., "Conversion of murine antibodies to human antibodies and their optimization for ovarian cancer therapy targeted to the folate receptor.", 2009, Cancer Immunol Immunother 58(4):531-46 (Abstract).
Figini, et al., "Panning phage antibody libraries on cells: isolation of human Fab fragments against ovarian carcinoma using guided selection.", 1998. Cancer Res. 991-996.
Garland, et al., "The use of Teflon cell culture bags to expand functionally active CD8+ cytotoxic T lymphocytes.", J. Immunol Meth. 227(1-2):53-63, 1999.
Ghosh, et al., "Design of liposomes for circumventing the reticuloendothelial cells", 1991 Glycobiology 5: 505-10.
Gross, et al., "'Expression of immunoglobulin-T-cell receptor chimeric molecules as functional receptors with antibody-type specificity.'", Proc. Natl. Acad. Sci. U.S.A. 86:, 1989, 10024-10028.
Haanen, et al., "Selective Expansion of Cross-reacitve CD8+ Memory T Cells by Viral Variants.", J. Exp. Med. 190 (9):13191328, 1999.
Henderson, et al., "Comparison of the effects of FK-506, cyclosporin A and rapamycin on IL-2 production", Immun. 73:316-321, 1991.
Hodi, et al., "Improved Survival with Ipilimumab in Patients with Metastatic Melanoma.", 2010, N Engl J Med 363 (8):711-723 (Aug. 19, 2010).
Hombach, et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule.", J Immunol 2001; 167(11):6123-6131.
Hoos, et al., "Improved Endpoints for Cancer Immunotherapy Trials.", J Natl Cancer Inst 2010; 102:1388-1397.
Huston, et al., "Protein engineering of antibody binding sites: Recovery of sepcific activity in an anti-digoxin single-chain Fv analogue produced in *Escherichia coli*.", 1988, Proc Natl Acad Sci USA 85:5879-5883.
Hwu, et al., "Lysis of ovarian cancer cells by human lymphocytes redirected with a chimeric gene composed of an antibody variable region and the Fc receptor gamma chain.", J Exp Med. Jul. 1, 1993;178(1):361-6.
Jackaman, et al., "IL-2 intratumoral immunotherapy engances CD8+ T cells that mediate destruction of tumor cells and tumor-associated vasculature: a novel mechanism for IL-2.", J Immunol 171:5051-63 (2003).
Johnson, et al., "Gene therapy with human and mouse T-cell receptors mediates cancer regression and targets normal tissues expressing cognate antigen.", 2009, Blood 114: 535-546.
Johnson, et al., "Gene Transfer of Tumor-Reactive TCR Confers Both High Avidity and Tumor Reactivity to Nonreactive Peripheral Blood Mononuclear Cells and Tumor-Infiltrating Lymphocytes1", J. Immunol. 177(9), 2006, 6548-6559.
Kershaw, et al., "A Phase I Study on Adoptive Immunotherapy Using Gene-Modified T Cells for Ovarian Cancer", Clin Cancer Res. Oct. 15, 2006; 12(20 Pt 1): 6106-6115.
King, et al., "Human peripheral blood leucocyte non-obese diabetic-severe combined immunodeficiency interleukin-2 receptor gamma chain gene mouse model of xenogeneic graft-versus-host-like disease and the role of host major histocompatibility complex.", 2009, Clin Exp Immunol 157:104-118.
Kochenderfer, et al., "Eradication of B-lineage cells and regression of lymphoma in a patient treated with autologous T cells genetically engineered to recognize CD19.", 2010, Blood 116:4099-4102.
Lamers, et al., "Immune responses to transgene and retroviral vector in patients treated with ex vivo-engineered T cells", 2011, Blood, 117: 72-82.

(56) References Cited

OTHER PUBLICATIONS

Lee, et al., "Molecular cloning of agonistic and antagonistic monoclonal antibodies agains human 4-1BB.", 2002, Eur J Immunogenet 29(5):449-52 (Abstract).
Levine, et al., "Effects of CD28 costimulation on long-term proliferation of CD4+ T cells in the absence of exogenous feeder cells", 1997. J. Immunology. 5921-30.
Levine, et al., "Gene transfer in humans using a conditionally replicating lentiviral vector.", 2006, PNAS 103 (46):17372-17377.
Liu, et al., "Calcineurin is a common target of cyclophilin-cyclosporin A and FKBP-FK506 complexes", Cell 66:807-815, 1991.
Low, "Folate receptor-targeted drugs for cancer and inflammatory diseases.", 2004, Advanced Drug Delivery Reviews 56:1055-1058.
Melani, et al., "Targeting of Interleukin 2 to Human Ovarian Carcinoma by Fusion with a Single-Chain Fv of Antifolate Recptor Antibody.", 1998, Cancer Res 58:4146-4154.
Milone, et al., "Chimeric Receptors Containing C137 Signal Transduction Domains Mediate Enhanced Survival of T Cells and Increased Antileukemic Efficacy In Vivo.", 2009, Mol Ther 17:1453-1464.
Miotti, et al., "Characterization of Human Ovarian Cardinoma-Associated Antigens Defined by Novel Monoclonal Antibodies with Tumor-Restricted Specificity.", 1987, Int J Cancer 39:297-303.
Montini, et al., "Hematopoietic stem cell gene transfer in a tumor-prone mouse model uncovers low genotoxicity of lentiviral vector integration.", 2006, Nature Biotechnology 24(6):687-696.

\* cited by examiner

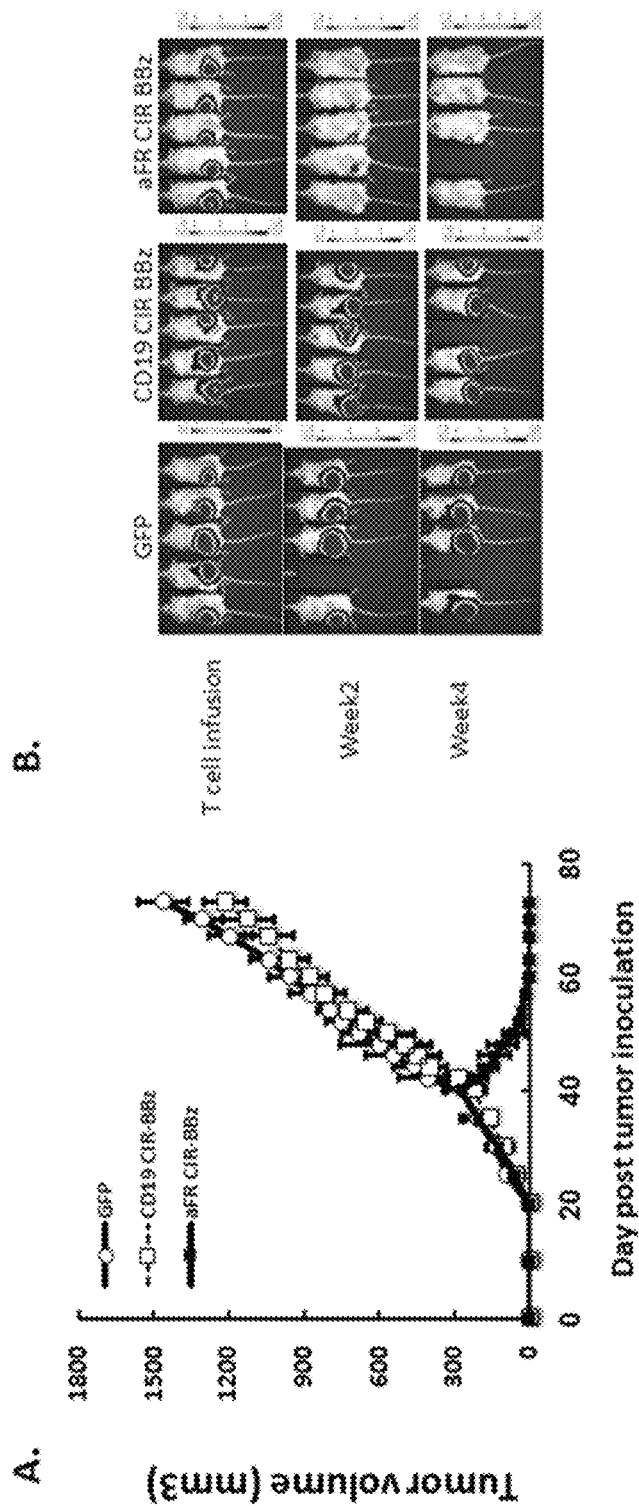
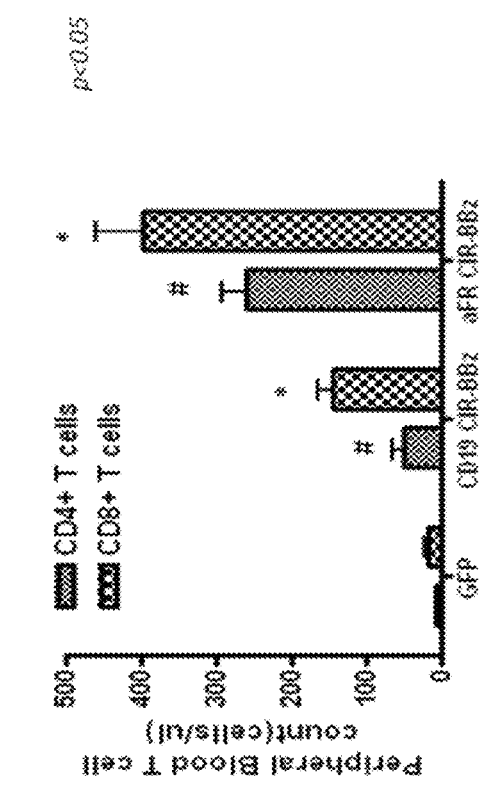
Figures 14A-14C

| | |
|---|---|
| SEQ ID NO: 1 | MOv19-4-1BB-CD3zeta CAR – DNA |
| SEQ ID NO: 2 | CD8α leader – DNA |
| SEQ ID NO: 3 | MOv19 scFv – DNA [FRα binding domain] |
| SEQ ID NO: 4 | CD8α hinge – DNA |
| SEQ ID NO: 5 | CD8α transmembrane – DNA |
| SEQ ID NO: 6 | 4-1BB Intracellular domain – DNA |
| SEQ ID NO: 7 | CD3 zeta intracellular domain – DNA |
| SEQ ID NO: 8 | LTR R & U5 regions |
| SEQ ID NO: 9 | RSV Promoter |
| SEQ ID NO: 10 | Partial gag |
| SEQ ID NO: 11 | cPPT |
| SEQ ID NO: 12 | EF1-α Promoter |
| SEQ ID NO: 13 | MOv19-4-1BB-CD3zeta CAR amino acid |
| SEQ ID NO: 14 | CD8α leader – amino acid |
| SEQ ID NO: 15 | MOv19 scFv – amino acid [FRα binding domain] |
| SEQ ID NO: 16 | CD8α hinge – amino acid |
| SEQ ID NO: 17 | CD8α transmembrane – amino acid |
| SEQ ID NO: 18 | 4-1BB Intracellular domain – amino acid |
| SEQ ID NO: 19 | CD3 zeta intracellular domain – amino acid |
| SEQ ID NO: 20 | C4 scFv-4-1BB-CD3zeta CAR – DNA |
| SEQ ID NO: 21 | C4 scFv – DNA [FRα binding domain] |
| SEQ ID NO: 22 | C4 scFv-4-1BB-CD3zeta CAR – amino acid |
| SEQ ID NO: 23 | C4 scFv – amino acid [FRα binding domain] |

Figure 30

SEQUENCE LISTING

<160> NUMBER OF SEQ ID NOS: 29

<210> SEQ ID NO 1
<211> LENGTH: 9228
<212> TYPE: DNA
<213> ORGANISM: Artificial Sequence
<220> FEATURE:
<223> OTHER INFORMATION: Chemically Synthesized

<400> SEQUENCE: 1

| | | | | | |
|---|---|---|---|---|---|
| atggccttac | cagtgaccgc | cttgctcctg | ccgctggcct | tgctgctcca | cgccgccagg | 60 |
| ccgggatcct | ctagagcggc | ccagccggcc | atggcccagg | tgcagctgca | gcagtctgga | 120 |
| gctgagctgg | tgaagcctgg | ggcttcagtg | aagatatcct | gcaaggcttc | tggttactca | 180 |
| tttactggct | actttatgaa | ctgggtgaag | cagagccatg | gaaagagcct | tgagtggatt | 240 |
| ggacgtattc | atccttacga | tggtgatact | ttctacaacc | agaacttcaa | ggacaaggcc | 300 |
| acattgactg | tagacaaatc | ctctaacaca | gcccacatgg | agctcctgag | cctgacatct | 360 |
| gaggactttg | cagtctatta | ttgtacaaga | tacgacggta | gtcgggctat | ggactactgg | 420 |
| ggccaaggga | ccacggtcac | cgtctcctca | ggtggaggcg | gttcaggcgg | aggtggctct | 480 |
| ggcggtggcg | gatcggacat | cgagctcact | cagtctccag | cttctttggc | tgtgtctcta | 540 |
| gggcagaggg | ccatcatctc | ctgcaaggcc | agccaaagtg | tcagttttgc | tggtactagt | 600 |
| ttaatgcact | ggtaccacca | gaaaccagga | cagcaaccca | aactcctcat | ctatcgtgca | 660 |
| tccaacctag | aagctggggt | tcctaccagg | tttagtggca | gtgggtctaa | gacagacttc | 720 |
| accctcaata | tccatcctgt | ggaggaggag | gatgctgcaa | cctattactg | tcagcaaagt | 780 |
| agggaatatc | cgtacacgtt | cggaggggg | acaaagttgg | aaataaaacg | ggcggccgct | 840 |
| agcaccacga | cgccagcgcc | gcgaccacca | acaccggcgc | ccaccatcgc | gtcgcagccc | 900 |
| ctgtccctgc | gcccagaggc | gtgccggcca | gcggcggggg | gcgcagtgca | cacgaggggg | 960 |
| ctggacttcg | cctgtgatat | ctacatctgg | gcgcccttgg | ccgggacttg | tggggtcctt | 1020 |
| ctcctgtcac | tggttatcac | cctttactgc | aaacggggca | gaaagaaact | cctgtatata | 1080 |
| ttcaaacaac | catttatgag | accagtacaa | actactcaag | aggaagatgg | ctgtagctgc | 1140 |
| cgatttccag | aagaagaaga | aggaggatgt | gaactgagag | tgaagttcag | caggagcgca | 1200 |
| gacgcccccg | cgtacaagca | gggccagaac | cagctctata | cgagctcaa | tctaggacga | 1260 |
| agagaggagt | acgatgtttt | ggacaagaga | cgtggccggg | accctgagat | ggggggaaag | 1320 |
| ccgagaagga | agaaccctca | ggaaggcctg | tacaatgaac | tgcagaaaga | taagatggcg | 1380 |
| gaggcctaca | gtgagattgg | gatgaaaggc | gagcgccgga | ggggcaaggg | gcacgatggc | 1440 |
| ctttaccagg | gtctcagtac | agccaccaag | gacacctacg | acgcccttca | catgcaggcc | 1500 |
| ctgcccctc | gctaagtcga | ctcgacaatc | aacctctgga | ttacaaaatt | tgtgaaagat | 1560 |
| tgactggtat | tcttaactat | gttgctcctt | ttacgctatg | tggatacgct | gctttaatgc | 1620 |
| ctttgtatca | tgctattgct | tcccgtatgg | ctttcatttt | ctcctccttg | tataaatcct | 1680 |
| ggttgctgtc | tctttatgag | gagttgtggc | ccgttgtcag | gcaacgtggc | gtggtgtgca | 1740 |
| ctgtgtttgc | tgacgcaacc | cccactggtt | ggggcattgc | caccacctgt | cagctccttt | 1800 |
| ccgggacttt | cgctttcccc | ctccctattg | ccacggcgga | actcatcgcc | gcctgccttg | 1860 |
| cccgctgctg | gacaggggct | cggctgttgg | gcactgacaa | ttccgtggtg | ttgtcgggga | 1920 |
| agctgacgtc | ctttccatgg | ctgctcgcct | gtgttgccac | ctggattctg | cgcgggacgt | 1980 |
| ccttctgcta | cgtcccttcg | gccctcaatc | cagcggacct | tccttcccgc | ggcctgctgc | 2040 |

```
cggctctgcg gcctcttccg cgtcttcgcc ttcgccctca gacgagtcgg atctcccttt    2100
gggccgcctc cccgcctgga attcgagctc ggtaccttta agaccaatga cttacaaggc    2160
agctgtagat cttagccact ttttaaaaga aagggggga ctggaagggc taattcactc     2220
ccaacgaaga caagatctgc ttttttgcttg tactgggtct ctctggttag accagatctg   2280
agcctgggag ctctctggct aactagggaa cccactgctt aagcctcaat aaagcttgcc    2340
ttgagtgctt caagtagtgt gtgcccgtct gttgtgtgac tctggtaact agagatccct    2400
cagacccttt tagtcagtgt ggaaaatctc tagcagtagt agttcatgtc atcttattat    2460
tcagtattta taacttgcaa agaaatgaat atcagagagt gagaggaact gtttattgc     2520 agcttataat ggttacaaat aaagcaatag catcacaaat ttcacaaata aagcattttt    2580
ttcactgcat tctagttgtg gtttgtccaa actcatcaat gtatcttatc atgtctggct    2640
ctagctatcc cgcccctaac tccgcccagt tccgcccatt ctccgcccca tggctgacta    2700 attttttta tttatgcaga ggccgaggcc gcctcggcct ctgagctatt ccagaagtag     2760
tgaggaggct ttttggagg cctaggcttt tgcgtcgaga cgtacccaat tcgccctata     2820
gtgagtcgta ttacgcgcgc tcactggccg tcgttttaca acgtcgtgac tgggaaaacc    2880
ctggcgttac ccaacttaat cgccttgcag cacatccccc tttcgccagc tggcgtaata    2940
gcgaagaggc ccgcaccgat cgcccttccc aacagttgcg cagcctgaat ggcgaatggc    3000
gcgacgcgcc ctgtagcggc gcattaagcg cggcgggtgt ggtggttacg cgcagcgtga    3060
ccgctacact tgccagcgcc ctagcgcccg ctcctttcgc tttcttccct tcctttctcg    3120
ccacgttcgc cggctttccc cgtcaagctc taaatcgggg gctcccttta gggttccgat    3180
ttagtgcttt acggcacctc gaccccaaaa aacttgatta gggtgatggt tcacgtagtg    3240
ggccatcgcc ctgatagacg gttttcgcc ctttgacgtt ggagtccacg ttctttaata    3300
gtggactctt gttccaaact ggaacaacac tcaaccctat ctcggtctat tcttttgatt    3360
tataagggat tttgccgatt tcggcctatt ggttaaaaaa tgagctgatt taacaaaaat    3420
ttaacgcgaa ttttaacaaa atattaacgt ttacaatttc ccaggtggca cttttcgggg    3480
aaatgtgcgc ggaacccta tttgtttatt tttctaaata cattcaaata tgtatccgct    3540
catgagacaa taaccctgat aaatgcttca ataatattga aaaggaaga gtatgagtat    3600 tcaacatttc cgtgtcgccc ttattccctt ttttgcggca ttttgccttc ctgttttgc    3660 tcacccagaa acgctggtga agtaaaaga tgctgaagat cagttgggtg cacgagtggg    3720
ttacatcgaa ctggatctca acagcggtaa gatccttgag agttttcgcc ccgaagaacg    3780
ttttccaatg atgagcactt ttaaagttct gctatgtggc gcggtattat cccgtattga    3840
cgccgggcaa gagcaactcg gtcgccgcat acactattct cagaatgact tggttgagta    3900
ctcaccagtc acagaaaagc atcttacgga tggcatgaca gtaagagaat tatgcagtgc    3960
tgccataacc atgagtgata acactgcggc caacttactt ctgacaacga tcggaggacc    4020
gaaggagcta accgcttttt tgcacaacat gggggatcat gtaactcgcc ttgatcgttg    4080
ggaaccggag ctgaatgaag ccataccaaa cgacgagcgt gacaccacga tgcctgtagc    4140
aatggcaaca acgttgcgca aactattaac tggcgaacta cttactctag cttcccggca    4200
acaattaata gactggatgg aggcggataa agttgcagga ccacttctgc gctcggccct    4260
tccggctggc tggtttattg ctgataaatc tggagccggt gagcgtgggt ctcgcggtat    4320
cattgcagca ctggggccag atggtaagcc ctcccgtatc gtagttatct acacgacggg    4380
```

```
gagtcaggca actatggatg aacgaaatag acagatcgct gagataggtg cctcactgat    4440
taagcattgg taactgtcag accaagttta ctcatatata ctttagattg atttaaaact    4500
tcatttttaa tttaaaagga tctaggtgaa gatccttttt gataatctca tgaccaaaat    4560
cccttaacgt gagttttcgt tccactgagc gtcagacccc gtagaaaaga tcaaaggatc    4620
ttcttgagat cctttttttc tgcgcgtaat ctgctgcttg caaacaaaaa aaccaccgct    4680
accagcggtg gtttgtttgc cggatcaaga gctaccaact cttttccga aggtaactgg    4740 cttcagcaga gcgcagatac caaatactgt ccttctagtg tagccgtagt taggccacca    4800
cttcaagaac tctgtagcac cgcctacata cctcgctctg ctaatcctgt taccagtggc    4860
tgctgccagt ggcgataagt cgtgtcttac cgggttggac tcaagacgat agttaccgga    4920
taaggcgcag cggtcgggct gaacggggg ttcgtgcaca cagcccagct tggagcgaac    4980
gacctacacc gaactgagat acctacagcg tgagctatga gaaagcgcca cgcttcccga    5040
agggagaaag gcggacaggt atccggtaag cggcagggtc ggaacaggag agcgcacgag    5100
ggagcttcca gggggaaacg cctggtatct ttatagtcct gtcgggtttc gccacctctg    5160
acttgagcgt cgatttttgt gatgctcgtc aggggggcgg agcctatgga aaaacgccag    5220
caacgcggcc ttttacggt tcctggcctt ttgctggcct tttgctcaca tgttctttcc    5280
tgcgttatcc cctgattctg tggataaccg tattaccgcc tttgagtgag ctgataccgc    5340
tcgccgcagc cgaacgaccg agcgcagcga gtcagtgagc gaggaagcgg aagagcgccc    5400
aatacgcaaa ccgcctctcc ccgcgcgttg gccgattcat taatgcagct ggcacgacag    5460
gtttcccgac tggaaagcgg gcagtgagcg caacgcaatt aatgtgagtt agctcactca    5520
ttaggcaccc caggctttac actttatgct tccggctcgt atgttgtgtg gaattgtgag    5580
cggataacaa tttcacacag gaaacagcta tgaccatgat tacgccaagc gcgcaattaa    5640
ccctcactaa agggaacaaa agctggagct gcaagcttaa tgtagtctta tgcaatactc    5700
ttgtagtctt gcaacatggt aacgatgagt tagcaacatg ccttacaagg agagaaaaag    5760
caccgtgcat gccgattggt ggaagtaagg tggtacgatc gtgccttatt aggaaggcaa    5820
cagacgggtc tgacatggat tggacgaacc actgaattgc cgcattgcag agatattgta    5880
tttaagtgcc tagctcgata caataaacgg gtctctctgg ttagaccaga tctgagcctg    5940
ggagctctct ggctaactag ggaacccact gcttaagcct caataaagct tgccttgagt    6000
gcttcaagta gtgtgtgccc gtctgttgtg tgactctggt aactagagat ccctcagacc    6060
cttttagtca gtgtggaaaa tctctagcag tggcgcccga acaggacct gaaagcgaaa    6120 gggaaaccag agctctctcg acgcaggact cggcttgctg aagcgcgcac ggcaagaggc    6180
gaggggcggc gactggtgag tacgccaaaa attttgacta gcggaggcta aaggagaga    6240 gatgggtgcg agagcgtcag tattaagcgg gggagaatta gatcgcgatg ggaaaaaatt    6300
cggttaaggc cagggggaaa gaaaaaatat aaattaaaac atatagtatg ggcaagcagg    6360
gagctagaac gattcgcagt taatcctggc ctgttagaaa catcagaagg ctgtagacaa    6420
atactgggac agctacaacc atcccttcag acaggatcag aagaacttag atcattatat    6480
aatacagtag caaccctcta ttgtgtgcat caaaggatag agataaaaga caccaaggaa    6540
gctttagaca agatagagga agagcaaaac aaaagtaaga ccaccgcaca gcaagcggcc    6600
gctgatcttc agacctggag gaggagatat gagggacaat tggagaagtg aattatataa    6660
atataaagta gtaaaaattg aaccattagg agtagcaccc accaaggcaa agagaagagt    6720
ggtgcagaga gaaaaaagag cagtgggaat aggagctttg ttccttgggt tcttgggagc    6780
```

```
agcaggaagc actatgggcg cagcctcaat gacgctgacg gtacaggcca gacaattatt    6840
gtctggtata gtgcagcagc agaacaattt gctgagggct attgaggcgc aacagcatct    6900
gttgcaactc acagtctggg gcatcaagca gctccaggca gaatcctgg ctgtggaaag     6960 ataccctaaag gatcaacagc tcctggggat ttggggttgc tctggaaaac tcatttgcac   7020
cactgctgtg ccttggaatg ctagttggag taataaatct ctggaacaga ttggaatcac    7080
acgacctgga tggagtggga cagagaaatt aacaattaca caagcttaat acactcctta    7140
attgaagaat cgcaaaacca gcaagaaaag aatgaacaag aattattgga attagataaa    7200
tgggcaagtt tgtggaattg gtttaacata acaaattggc tgtggtatat aaaattattc    7260
ataatgatag taggaggctt ggtaggttta agaatagttt ttgctgtact ttctatagtg    7320
aatagagtta ggcagggata ttcaccatta tcgtttcaga cccacctccc aaccccgagg    7380
ggacccgaca ggcccgaagg aatagaagaa gaaggtggag agagagacag agacagatcc    7440
attcgattag tgaacggatc tcgacggtat cgattagact gtagcccagg aatatggcag    7500
ctagattgta cacatttaga aggaaaagtt atcttggtag cagttcatgt agccagtgga    7560
tatatagaag cagaagtaat tccagcagag acagggcaag aaacagcata cttcctctta    7620
aaattagcag gaagatggcc agtaaaaaca gtacatacag acaatggcag caatttcacc    7680
agtactacag ttaaggccgc ctgttggtgg gcggggatca agcaggaatt tggcattccc    7740
tacaatcccc aaagtcaagg agtaatagaa tctatgaata agaattaaa gaaaattata    7800 ggacaggtaa gagatcaggc tgaacatctt aagacagcag tacaaatggc agtattcatc    7860
cacaatttta aaagaaaagg ggggattggg gggtacagtg caggggaaag aatagtagac    7920
ataatagcaa cagacataca aactaaagaa ttacaaaaac aaattacaaa aattcaaaat    7980
tttcgggttt attacaggga cagcagagat ccagtttggc tgcatacgcg tcgtgaggct    8040
ccggtgcccg tcagtgggca gagcgcacat cgcccacagt ccccgagaag ttgggggggag   8100 gggtcggcaa ttgaaccggt gcctagagaa ggtggcgcgg ggtaaactgg gaaagtgatg    8160
tcgtgtactg gctccgcctt tttcccgagg gtgggggaga accgtatata agtgcagtag    8220
tcgccgtgaa cgttcttttt cgcaacgggt ttgccgccag aacacaggta agtgccgtgt    8280
gtggttcccg cgggcctggc ctctttacgg gttatggccc ttgcgtgcct tgaattactt    8340
ccacctggct gcagtacgtg attcttgatc ccgagcttcg ggttggaagt gggtgggaga    8400
gttcgaggcc ttgcgcttaa ggagcccctt cgcctcgtgc ttgagttgag gcctggcctg    8460
ggcgctgggc ccgccgcgtg cgaatctggt ggcaccttcg cgcctgtctc gctgctttcg    8520
ataagtctct agccatttaa aattttttgat gacctgctgc gacgcttttt ttctggcaag    8580
atagtcttgt aaatgcgggc caagatctgc acactggtat ttcggttttt ggggccgcgg    8640
gcggcgacgg ggcccgtgcg tcccagcgca catgttcggc gaggcggggc ctgcgagcgc    8700
ggccaccgag aatcggacgg gggtagtctc aagctggccg gcctgctctg tgcctggcc    8760 tcgcgccgcc gtgtatcgcc ccgccctggg cggcaaggct ggcccggtcg gcaccagttg    8820
cgtgagcgga agatggccg cttccggcc ctgctgcagg gagctcaaaa tggaggacgc    8880
ggcgctcggg agagcgggcg ggtgagtcac ccacacaaag gaaaagggcc tttccgtcct    8940
cagccgtcgc ttcatgtgac tccacggagt accgggcgcc gtccaggcac ctcgattagt    9000
tctcgagctt ttggagtacg tcgtctttag gttgggggga ggggttttat gcgatggagt    9060
ttccccacac tgagtgggtg gagactgaag ttaggccagc ttggcacttg atgtaattct    9120
```

```
ccttggaatt tgcccttttt gagtttggat cttggttcat tctcaagcct cagacagtgg    9180
ttcaaagttt ttttcttcca tttcaggtgt cgtgagctag ctctagag                 9228

<210> SEQ ID NO 2
<211> LENGTH: 63
<212> TYPE: DNA
<213> ORGANISM: Artificial Sequence
<220> FEATURE:
<223> OTHER INFORMATION: Chemically Synthesized

<400> SEQUENCE: 2
atggccttac cagtgaccgc cttgctcctg ccgctggcct tgctgctcca cgccgccagg    60
ccg                                                                  63

<210> SEQ ID NO 3
<211> LENGTH: 768
<212> TYPE: DNA
<213> ORGANISM: Artificial Sequence
<220> FEATURE:
<223> OTHER INFORMATION: Chemically Synthesized

<400> SEQUENCE: 3
tctagagcgg cccagccggc catggcccag gtgcagctgc agcagtctgg agctgagctg    60
gtgaagcctg gggcttcagt gaagatatcc tgcaaggctt ctggttactc atttactggc   120
tactttatga actgggtgaa gcagagccat ggaaagagcc ttgagtggat tggacgtatt   180
catccttacg atggtgatac tttctacaac cagaacttca aggacaaggc cacattgact   240
gtagacaaat cctctaacac agcccacatg agctcctga gcctgacatc tgaggacttt   300
gcagtctatt attgtacaag atacgacggt agtcgggcta tggactactg gggccaaggg   360
accacggtca ccgtctcctc aggtggaggc ggttcaggcg gaggtggctc tggcggtggc   420
ggatcggaca tcgagctcac tcagtctcca gcttctttgg ctgtgtctct agggcagagg   480
gccatcatct cctgcaaggc cagccaaagt gtcagttttg ctggtactag tttaatgcac   540
tggtaccacc agaaaccagg acagcaaccc aaactcctca tctatcgtgc atccaaccta   600
gaagctgggg ttcctaccag gtttagtggc agtgggtcta agacagactt caccctcaat   660
atccatcctg tggaggagga ggatgctgca acctattact gtcagcaaag tagggaatat   720
ccgtacacgt tcggaggggg gacaaagttg gaaataaaac gggcggcc                768

<210> SEQ ID NO 4
<211> LENGTH: 135
<212> TYPE: DNA
<213> ORGANISM: Artificial Sequence
<220> FEATURE:
<223> OTHER INFORMATION: Chemically Synthesized

<400> SEQUENCE: 4
accacgacgc cagcgccgcg accaccaaca ccggcgccca ccatcgcgtc gcagccctg     60 tccctgcgcc cagaggcgtg ccggccagcg gcggggggcg cagtgcacac gagggggctg   120
gacttcgcct gtgat                                                    135

<210> SEQ ID NO 5
<211> LENGTH: 72
<212> TYPE: DNA
<213> ORGANISM: Artificial Sequence
<220> FEATURE:
<223> OTHER INFORMATION: Chemically Synthesized

<400> SEQUENCE: 5
```

```
atctacatct gggcgccctt ggccgggact tgtggggtcc ttctcctgtc actggttatc    60 acccttact gc                                                        72
```

<210> SEQ ID NO 6
<211> LENGTH: 126
<212> TYPE: DNA
<213> ORGANISM: Artificial Sequence
<220> FEATURE:
<223> OTHER INFORMATION: Chemically Synthesized

<400> SEQUENCE: 6

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                             126
```

<210> SEQ ID NO 7
<211> LENGTH: 336
<212> TYPE: DNA
<213> ORGANISM: Artificial Sequence
<220> FEATURE:
<223> OTHER INFORMATION: Chemically Synthesized

<400> SEQUENCE: 7

```
agagtgaagt tcagcaggag cgcagacgcc cccgcgtaca agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240 cggagggggca aggggcacga tggcctttac cagggtctca gtacagccac caaggacacc   300
tacgacgccc ttcacatgca ggccctgccc cctcgc                             336
```

<210> SEQ ID NO 8
<211> LENGTH: 182
<212> TYPE: DNA
<213> ORGANISM: Artificial Sequence
<220> FEATURE:
<223> OTHER INFORMATION: Chemically Synthesized

<400> SEQUENCE: 8

```
gggtctctct ggttagacca gatctgagcc tgggagctct ctggctaact agggaaccca    60
ctgcttaagc ctcaataaag cttgccttga gtgcttcaag tagtgtgtgc ccgtctgttg   120
tgtgactctg gtaactagag atccctcaga cccttttagt cagtgtggaa aatctctagc   180
ag                                                                 182
```

<210> SEQ ID NO 9
<211> LENGTH: 229
<212> TYPE: DNA
<213> ORGANISM: Artificial Sequence
<220> FEATURE:
<223> OTHER INFORMATION: Chemically Synthesized

<400> SEQUENCE: 9

```
atgtagtctt atgcaatact cttgtagtct tgcaacatgg taacgatgag ttagcaacat    60
gccttacaag gagagaaaaa gcaccgtgca tgccgattgg tggaagtaag gtggtacgat   120
cgtgccttat taggaaggca acagacgggt ctgacatgga ttggacgaac cactgaattg   180
ccgcattgca gagatattgt atttaagtgc ctagctcgat acaataaac               229
```

<210> SEQ ID NO 10
<211> LENGTH: 1372
<212> TYPE: DNA
<213> ORGANISM: Artificial Sequence
<220> FEATURE:
<223> OTHER INFORMATION: Chemically Synthesized

<400> SEQUENCE: 10

| | | | | | |
|---|---|---|---|---|---|
| gaacagggac | ctgaaagcga | aagggaaacc | agagctctct | cgacgcagga | ctcggcttgc | 60 |
| tgaagcgcgc | acggcaagag | gcgaggggcg | gcgactggtg | agtacgccaa | aaattttgac | 120 |
| tagcggaggc | tagaaggaga | gagatgggtg | cgagagcgtc | agtattaagc | gggggagaat | 180 |
| tagatcgcga | tgggaaaaaa | ttcggttaag | gccaggggga | agaaaaaat | ataaattaaa | 240 |
| acatatagta | tgggcaagca | gggagctaga | acgattcgca | gttaatcctg | gcctgttaga | 300 |
| aacatcagaa | ggctgtagac | aaatactggg | acagctacaa | ccatcccttc | agacaggatc | 360 |
| agaagaactt | agatcattat | ataatacagt | agcaaccctc | tattgtgtgc | atcaaaggat | 420 |
| agagataaaa | gacaccaagg | aagctttaga | caagatagag | gaagagcaaa | acaaaagtaa | 480 |
| gaccaccgca | cagcaagcgg | ccgctgatct | tcagacctgg | aggaggagat | atgagggaca | 540 |
| attggagaag | tgaattatat | aaatataaag | tagtaaaaat | tgaaccatta | ggagtagcac | 600 |
| ccaccaaggc | aaagaagaa | gtggtgcaga | gagaaaaaag | agcagtggga | ataggagctt | 660 |
| tgttccttgg | gttcttggga | gcagcaggaa | gcactatggg | cgcagcctca | atgacgctga | 720 |
| cggtacaggc | cagacaatta | ttgtctggta | tagtgcagca | gcagaacaat | ttgctgaggg | 780 |
| ctattgaggc | gcaacagcat | ctgttgcaac | tcacagtctg | gggcatcaag | cagctccagg | 840 |
| caagaatcct | ggctgtggaa | agatacctaa | aggatcaaca | gctcctgggg | atttggggtt | 900 |
| gctctggaaa | actcatttgc | accactgctg | tgccttggaa | tgctagttgg | agtaataaat | 960 |
| ctctggaaca | gattggaatc | acacgacctg | gatggagtgg | gacagagaaa | ttaacaatta | 1020 |
| cacaagctta | atacactcct | taattgaaga | atcgcaaaac | cagcaagaaa | agaatgaaca | 1080 |
| agaattattg | gaattagata | aatgggcaag | tttgtggaat | tggtttaaca | taacaaattg | 1140 |
| gctgtggtat | ataaaattat | tcataatgat | agtaggaggc | ttggtaggtt | taagaatagt | 1200 |
| ttttgctgta | ctttctatag | tgaatagagt | taggcaggga | tattcaccat | tatcgtttca | 1260 |
| gacccacctc | ccaaccccga | ggggacccga | caggcccgaa | ggaatagaag | aagaaggtgg | 1320 |
| agagagagac | agagacagat | ccattcgatt | agtgaacgga | tctcgacggt | at | 1372 |

<210> SEQ ID NO 11
<211> LENGTH: 540
<212> TYPE: DNA
<213> ORGANISM: Artificial Sequence
<220> FEATURE:
<223> OTHER INFORMATION: Chemically Synthesized

<400> SEQUENCE: 11

| | | | | | |
|---|---|---|---|---|---|
| tagcccagga | atatggcagc | tagattgtac | acatttagaa | ggaaaagtta | tcttggtagc | 60 |
| agttcatgta | gccagtggat | atatagaagc | agaagtaatt | ccagcagaga | cagggcaaga | 120 |
| aacagcatac | ttcctcttaa | aattagcagg | aagatggcca | gtaaaaacag | tacatacaga | 180 |
| caatggcagc | aatttcacca | gtactacagt | taaggccgcc | tgttggtggg | cggggatcaa | 240 |
| gcaggaattt | ggcattccct | acaatcccca | aagtcaagga | gtaatagaat | ctatgaataa | 300 |
| agaattaaag | aaaattatag | gacaggtaag | agatcaggct | gaacatctta | agacagcagt | 360 |
| acaaatggca | gtattcatcc | acaattttaa | aagaaaaggg | gggattgggg | ggtacagtgc | 420 |

```
agggggaaaga atagtagaca taatagcaac agacatacaa actaaagaat tacaaaaaca    480
aattacaaaa attcaaaatt ttcgggttta ttacagggac agcagagatc cagtttggct    540
```

<210> SEQ ID NO 12
<211> LENGTH: 1184
<212> TYPE: DNA
<213> ORGANISM: Artificial Sequence
<220> FEATURE:
<223> OTHER INFORMATION: Chemically Synthesized

<400> SEQUENCE: 12

```
gtgaggctcc ggtgcccgtc agtgggcaga gcgcacatcg cccacagtcc ccgagaagtt     60 gggggggaggg gtcggcaatt gaaccggtgc ctagagaagg tggcgcgggg taaactggga    120
aagtgatgtc gtgtactggc tccgcctttt tcccgagggt gggggagaac cgtatataag    180
tgcagtagtc gccgtgaacg ttcttttttcg caacgggttt gccgccagaa cacaggtaag    240
tgccgtgtgt ggtccccgcg ggcctggcct ctttacgggt tatggccctt gcgtgccttg    300
aattacttcc acctggctgc agtacgtgat tcttgatccc gagcttcggg ttggaagtgg    360
gtgggagagt tcgaggcctt gcgcttaagg agccccttcg cctcgtgctt gagttgaggc    420
ctggcctggg cgctggggcc gccgcgtgcg aatctggtgg caccttcgcg cctgtctcgc    480
tgctttcgat aagtctctag ccatttaaaa ttttttgatga cctgctgcga cgcttttttt    540
ctggcaagat agtcttgtaa atgcgggcca agatctgcac actggtattt cggttttgg     600 ggccgcgggc ggcgacgggg cccgtgcgtc ccagcgcaca tgttcggcga ggcggggcct    660
gcgagcgcgg ccaccgagaa tcggacgggg gtagtctcaa gctggccggc ctgctctggt    720
gcctggcctc gcgccgccgt gtatcgcccc gccctgggcg gcaaggctgg cccggtcggc    780
accagttgcg tgagcggaaa gatggccgct tcccggccct gctgcaggga gctcaaaatg    840
gaggacgcgg cgctcgggag agcgggcggg tgagtcaccc acacaaagga aaagggcctt    900
tccgtcctca gccgtcgctt catgtgactc cacggagtac cgggcgccgt ccaggcacct    960
cgattagttc tcgagctttt ggagtacgtc gtctttaggt tggggggagg ggttttatgc   1020
gatgagtttt ccccacactg agtgggtgga gactgaagtt aggccagctt ggcacttgat   1080
gtaattctcc ttggaatttg ccctttttga gtttggatct tggttcattc tcaagcctca   1140
gacagtggtt caaagttttt ttcttccatt tcaggtgtcg tgag                    1184
```

<210> SEQ ID NO 13
<211> LENGTH: 504
<212> TYPE: PRT
<213> ORGANISM: Artificial Sequence
<220> FEATURE:
<223> OTHER INFORMATION: Chemically Synthesized

<400> SEQUENCE: 13

```
Met Ala Leu Pro Val Thr Ala Leu Leu Leu Pro Leu Ala Leu Leu Leu
1               5                   10                  15

His Ala Ala Arg Pro Gly Ser Ser Arg Ala Ala Gln Pro Ala Met Ala
                20                  25                  30

Gln Val Gln Leu Gln Gln Ser Gly Ala Glu Leu Val Lys Pro Gly Ala
            35                  40                  45

Ser Val Lys Ile Ser Cys Lys Ala Ser Gly Tyr Ser Phe Thr Gly Tyr
        50                  55                  60

Phe Met Asn Trp Val Lys Gln Ser His Gly Lys Ser Leu Glu Trp Ile
65                  70                  75                  80
```

Gly Arg Ile His Pro Tyr Asp Gly Asp Thr Phe Tyr Asn Gln Asn Phe
                85                  90                  95

Lys Asp Lys Ala Thr Leu Thr Val Asp Lys Ser Ser Asn Thr Ala His
                100                 105                 110

Met Glu Leu Leu Ser Leu Thr Ser Glu Asp Phe Ala Val Tyr Tyr Cys
                115                 120                 125

Thr Arg Tyr Asp Gly Ser Arg Ala Met Asp Tyr Trp Gly Gln Gly Thr
                130                 135                 140

Thr Val Thr Val Ser Ser Gly Gly Gly Gly Ser Gly Gly Gly Gly Ser
145                 150                 155                 160

Gly Gly Gly Gly Ser Asp Ile Glu Leu Thr Gln Ser Pro Ala Ser Leu
                165                 170                 175

Ala Val Ser Leu Gly Gln Arg Ala Ile Ile Ser Cys Lys Ala Ser Gln
                180                 185                 190

Ser Val Ser Phe Ala Gly Thr Ser Leu Met His Trp Tyr His Gln Lys
                195                 200                 205

Pro Gly Gln Gln Pro Lys Leu Leu Ile Tyr Arg Ala Ser Asn Leu Glu
                210                 215                 220

Ala Gly Val Pro Thr Arg Phe Ser Gly Ser Gly Ser Lys Thr Asp Phe
225                 230                 235                 240

Thr Leu Asn Ile His Pro Val Glu Glu Asp Ala Ala Thr Tyr Tyr
                245                 250                 255

Cys Gln Gln Ser Arg Glu Tyr Pro Tyr Thr Phe Gly Gly Gly Thr Lys
                260                 265                 270

Leu Glu Ile Lys Arg Ala Ala Ala Ser Thr Thr Thr Pro Ala Pro Arg
                275                 280                 285

Pro Pro Thr Pro Ala Pro Thr Ile Ala Ser Gln Pro Leu Ser Leu Arg
                290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Lys Arg
                340                 345                 350

Gly Arg Lys Lys Leu Leu Tyr Ile Phe Lys Gln Pro Phe Met Arg Pro
                355                 360                 365

Val Gln Thr Thr Gln Glu Glu Asp Gly Cys Ser Cys Arg Phe Pro Glu
                370                 375                 380

Glu Glu Glu Gly Gly Cys Glu Leu Arg Val Lys Phe Ser Arg Ser Ala
385                 390                 395                 400

Asp Ala Pro Ala Tyr Lys Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
                420                 425                 430

Arg Asp Pro Glu Met Gly Gly Lys Pro Arg Arg Lys Asn Pro Gln Glu
                435                 440                 445

Gly Leu Tyr Asn Glu Leu Gln Lys Asp Lys Met Ala Glu Ala Tyr Ser
                450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

```
His Met Gln Ala Leu Pro Pro Arg
            500

<210> SEQ ID NO 14
<211> LENGTH: 21
<212> TYPE: PRT
<213> ORGANISM: Artificial Sequence
<220> FEATURE:
<223> OTHER INFORMATION: Chemically Synthesized

<400> SEQUENCE: 14

Met Ala Leu Pro Val Thr Ala Leu Leu Leu Pro Leu Ala Leu Leu Leu
1               5                   10                  15

His Ala Ala Arg Pro
            20

<210> SEQ ID NO 15
<211> LENGTH: 256
<212> TYPE: PRT
<213> ORGANISM: Artificial Sequence
<220> FEATURE:
<223> OTHER INFORMATION: Chemically Synthesized

<400> SEQUENCE: 15

Ser Arg Ala Ala Gln Pro Ala Met Ala Gln Val Gln Leu Gln Gln Ser
1               5                   10                  15

Gly Ala Glu Leu Val Lys Pro Gly Ala Ser Val Lys Ile Ser Cys Lys
                20                  25                  30

Ala Ser Gly Tyr Ser Phe Thr Gly Tyr Phe Met Asn Trp Val Lys Gln
            35                  40                  45

Ser His Gly Lys Ser Leu Glu Trp Ile Gly Arg Ile His Pro Tyr Asp
        50                  55                  60

Gly Asp Thr Phe Tyr Asn Gln Asn Phe Lys Asp Lys Ala Thr Leu Thr
65                  70                  75                  80

Val Asp Lys Ser Ser Asn Thr Ala His Met Glu Leu Leu Ser Leu Thr
                85                  90                  95

Ser Glu Asp Phe Ala Val Tyr Tyr Cys Thr Arg Tyr Asp Gly Ser Arg
            100                 105                 110

Ala Met Asp Tyr Trp Gly Gln Gly Thr Thr Val Thr Val Ser Ser Gly
        115                 120                 125

Gly Gly Gly Ser Gly Gly Gly Ser Gly Gly Gly Ser Asp Ile
130                 135                 140

Glu Leu Thr Gln Ser Pro Ala Ser Leu Ala Val Ser Leu Gly Gln Arg
145                 150                 155                 160

Ala Ile Ile Ser Cys Lys Ala Ser Gln Ser Val Ser Phe Ala Gly Thr
                165                 170                 175

Ser Leu Met His Trp Tyr His Gln Lys Pro Gly Gln Gln Pro Lys Leu
            180                 185                 190

Leu Ile Tyr Arg Ala Ser Asn Leu Glu Ala Gly Val Pro Thr Arg Phe
        195                 200                 205

Ser Gly Ser Gly Ser Lys Thr Asp Phe Thr Leu Asn Ile His Pro Val
210                 215                 220

Glu Glu Glu Asp Ala Ala Thr Tyr Tyr Cys Gln Gln Ser Arg Glu Tyr
225                 230                 235                 240

Pro Tyr Thr Phe Gly Gly Gly Thr Lys Leu Glu Ile Lys Arg Ala Ala
                245                 250                 255

<210> SEQ ID NO 16
```

<211> LENGTH: 45
<212> TYPE: PRT
<213> ORGANISM: Artificial Sequence
<220> FEATURE:
<223> OTHER INFORMATION: Chemically Synthesized

<400> SEQUENCE: 16

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 17
<211> LENGTH: 24
<212> TYPE: PRT
<213> ORGANISM: Artificial Sequence
<220> FEATURE:
<223> OTHER INFORMATION: Chemically Synthesized

<400> SEQUENCE: 17

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 18
<211> LENGTH: 42
<212> TYPE: PRT
<213> ORGANISM: Artificial Sequence
<220> FEATURE:
<223> OTHER INFORMATION: Chemically Synthesized

<400> SEQUENCE: 18

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 19
<211> LENGTH: 112
<212> TYPE: PRT
<213> ORGANISM: Artificial Sequence
<220> FEATURE:
<223> OTHER INFORMATION: Chemically Synthesized

<400> SEQUENCE: 19

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
        100                 105                 110

<210> SEQ ID NO 20
<211> LENGTH: 9189
<212> TYPE: DNA
<213> ORGANISM: Artificial Sequence
<220> FEATURE:
<223> OTHER INFORMATION: Chemically Synthesized

<400> SEQUENCE: 20

| | | | | | |
|---|---|---|---|---|---|
| atggccttac | cagtgaccgc | cttgctcctg | ccgctggcct | tgctgctcca | cgccgccagg | 60 |
| ccgggatccc | agctggtgga | gtctggggga | ggcttggtac | agccagggcg | gtccctgaga | 120 |
| ctctcctgca | caacttctgg | attcactttt | ggtgattatg | ctatgatctg | ggcccgccag | 180 |
| gctccaggga | aggggctgga | gtgggtctca | tccattagta | gtagtagtag | ttacatatac | 240 |
| tacgcagact | cagtgaaggg | ccgattcacc | atctccagag | acaacgccaa | gaactcactg | 300 |
| tatctgcaaa | tgaacagcct | gagagccgag | gacacggctg | tgtattactg | tgcgagagaa | 360 |
| cgatacgatt | tttggagtgg | aatggacgtc | tggggcaaag | gaccacggt | caccgtctcg | 420 |
| agtggtggag | gcggttcagg | cggaggtggc | tctggcggta | gtgcacagtc | tgccctgact | 480 |
| cagcctgcct | ccgtgtctgg | gtctcctgga | cagtcgatca | ccatctcctg | cactggaacc | 540 |
| agcagtgatg | ttgggagtta | taaccttgtc | tcctggtacc | aacagcaccc | aggcaaagcc | 600 |
| cccaaactca | tgatttatga | gggcagtaag | cggccctcag | gggtttctaa | tcgcttctct | 660 |
| ggctccaagt | ctggcaacgc | ggcctccctg | acaatctctg | gctccaggc | tgaggacgag | 720 |
| gctgattatt | actgccagtc | ctatgacagc | agcctgagtg | tggtattcgg | cggagggacc | 780 |
| aagctgaccg | tcctaggtgc | tagcaccacg | acgccagcgc | cgcgaccacc | aacaccggcg | 840 |
| cccaccatcg | cgtcgcagcc | cctgtccctg | cgcccagagg | cgtgccggcc | agcggcgggg | 900 |
| ggcgcagtgc | acacgagggg | gctggacttc | gcctgtgata | tctacatctg | gcgcgccttg | 960 |
| gccgggactt | gtgggggtcct | tctcctgtca | ctggttatca | ccctttactg | caaacggggc | 1020 |
| agaaagaaac | tcctgtatat | attcaaacaa | ccatttatga | gaccagtaca | aactactcaa | 1080 |
| gaggaagatg | gctgtagctg | ccgatttcca | gaagaagaag | aaggaggatg | tgaactgaga | 1140 |
| gtgaagttca | gcaggagcgc | agacgccccc | gcgtacaagc | agggccagaa | ccagctctat | 1200 |
| aacgagctca | atctaggacg | aagagaggag | tacgatgttt | tggacaagag | acgtggccgg | 1260 |
| gaccctgaga | tggggggaaa | gccgagaagg | aagaaccctc | aggaaggcct | gtacaatgaa | 1320 |
| ctgcagaaag | ataagatggc | ggaggcctac | agtgagattg | gatgaaagg | cgagcgccgg | 1380 |
| agggcaagg | ggcacgatgg | cctttaccag | ggtctcagta | cagccaccaa | ggacacctac | 1440 |
| gacgcccttc | acatgcaggc | cctgcccct | cgctaagtcg | actcgacaat | caacctctgg | 1500 |
| attacaaaat | ttgtgaaaga | ttgactggta | ttcttaacta | tgttgctcct | tttacgctat | 1560 |
| gtggatacgc | tgctttaatg | cctttgtatc | atgctattgc | ttcccgtatg | gctttcattt | 1620 |
| tctcctcctt | gtataaatcc | tggttgctgt | ctctttatga | ggagttgtgg | cccgttgtca | 1680 |
| ggcaacgtgg | cgtggtgtgc | actgtgtttg | ctgacgcaac | ccccactggt | tggggcattg | 1740 |
| ccaccacctg | tcagctcctt | ccgggactt | tcgctttccc | cctccctatt | gccacggcgg | 1800 |
| aactcatcgc | cgcctgcctt | gcccgctgct | ggacagggc | tcggctgttg | gcactgaca | 1860 |
| attccgtggt | gttgtcgggg | aagctgacgt | cctttccatg | gctgctcgcc | tgtgttgcca | 1920 |
| cctggattct | gcgcgggacg | tccttctgct | acgtcccttc | ggccctcaat | ccagcggacc | 1980 |

```
ttccttcccg cggcctgctg ccggctctgc ggcctcttcc gcgtcttcgc cttcgccctc    2040
agacgagtcg gatctccctt tgggccgcct ccccgcctgg aattcgagct cggtacctt     2100 aagaccaatg acttacaagg cagctgtaga tcttagccac ttttaaaag aaaaggggg      2160 actggaaggg ctaattcact cccaacgaag acaagatctg cttttgctt gtactgggtc    2220 tctctggtta gaccagatct gagcctggga gctctctggc taactaggga acccactgct    2280
taagcctcaa taaagcttgc cttgagtgct tcaagtagtg tgtgcccgtc tgttgtgtga    2340
ctctggtaac tagagatccc tcagaccctt ttagtcagtg tggaaaatct ctagcagtag    2400
tagttcatgt catcttatta ttcagtattt ataacttgca aagaaatgaa tatcagagag    2460
tgagaggaac ttgtttattg cagcttataa tggttacaaa taaagcaata gcatcacaaa    2520
tttcacaaat aaagcatttt tttcactgca ttctagttgt ggtttgtcca aactcatcaa    2580
tgtatcttat catgtctggc tctagctatc ccgcccctaa ctccgcccag ttccgcccat    2640
tctccgcccc atggctgact aattttttt atttatgcag aggccgaggc cgcctcggcc    2700
tctgagctat tccagaagta gtgaggaggc ttttttggag gcctaggctt ttgcgtcgag    2760
acgtacccaa ttcgccctat agtgagtcgt attacgcgcg ctcactggcc gtcgttttac    2820
aacgtcgtga ctgggaaaac cctggcgtta cccaacttaa tcgccttgca gcacatcccc    2880
ctttcgccag ctggcgtaat agcgaagagg cccgcaccga tcgcccttcc caacagttgc    2940
gcagcctgaa tggcgaatgg cgcgacgcgc cctgtagcgg cgcattaagc gcggcgggtg    3000
tggtggttac gcgcagcgtg accgctacac ttgccagcgc cctagcgccc gctcctttcg    3060
ctttcttccc ttcctttctc gccacgttcg ccggctttcc ccgtcaagct ctaaatcggg    3120
ggctcccttt agggttccga tttagtgctt tacggcacct cgaccccaaa aaacttgatt    3180
agggtgatgg ttcacgtagt gggccatcgc cctgatagac ggtttttcgc cctttgacgt    3240
tggagtccac gttctttaat agtggactct tgttccaaac tggaacaaca ctcaacccta    3300
tctcggtcta ttcttttgat ttataaggga ttttgccgat ttcggcctat tggttaaaaa    3360
atgagctgat ttaacaaaaa tttaacgcga attttaacaa atattaacg tttacaattt     3420 cccaggtggc acttttcggg gaaatgtgcg cggaaccct atttgtttat ttttctaaat     3480
acattcaaat atgtatccgc tcatgagaca ataaccctga taaatgcttc aataatattg    3540
aaaaaggaag agtatgagta ttcaacattt ccgtgtcgcc cttattccct tttttgcggc    3600
attttgcctt cctgttttg ctcacccaga aacgctggtg aaagtaaaag atgctgaaga     3660
tcagttgggt gcacgagtgg gttacatcga actggatctc aacagcggta agatccttga    3720
gagttttcgc cccgaagaac gttttccaat gatgagcact tttaaagttc tgctatgtgg    3780
cgcggtatta tcccgtattg acgccgggca agagcaactc ggtcgccgca tacactattc    3840
tcagaatgac ttggttgagt actcaccagt cacagaaaag catcttacgg atggcatgac    3900
agtaagagaa ttatgcagtg ctgccataac catgagtgat aacactgcgg ccaacttact    3960
tctgacaacg atcggaggac cgaaggagct aaccgctttt ttgcacaaca tgggggatca    4020
tgtaactcgc cttgatcgtt gggaaccgga gctgaatgaa gccataccaa acgacgagcg    4080
tgacaccacg atgcctgtag caatggcaac aacgttgcgc aaactattaa ctggcgaact    4140
acttactcta gcttcccggc aacaattaat agactggatg gaggcggata agttgcagg     4200 accacttctg cgctcggccc ttccggctgg ctggtttatt gctgataaat ctggagccgg    4260
tgagcgtggg tctcgcggta tcattgcagc actggggcca gatggtaagc cctcccgtat    4320
```

-continued

```
cgtagttatc tacacgacgg ggagtcaggc aactatggat gaacgaaata gacagatcgc    4380
tgagataggt gcctcactga ttaagcattg gtaactgtca gaccaagttt actcatatat    4440
actttagatt gatttaaaac ttcatttttta atttaaaagg atctaggtga agatcctttt   4500
tgataatctc atgaccaaaa tcccttaacg tgagttttcg ttccactgag cgtcagaccc    4560
cgtagaaaag atcaaaggat cttcttgaga tcctttttttt ctgcgcgtaa tctgctgctt   4620
gcaaacaaaa aaaccaccgc taccagcggt ggtttgtttg ccggatcaag agctaccaac    4680
tcttttttccg aaggtaactg gcttcagcag agcgcagata ccaaatactg tccttctagt   4740
gtagccgtag ttaggccacc acttcaagaa ctctgtagca ccgcctacat acctcgctct    4800
gctaatcctg ttaccagtgg ctgctgccag tggcgataag tcgtgtctta ccgggttgga    4860
ctcaagacga tagttaccgg ataaggcgca gcggtcgggc tgaacggggg gttcgtgcac    4920
acagcccagc ttggagcgaa cgacctacac cgaactgaga tacctacagc gtgagctatg    4980
agaaagcgcc acgcttcccg aagggagaaa ggcggacagg tatccggtaa gcggcagggt    5040
cggaacagga gagcgcacga gggagcttcc agggggaaac gcctggtatc tttatagtcc    5100
tgtcgggttt cgccacctct gacttgagcg tcgatttttg tgatgctcgt caggggggcg    5160
gagcctatgg aaaaacgcca gcaacgcggc cttttttacgg ttcctggcct tttgctggcc    5220
ttttgctcac atgttctttc ctgcgttatc ccctgattct gtggataacc gtattaccgc    5280
ctttgagtga gctgataccg ctcgccgcag ccgaacgacc gagcgcagcg agtcagtgag    5340
cgaggaagcg gaagagcgcc caatacgcaa accgcctctc ccgcgcgtt ggccgattca     5400
ttaatgcagc tggcacgaca ggtttcccga ctggaaagcg ggcagtgagc gcaacgcaat    5460
taatgtgagt tagctcactc attaggcacc ccaggcttta cactttatgc ttccggctcg    5520
tatgttgtgt ggaattgtga gcggataaca atttcacaca ggaaacagct atgaccatga    5580
ttacgccaag cgcgcaatta accctcacta aagggaacaa aagctggagc tgcaagctta    5640
atgtagtctt atgcaatact cttgtagtct tgcaacatgg taacgatgag ttagcaacat    5700
gccttacaag gagagaaaaa gcaccgtgca tgccgattgg tggaagtaag gtggtacgat    5760
cgtgccttat taggaaggca acagacgggt ctgacatgga ttggacgaac cactgaattg    5820
ccgcattgca gagatattgt atttaagtgc ctagctcgat acaataaacg ggtctctctg    5880
gttagaccag atctgagcct gggagctctc tggctaacta gggaacccac tgcttaagcc    5940
tcaataaagc ttgccttgag tgcttcaagt agtgtgtgcc cgtctgttgt gtgactctgg    6000
taactagaga tccctcagac ccttttagtc agtgtggaaa atctctagca gtggcgcccg    6060
aacagggacc tgaaagcgaa agggaaacca gagctctctc gacgcaggac tcggcttgct    6120
gaagcgcgca cggcaagagg cgaggggcgg cgactggtga gtacgccaaa aattttgact    6180
agcggaggct agaaggagag agatgggtgc gagagcgtca gtattaagcg ggggagaatt    6240
agatcgcgat gggaaaaaat tcggttaagg ccagggggaa agaaaaaata taaattaaaa    6300
catatagtat gggcaagcag ggagctagaa cgattcgcag ttaatcctgg cctgttagaa    6360
acatcagaag gctgtagaca atactgggga cagctacaac catcccttca gacaggatca    6420
gaagaactta gatcattata taatacagta gcaaccctct attgtgtgca tcaaaggata    6480
gagataaaag acaccaagga agctttagac aagatagagg aagagcaaaa caaaagtaag    6540
accaccgcac agcaagcggc cgctgatctt cagacctgga ggaggagata tgagggacaa    6600
ttggagaagt gaattatata aatataaagt agtaaaaatt gaaccattag gagtagcacc    6660
caccaaggca agagaagag tggtgcagag agaaaaaaga gcagtgggaa taggagcttt    6720
```

```
gttccttggg ttcttgggag cagcaggaag cactatgggc gcagcctcaa tgacgctgac    6780
ggtacaggcc agacaattat tgtctggtat agtgcagcag cagaacaatt tgctgagggc    6840
tattgaggcg caacagcatc tgttgcaact cacagtctgg ggcatcaagc agctccaggc    6900
aagaatcctg gctgtggaaa gatacctaaa ggatcaacag ctcctgggga tttggggttg    6960
ctctggaaaa ctcatttgca ccactgctgt gccttggaat gctagttgga gtaataaatc    7020 tctgaacag attggaatca cacgacctgg atggagtggg acagagaaat taacaattac    7080
acaagcttaa tacactcctt aattgaagaa tcgcaaaacc agcaagaaaa gaatgaacaa    7140
gaattattgg aattagataa atgggcaagt ttgtggaatt ggtttaacat aacaaattgg    7200
ctgtggtata taaaattatt cataatgata gtaggaggct tggtaggttt aagaatagtt    7260
tttgctgtac tttctatagt gaatagagtt aggcagggat attcaccatt atcgtttcag    7320
acccacctcc caaccccgag gggacccgac aggcccgaag gaatagaaga agaaggtgga    7380
gagagagaca gagacagatc cattcgatta gtgaacggat ctcgacggta tcgattagac    7440
tgtagcccag gaatatggca gctagattgt acacatttag aaggaaaagt tatcttggta    7500
gcagttcatg tagccagtgg atatatagaa gcagaagtaa ttccagcaga cagggcaa     7560 gaaacagcat acttcctctt aaaattagca ggaagatggc cagtaaaaac agtacataca    7620
gacaatggca gcaatttcac cagtactaca gttaaggccg cctgttggtg ggcggggatc    7680
aagcaggaat ttggcattcc ctacaatccc caaagtcaag gagtaataga atctatgaat    7740
aaagaattaa agaaaattat aggacaggta agagatcagg ctgaacatct taagacagca    7800
gtacaaatgg cagtattcat ccacaatttt aaaagaaaag ggggggattgg ggggtacagt    7860 gcagggggaaa gaatagtaga cataatagca acagacatac aaactaaaga attacaaaaa    7920
caaattacaa aaattcaaaa ttttcgggtt tattacaggg acagcagaga tccagtttgg    7980
ctgcatacgc gtcgtgaggc tccggtgccc gtcagtgggc agagcgcaca tcgcccacag    8040
tccccgagaa gttgggggga ggggtcggca attgaaccgg tgcctagaga aggtggcgcg    8100
gggtaaactg ggaaagtgat gtcgtgtact ggctccgcct ttttcccgag ggtgggggag    8160
aaccgtatat aagtgcagta gtcgccgtga acgttctttt tcgcaacggg tttgccgcca    8220
gaacacaggt aagtgccgtg tgtggttccc gcgggcctgg cctctttacg ggttatggcc    8280
cttgcgtgcc ttgaattact tccacctggc tgcagtacgt gattcttgat cccgagcttc    8340
gggttggaag tgggtgggag agttcgaggc cttgcgctta aggagcccct tcgcctcgtg    8400
cttgagttga ggcctggcct gggcgctggg ccgccgcgt gcgaatctgg tggcaccttc    8460
gcgcctgtct cgctgctttc gataagtctc tagccattta aattttttga tgacctgctg    8520
cgacgctttt tttctggcaa gatagtcttg taaatgcggg ccaagatctg cacactggta    8580
tttcggtttt tggggccgcg ggcggcgacg gggcccgtgc gtcccagcgc acatgttcgg    8640
cgaggcgggg cctgcgagcg cggccaccga gaatcggacg ggggtagtct caagctggcc    8700
ggcctgctct ggtgcctggc ctcgcgccgc cgtgtatcgc cccgccctgg gcggcaaggc    8760
tggcccggtc ggcaccagtt gcgtgagcgg aaagatggcc gcttccggc cctgctgcag    8820 ggagctcaaa atgaggacg cggcgctcgg gagagcgggg ggtgagtca cccacacaaa    8880 ggaaaagggc cttccgtcc tcagccgtcg cttcatgtga ctccacggag taccgggcgc    8940
cgtccaggca cctcgattag ttctcgagct tttggagtac gtcgtctttta ggttgggggg    9000 aggggtttta tgcgatggag tttccccaca ctgagtgggt ggagactgaa gttaggccag    9060
```

```
cttggcactt gatgtaattc tccttggaat ttgccctttt tgagtttgga tcttggttca    9120
ttctcaagcc tcagacagtg gttcaaagtt ttttcttcc atttcaggtg tcgtgagcta    9180
gctctagag                                                            9189
```

<210> SEQ ID NO 21
<211> LENGTH: 729
<212> TYPE: DNA
<213> ORGANISM: Artificial Sequence
<220> FEATURE:
<223> OTHER INFORMATION: Chemically Synthesized

<400> SEQUENCE: 21

```
cagctggtgg agtctggggg aggcttggta cagccagggc ggtccctgag actctcctgc     60
acaacttctg gattcacttt tggtgattat gctatgatct gggcccgcca ggctccaggg    120
aaggggctgg agtgggtctc atccattagt agtagtagta gttacatata ctacgcagac    180
tcagtgaagg gccgattcac catctccaga gacaacgcca agaactcact gtatctgcaa    240
atgaacagcc tgagagccga ggacacggct gtgtattact gtgcgagaga acgatacgat    300
ttttggagtg gaatggacgt ctggggcaaa gggaccacgg tcaccgtctc gagtggtgga    360
ggcggttcag gcggaggtgg ctctggcggt agtgcacagt ctgccctgac tcagcctgcc    420
tccgtgtctg ggtctcctgg acagtcgatc accatctcct gcactggaac cagcagtgat    480
gttgggagtt ataaccttgt ctcctggtac aacagcacc caggcaaagc ccccaaactc    540
atgatttatg agggcagtaa gcggccctca ggggtttcta atcgcttctc tggctccaag    600
tctggcaacg cggcctccct gacaatctct gggctccagg ctgaggacga ggctgattat    660
tactgccagt cctatgacag cagcctgagt gtggtattcg gcggagggac caagctgacc    720
gtcctaggt                                                            729
```

<210> SEQ ID NO 22
<211> LENGTH: 491
<212> TYPE: PRT
<213> ORGANISM: Artificial Sequence
<220> FEATURE:
<223> OTHER INFORMATION: Chemically Synthesized

<400> SEQUENCE: 22

```
Met Ala Leu Pro Val Thr Ala Leu Leu Leu Pro Leu Ala Leu Leu Leu
1               5                   10                  15

His Ala Ala Arg Pro Gly Ser Gln Leu Val Glu Ser Gly Gly Gly Leu
            20                  25                  30

Val Gln Pro Gly Arg Ser Leu Arg Leu Ser Cys Thr Thr Ser Gly Phe
        35                  40                  45

Thr Phe Gly Asp Tyr Ala Met Ile Trp Ala Arg Gln Ala Pro Gly Lys
    50                  55                  60

Gly Leu Glu Trp Val Ser Ser Ile Ser Ser Ser Ser Tyr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Glu Arg Tyr Asp Phe Trp Ser Gly Met
        115                 120                 125

Asp Val Trp Gly Lys Gly Thr Thr Val Thr Val Ser Ser Gly Gly Gly
    130                 135                 140
```

Gly Ser Gly Gly Gly Ser Gly Gly Ser Ala Gln Ser Ala Leu Thr
145                 150                 155                 160

Gln Pro Ala Ser Val Ser Gly Ser Pro Gly Gln Ser Ile Thr Ile Ser
            165                 170                 175

Cys Thr Gly Thr Ser Ser Asp Val Gly Ser Tyr Asn Leu Val Ser Trp
            180                 185                 190

Tyr Gln Gln His Pro Gly Lys Ala Pro Lys Leu Met Ile Tyr Glu Gly
        195                 200                 205

Ser Lys Arg Pro Ser Gly Val Ser Asn Arg Phe Ser Gly Ser Lys Ser
    210                 215                 220

Gly Asn Ala Ala Ser Leu Thr Ile Ser Gly Leu Gln Ala Glu Asp Glu
225                 230                 235                 240

Ala Asp Tyr Tyr Cys Gln Ser Tyr Asp Ser Ser Leu Ser Val Val Phe
            245                 250                 255

Gly Gly Gly Thr Lys Leu Thr Val Leu Gly Ala Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Lys Gln Gly Gln Asn Gln Leu Tyr
385                 390                 395                 400

Asn Glu Leu Asn Leu Gly Arg Arg Glu Glu Tyr Asp Val Leu Asp Lys
            405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
            485                 490

<210> SEQ ID NO 23
<211> LENGTH: 243
<212> TYPE: PRT
<213> ORGANISM: Artificial Sequence
<220> FEATURE:
<223> OTHER INFORMATION: Chemically Synthesized

<400> SEQUENCE: 23

Gln Leu Val Glu Ser Gly Gly Gly Leu Val Gln Pro Gly Arg Ser Leu
1               5                   10                  15

Arg Leu Ser Cys Thr Thr Ser Gly Phe Thr Phe Gly Asp Tyr Ala Met
                20                  25                  30

Ile Trp Ala Arg Gln Ala Pro Gly Lys Gly Leu Glu Trp Val Ser Ser
            35                  40                  45

Ile Ser Ser Ser Ser Tyr Ile Tyr Tyr Ala Asp Ser Val Lys Gly
    50                  55                  60

Arg Phe Thr Ile Ser Arg Asp Asn Ala Lys Asn Ser Leu Tyr Leu Gln
65                  70                  75                  80

Met Asn Ser Leu Arg Ala Glu Asp Thr Ala Val Tyr Tyr Cys Ala Arg
                85                  90                  95

Glu Arg Tyr Asp Phe Trp Ser Gly Met Asp Val Trp Gly Lys Gly Thr
            100                 105                 110

Thr Val Thr Val Ser Ser Gly Gly Gly Gly Ser Gly Gly Gly Gly Ser
            115                 120                 125

Gly Gly Ser Ala Gln Ser Ala Leu Thr Gln Pro Ala Ser Val Ser Gly
    130                 135                 140

Ser Pro Gly Gln Ser Ile Thr Ile Ser Cys Thr Gly Thr Ser Ser Asp
145                 150                 155                 160

Val Gly Ser Tyr Asn Leu Val Ser Trp Tyr Gln Gln His Pro Gly Lys
                165                 170                 175

Ala Pro Lys Leu Met Ile Tyr Glu Gly Ser Lys Arg Pro Ser Gly Val
            180                 185                 190

Ser Asn Arg Phe Ser Gly Ser Lys Ser Gly Asn Ala Ala Ser Leu Thr
            195                 200                 205

Ile Ser Gly Leu Gln Ala Glu Asp Glu Ala Asp Tyr Tyr Cys Gln Ser
    210                 215                 220

Tyr Asp Ser Ser Leu Ser Val Val Phe Gly Gly Gly Thr Lys Leu Thr
225                 230                 235                 240

Val Leu Gly

<210> SEQ ID NO 24
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 24
gcgggatcct ctagagcggc ccagccggcc atggcccagg tg                          42

<210> SEQ ID NO 25
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 25
gcggctagcg gccgcccgtt ttatttccaa ctttgtcccc cc                          42

<210> SEQ ID NO 26
<211> LENGTH: 53
<212> TYPE: DNA
<213> ORGANISM: Artificial Sequence
<220> FEATURE:
<223> OTHER INFORMATION: Chemically Synthesized

<400> SEQUENCE: 26
gctgggacaa agttggaaat caaagctagc accacgacgc cagcgccgcg acc              53

```
<210> SEQ ID NO 27
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 27
tcgacagtcg acttagcgag ggggcagggc ct                           32

<210> SEQ ID NO 28
<211> LENGTH: 60
<212> TYPE: DNA
<213> ORGANISM: Artificial Sequence
<220> FEATURE:
<223> OTHER INFORMATION: Chemically Synthesized

<400> SEQUENCE: 28
atagcatcta gaatggcctt accagtgacc gccttgctcc tgccgctggc cttgctgctc   60

<210> SEQ ID NO 29
<211> LENGTH: 32
<212> TYPE: DNA
<213> ORGANISM: Artificial Sequence
<220> FEATURE:
<223> OTHER INFORMATION: Chemically Synthesized

<400> SEQUENCE: 29
tcgacagtcg acttagcgag ggggcagggc ct                           32
```

COMPOSITIONS AND METHODS FOR TREATING CANCER

CROSS-REFERENCE TO RELATED APPLICATION

The present application is a continuation application of, and claims priority to, U.S. patent application Ser. No. 15/212,916, filed Jul. 18, 2016, now issued as U.S. Pat. No. 10,457,729, which is a continuation of U.S. patent application Ser. No. 13/979,927, filed Nov. 1, 2013, issued as U.S. Pat. No. 9,402,865, a U.S. national phase application filed under 35 U.S.C. § 371 claiming benefit to International Patent Application No. PCT/US2012/021738, filed on Jan. 18, 2012, which is entitled to priority under 35 U.S.C. § 119(e) to U.S. Provisional Patent Application No. 61/433,731, filed on Jan. 18, 2011, each of which application is hereby incorporated herein by reference in its entirety.

BACKGROUND OF THE INVENTION

Ovarian cancer is responsible for the majority of gynecologic cancer deaths. In 2004, in the United States, 25,580 new cases were diagnosed and 16,090 women died of ovarian cancer.

The disease is more common in industrialized nations, with the exception of Japan. In the United States, females have a 1.4% to 2.5% (1 out of 40-60 women) lifetime chance of developing ovarian cancer. Older women are at highest risk.

Although intraperitoneal chemotherapy has been recommended as a standard of care for the first-line treatment of ovarian cancer, the basis for this recommendation has been challenged. Radiation therapy is not effective for advanced stages because when vital organs are in the radiation field, a high dose cannot be safely delivered. Surgical therapy is also not also effective.

Despite the initial successful multimodality therapy with cytoreductive surgery and subsequent combination chemotherapy, most patients with advanced disease will ultimately relapse and become incurable. For this reason, novel therapeutic approaches for the treatment of this malignancy are urgently needed.

Ovarian cancer in particular appears to be suited to adoptive transfer approach based on the fact that the ovarian tumors are relatively immunogenic, inducing an endogenous T cell response.

Accordingly, there exists a need for improved therapeutic modalities to provide anti-tumor immunity, and thereby treat ovarian and other cancers.

SUMMARY OF THE INVENTION

The present invention provides an isolated nucleic acid sequence encoding a chimeric antigen receptor (CAR), wherein the isolated nucleic acid sequence comprises the nucleic acid sequence of α-folate receptor (FRα) binding domain and the nucleic acid sequence of 4-1BB (CD137) costimulatory domain.

In one embodiment, the nucleic acid sequence further comprises the nucleic acid sequence of CD3 zeta binding domain.

In one embodiment, the CAR comprises the amino acid sequence of SEQ ID NO: 13 or SEQ ID NO: 22.

In one embodiment, the isolated nucleic acid sequence encoding the CAR comprises the nucleic acid sequence of SEQ ID NO: 1 or SEQ ID NO: 20.

In one embodiment the FRα binding domain is an antibody or a FRα-binding fragment thereof. Preferably, the FRα binding domain is a Fab or a scFV.

In one embodiment, the FRα binding domain binds to a tumor antigen, wherein the tumor antigen is FRα. In one embodiment, the tumor antigen is associated with an epithelial malignancy. In another embodiment, the tumor antigen is associated with a solid tumor.

In one embodiment, the FRα binding domain comprises the amino acid sequence of SEQ ID NO: 15 or SEQ ID NO: 23.

In one embodiment, the FRα binding domain is encoded by the nucleic acid sequence of SEQ ID NO: 3 or SEQ ID NO: 21.

In one embodiment, the 4-1BB costimulatory domain comprises the amino acid sequence of SEQ ID NO: 18.

In one embodiment, the 4-1BB costimulatory domain is encoded by the nucleic acid sequence of SEQ ID NO: 6.

In one embodiment, the CD3 zeta signaling domain comprises the amino acid sequence of SEQ ID NO: 19.

In one embodiment, the CD3 zeta signaling domain is encoded by the nucleic acid sequence of SEQ ID NO: 7.

In one embodiment, the isolated nucleic acid sequence further comprises the nucleic acid sequence of a transmembrane domain.

The invention also provides an isolated CAR comprising a FRα binding domain and a 4-1BB costimulatory domain.

The invention also provides a genetically modified T cell comprising an isolated nucleic acid sequence encoding a CAR, wherein the isolated nucleic acid sequence comprises the nucleic acid sequence of a FRα binding domain and the nucleic acid sequence of a 4-1BB costimulatory domain.

The invention also provides a vector comprising an isolated nucleic acid sequence encoding a CAR, wherein the isolated nucleic acid sequence comprises the nucleic acid sequence of a FRα binding domain and the nucleic acid sequence of a 4-1BB costimulatory domain.

The invention also provides a method for providing anti-tumor immunity in a subject. In one embodiment comprises administering to the subject an effective amount of a genetically modified T cell comprising an isolated nucleic acid sequence encoding a CAR, wherein the isolated nucleic acid sequence comprises the nucleic acid sequence of a FRα binding domain and the nucleic acid sequence of a 4-1BB costimulatory domain, thereby providing anti-tumor immunity in the subject. In one embodiment, the isolated nucleic acid sequence further comprises the nucleic acid sequence of a CD3 zeta signaling domain.

In one embodiment, the presence of the costimulatory domain enhances T cell survival. In another embodiment, the presence of the costimulatory domain increases the efficacy of anti-tumor immunity in a subject.

In one embodiment, the subject is a mammal. Preferably, the subject is a human.

The invention also provides a method for stimulating a T cell-mediated immune response to a cell population or tissue in a subject. In one embodiment, the method comprises administering to the subject an effective amount of a genetically modified T cell comprising an isolated nucleic acid sequence encoding a CAR, wherein the isolated nucleic acid sequence comprises the nucleic acid sequence of a FRα binding domain and the nucleic acid sequence of a 4-1BB costimulatory domain, thereby stimulating a T cell-mediated immune response in a subject.

The invention also provides a method for treating ovarian cancer in a subject. In one embodiment, the method comprises administering to the subject an effective amount of a genetically modified T cell comprising an isolated nucleic acid sequence encoding a CAR, wherein the isolated nucleic acid sequence comprises the nucleic acid sequence of a FRα binding domain and the nucleic acid sequence of a 4-1BB costimulatory domain, thereby treating the ovarian cancer in the subject.

The invention also provides a method for treating cancer in a subject. In one embodiment, the method comprises administering to the subject an effective amount of a genetically modified T cell comprising an isolated nucleic acid sequence encoding a CAR, wherein the isolated nucleic acid sequence comprises the nucleic acid sequence of a FRα binding domain and the nucleic acid sequence of a 4-1BB costimulatory domain, thereby treating cancer in the subject.

The invention also provides a method of generating a persisting population of genetically engineered T cells in a subject diagnosed with ovarian cancer. In one embodiment, the method comprises administering to the subject an effective amount of a genetically modified T cell comprising an isolated nucleic acid sequence encoding a CAR, wherein the isolated nucleic acid sequence comprises the nucleic acid sequence of a FRα binding domain and the nucleic acid sequence of a 4-1BB costimulatory domain, wherein the persisting population of genetically engineered T cells persists in the subject for at least one month after administration. In one embodiment, the persisting population of genetically engineered T cells persists for at least three months after administration.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 5A shows a representative experimental model. FIG. 5B is a chart depicting tumor volume. FIG. 5C is a series of images depicting tumor growth. FIG. 5D is a chart depicting tumor volume. FIG. 5E is a chart depicting cell counts for CD4 and CD8 T cells.

FIG. 8A shows a schematic representation of the αFR-binding chimeric receptors. A binding-control chimeric receptor with a truncated TCRζ domain and a specificity control receptor with an anti-CD19 scFv were also constructed. FIG. 8B is an image showing expression of the αFR-CAR proteins was examined on human primary CD4 T cells. Transduction efficiencies are determined by flow cytometry.

FIGS. 12A and 12C demonstrate that mice subcutaneously injected with $3\times10^6$ SKOV3 cells were monitored for tumor growth until reaching tumor volume of 200~300 mm$^3$. Tumor-bearing mice were treated with intra-tumoral injections of $20\times10^6$ T cells (~40%-50% transgene positive) on day 40 and 45. FIGS. 12B and 12D demonstrate that SKOV3-bearing NOG mice were treated with T lymphocytes expressing the BBz chimeric receptors via IT, IP, and IV routes and the effect on tumor growth was assessed.

FIGS. 14A-14C are a series of graphs and images showing that αFR CAR BBz eradication of SKOV3 tumor is antigen-specific. FIGS. 14A and 14B show SKOV3 bearing mice treated with lymphocytes expressing the BBz CAR (against αFR or CD19) and GFP on day 40 and 45. FIG. 14C shows peripheral blood from SKOV3-bearing NOG mice was obtained 3 weeks after second time T cells injection and quantified for the presence of CD4 and CD8 T cells by a FACS Trucount assay.

FIG. 15A is an image showing i.p. injection of SKOV3 tumors in NOG mice results in abdominal distension and nodular peritoneal tumors following CD19 CAR T cells treatment. Mice developed ascites as evidenced by a distended abdomen (middle) when compared with a mouse (left) treated with FR CAR BBz T cells, postmortem visualization of the peritoneum shows nodular tumor masses (arrows) within the abdominal cavity (right). FIGS. 15B and 15C show i.p./i.v. injection of αFR CAR BBz T cells delays tumor progression and ascites formation, and improves survival. Kaplan-Meier survival curve of NOG mice treated with either CD19 CAR or αFR CART cells.

FIG. 18A shows schematic representation of MOv19-based CAR constructs containing the CD3ζ cytosolic domain alone (MOv19-ζ) or in combination with CD137 costimulatory module (MOv19-BBζ). FRα-specific CAR with a truncated CD3ζ domain (MOv19-Δζ) and anti-CD19-BBζ CAR are shown. VL, variable L chain; L, linker; VH, variable H chain; TM, transmembrane region. FIG. 18B depicts MOv19 CAR expression (solid black line) on human CD3-gated cells after transduction with lentivirus compared with parallel untransduced T cells (filled gray histograms). Percent transduction is indicated. FIG. 18C depicts surface FRα expression (solid black line) by various human ovarian cancer cell lines by flow cytometry; isotype antibody control (filled gray histograms). FIG. 18D depicts antigen-specific IFN-γ secretion by MOv19-ζ and MOv19-BBζ CAR-transduced T cells but not MOv19-Δζ anti-CD19-BBζ T cells, following overnight incubation with FRα$^+$ cancer cell lines. Mean IFN-γ concentration±SEM (pg/mL) from triplicate cultures is shown. FIG. 18E depicts antigen-specific killing of FRα$^+$ tumor cells by FRα CAR$^+$ CD8$^+$ T cells in 18-hour bioluminescence assay at the indicated E/T ratio. Untransduced T cells (UNT) or gfp-transduced human CD8$^+$ T cells served as controls.

FIG. 19A depicts tumor growth, as assessed by caliper measurement [V=½(length×width)]. FIG. 19B shows that SKOV3 fLuc$^+$ bioluminescence signal was decreased in MOv19-BBζ CAR treated mice compared with the MOv19-ζ and the control treatment groups 2 weeks and 4 weeks after last T-cell dose. SKOV3 fLuc-bearing NSG mice were treated with 8×10$^6$ MOv19-BBζ T cells via i.t., i.p., or i.v. routes. FIG. 19C depicts tumor growth, as assessed by caliper measurement. FIG. 19D shows that CD137 signaling enhances the survival of human CD4$^+$ and CD8$^+$ T cells in vivo on day 73 (4 weeks following last T-cell dose) in the peripheral blood. CD4 and CD8 T cells were quantitated from blood by using the TruCount method. Mean cell concentration (cells/μL)±SD for all evaluable mice in each treatment group is shown.

FIG. 20A depicts measurements of tumor volume by calipers every 2 to 3 days. Peripheral blood was collected 3 weeks following last T-cell infusion. FIG. 20B depicts the absolute number of human CD4$^+$ and CD8$^+$ T cells/μl of blood. Mean cell count±SD is shown. FIG. 20C depicts FRα- and CD19-specific CAR expression on human CD3$^+$ T cells from peripheral blood of treated mice measured by flow cytometry by using goat anti-mouse IgG F(ab')$_2$. Mean CAR$^+$ expression frequency±SD per group is shown. FIG. 20D depicts absolute CAR$^+$ T-cell count, calculated as number of human CD3$^+$ T cells/μL of blood multiplied by percent CAR$^+$. Mean count±SD was determined.

FIG. 22A depicts NSG mice which received i.p. injection of 5×10$^6$ SKOV3 fLuc$^+$ tumor cells and were randomized into 4 groups before beginning therapy with 9×10$^6$ T cells expressing MOv19-BBζ or anti-CD19-BBζ via i.p. or i.v. infusion on day 30 and 35 after tumor inoculation. FIG. 22B depicts representative NSG mice treated with MOv19-BBζ T cells (left) via i.v. (top) or i.p (bottom) infusion. Mice treated with anti-CD19-BBζ T cells (right) developed ascites as evidenced by a distended abdomen (middle). Postmortem visualization of the peritoneum shows nodular tumor masses (arrows; far right). FIG. 22C depicts Kaplan-Meier tumor-related survival curve of tumor-bearing NSG mice treated with either MOv19-BBζ or anti-CD19-BBζ T cells via i.v. or i.p. injection. FIG. 22D depicts Kaplan-Meier overall survival of tumor-bearing NSG mice.

FIG. 23A depicts tumors, as monitored by BLI. FIG. 23B depicts quantified mean±SD bioluminescence signal photon emission from fLuc$^+$ tumor cells.

FIG. 25A depicts that the native mouse malignant mesothelioma cell line AE17 which does not express human FRα was transduced to express high surface levels of human FRα (AE17.FRα) as shown by flow cytometry. Primary human T cells transduced to express either MOv19-ζ, MOv19-BBζ, MOv19-Δζ, or anti-CD19-BBζ CARs, or green fluorescent protein (gfp) were co-cultured with Cr51-labeled native AE17 or AE17.FRα cell lines for 4 hrs at the indicated effector to target ratio. FIG. 25B depicts the percent specific target cell lysis, calculated as (experimental−spontaneous release)÷(maximal−spontaneous release) times 100. Results are expressed as mean of triplicate wells with error bars indicating standard deviation. Human T cells transduced to express MOv19-ζ, MOv19-BBζ, MOv19-Δζ, or anti-CD19-BBζ CAR were co-cultured at various effector to target ratios for 24 hrs with gfp expressing AE17 or AE17.FRα cells. FIG. 25C depicts transduced cells photographed under fluorescent microscopy. Target cell lysis is indicated by imaging reduction in gfp-labeled adherent tumor cells.

FIG. 26A depicts tumor burden, as measured by averaged bioluminescent signal, per treatment group 4 weeks following T cell infusion. FIG. 26B depicts the persistence of T lymphocytes in vivo assessed 4 weeks after transfer of T cells expressing MOv9-BBζ delivered via i.v., i.t., or i.p. routes of administration or i.t. administration of T cells expressing MOv19-ζ, or control vectors (MOv19-Δζ or gfp; controls) by Trucount method. FIG. 26C shows that four weeks after T cell therapy, the stable persistence of engineered human T cells (x-axis) is negative correlated with the bioluminescent signal (y-axis; r=−0.78). Bcl-$X_L$ expression by FR-specific CAR CD8 T cells was examined after 3 days of culture in media alone (not shown) or with SKOV3. Bcl-$X_L$ expression was preferentially increased in MOv19-BBζ CAR T cells populations (15.4%), compared with MOv19-ζ CAR+ T cells (6.7%) after stimulation with FRα+ tumor cells. Culture in media alone did not induce Bcl-XL expression in CAR T cells. FIG. 26D depicts representative FACS analysis for one of three independent co-cultures.

FIG. 30 is a table summarizing the identity of the SEQ ID NOs.

DETAILED DESCRIPTION OF THE INVENTION

Figure 1A:
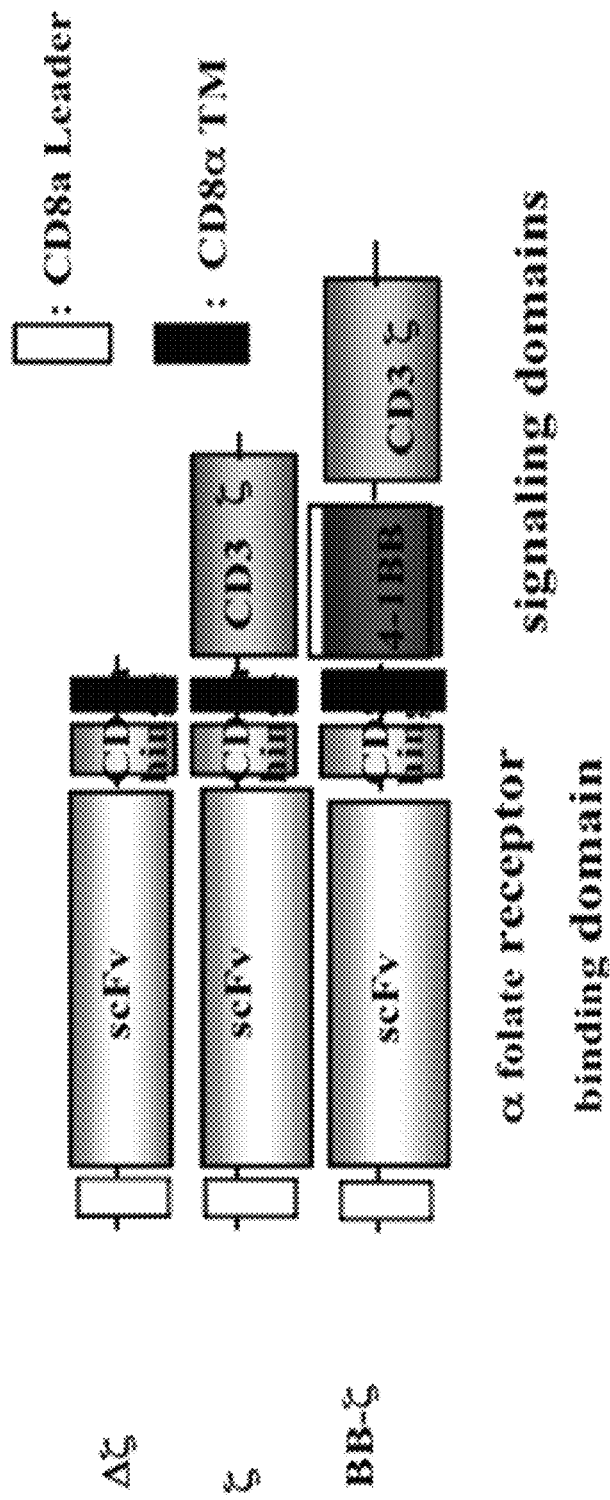
FIGS. 1A-1B are a set of images showing the construction and lentiviral gene transfer of αFR CARS to human T cells.
Figure 1B:
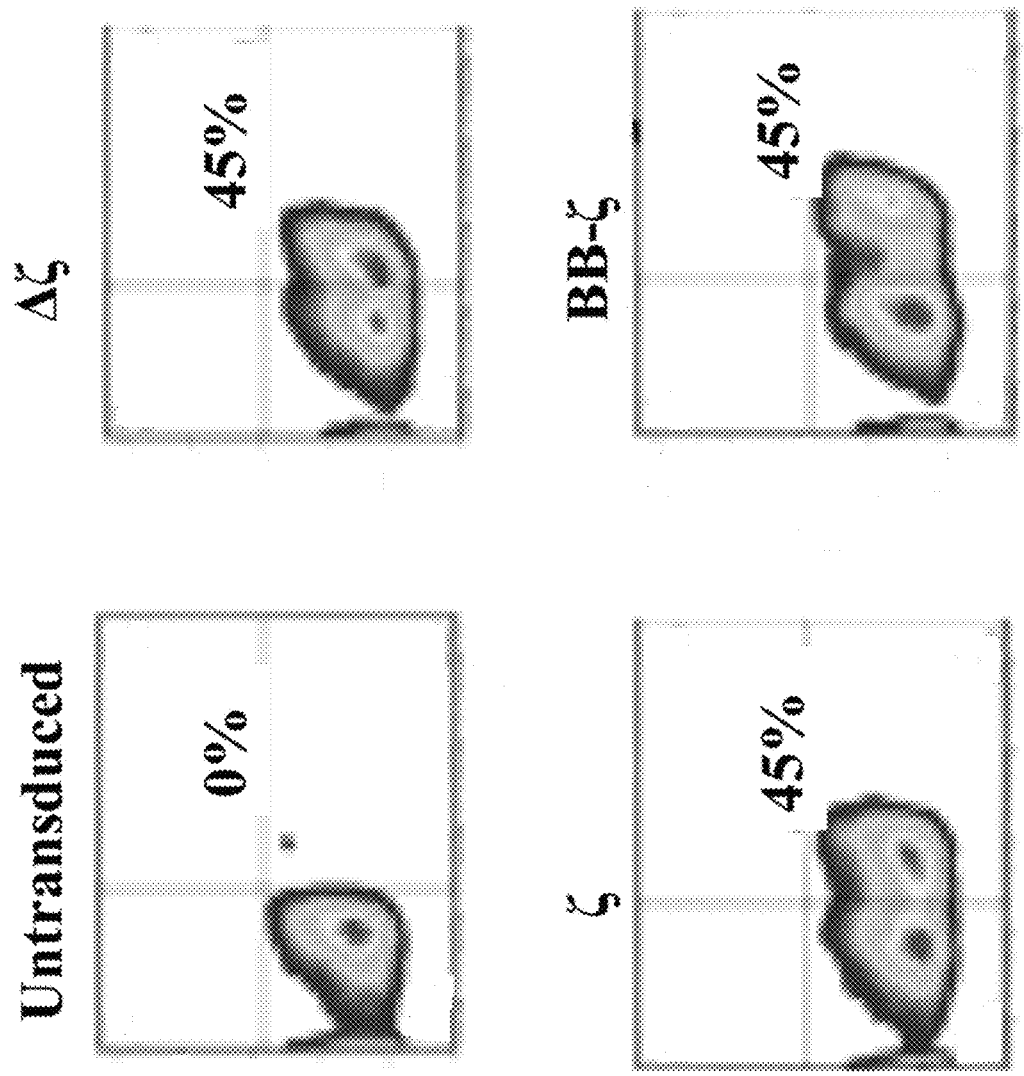
Figures 2A, 2B, 2C:
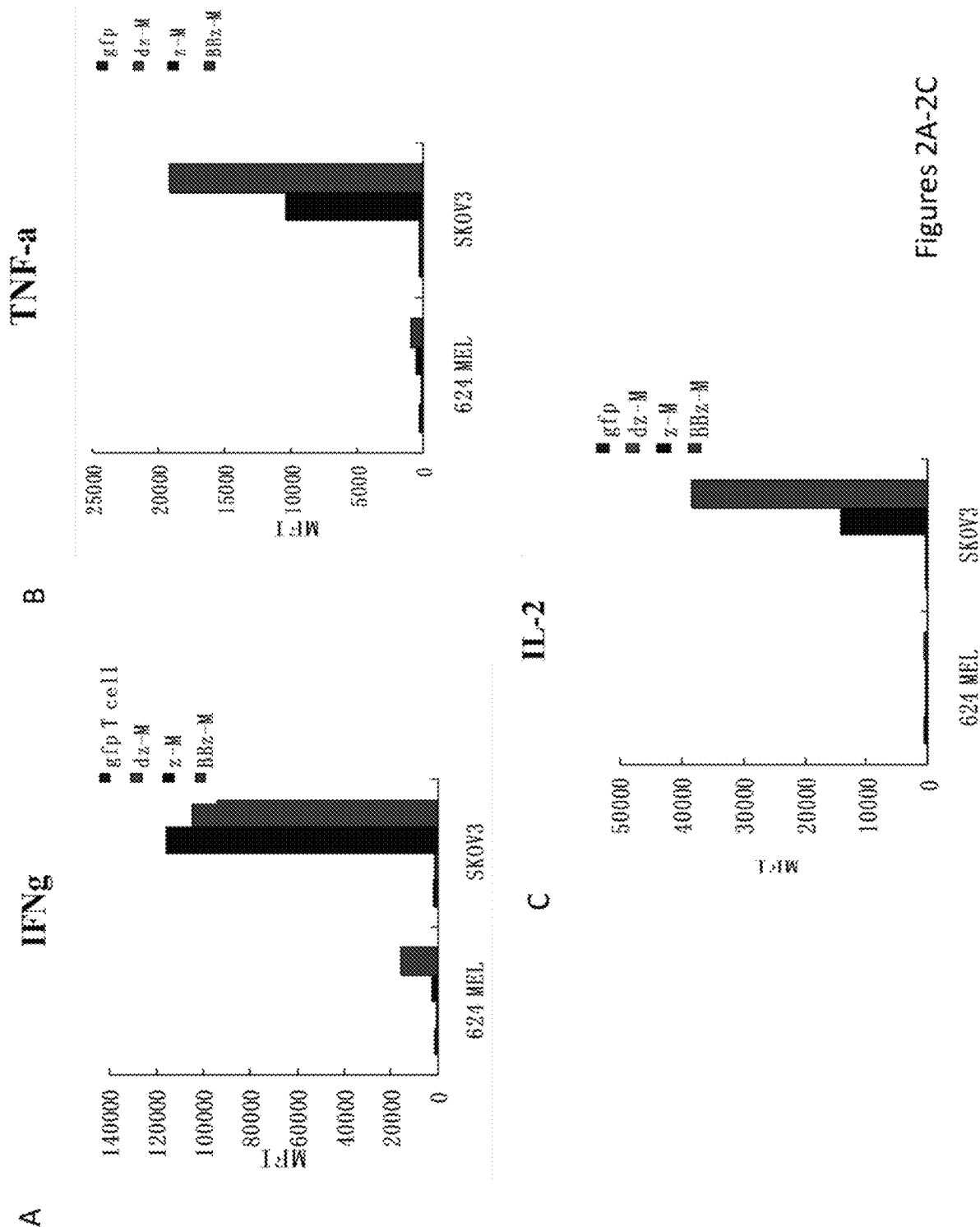
FIGS. 2A-2C are a series of graphs demonstrating that CAR+ T cells preferentially secreted Th1 cytokines.

The invention relates to compositions and methods for treating cancer including but not limited to epithelial cancers. The present invention relates to a strategy of adoptive cell transfer of T cells transduced to express a chimeric antigen receptor (CAR). CARs are molecules that combine antibody-based specificity for a desired antigen (e.g., tumor antigen) with a T cell receptor-activating intracellular domain to generate a chimeric protein that exhibits a specific anti-tumor cellular immune activity.

The present invention relates generally to the use of T cells genetically modified to stably express a desired CAR. T cells expressing a CAR are referred to herein as CAR T cells or CAR modified T cells. Preferably, the cell can be genetically modified to stably express an antibody binding domain on its surface, conferring novel antigen specificity that is MHC independent. In some instances, the T cell is genetically modified to stably express a CAR that combines an antigen recognition domain of a specific antibody with an intracellular domain of the CD3-zeta chain or FcγRI protein into a single chimeric protein.

In one embodiment, the CAR of the invention comprises an extracellular domain having an antigen recognition domain, a transmembrane domain, and a cytoplasmic domain. In one embodiment, the transmembrane domain that naturally is associated with one of the domains in the CAR is used. In another embodiment, the transmembrane domain can be selected or modified by amino acid substitution to avoid binding of such domains to the transmembrane domains of the same or different surface membrane proteins to minimize interactions with other members of the receptor complex. Preferably, the transmembrane domain is the CD8α hinge domain.

With respect to the cytoplasmic domain, the CAR of the invention can be designed to comprise the CD28 and/or 4-1BB (CD137) signaling domain by itself or be combined with any other desired cytoplasmic domain(s) useful in the context of the CAR of the invention. In one embodiment, the cytoplasmic domain of the CAR can be designed to further comprise the signaling domain of CD3-zeta. For example, the cytoplasmic domain of the CAR can include but is not limited to CD3-zeta, 4-1BB and CD28 signaling modules and combinations thereof. Accordingly, the invention provides CAR T cells and methods of their use for adoptive therapy.

In one embodiment, the CAR T cells of the invention can be generated by introducing a lentiviral vector comprising a desired CAR targeting the α-folate receptor (αFR or FRα) into the cells. For example, the lentiviral vector comprises a CAR comprising anti-FRα, CD8α hinge and transmembrane domain, and human 4-1BB and CD3zeta signaling domains, into the cells. The anti-FRα domain of the CAR of the invention can be any domain that binds to FRα including but not limited to monoclonal antibodies, polyclonal antibodies, antibody fragments, and humanized antibodies. Therefore, as used herein, anti-FRα (or anti-αFR) refers to any composition targeted to FRα. The CAR T cells of the invention are able to replicate in vivo resulting in long-term persistence that can lead to sustained tumor control.

In one embodiment the invention relates to administering a genetically modified T cell expressing a CAR for the treatment of a patient having cancer or at risk of having cancer using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

The invention includes using T cells expressing an anti-FRα CAR including both CD3-zeta and the 4-1BB costimulatory domain (also referred to as FRα-specific CAR T cells). The FRα-specific CAR T cells of the invention can undergo robust in vivo T cell expansion and can establish FRα-specific memory cells that persist at high levels for an extended amount of time in blood and bone marrow. In some instances, the FRα-specific CAR T cells of the invention infused into a patient can eliminate cancerous cells in vivo in patients with epithelial ovarian cancer. However, the invention is not limited to FRα-specific CAR T cells. Rather, the invention includes any antigen binding moiety fused with one or more intracellular domains selected from the group of a CD137 (4-1BB) signaling domain, a CD28 signaling domain, a CD3zeta signal domain, and any combination thereof.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "FRα binding domain" may refer to any FRα specific binding domain, known to one of skilled in the art. In one example, FRα binding domain comprises a single-chain variable fragment (scFv) comprising the variable regions of the heavy ($V_H$) and light chains ($V_L$) of an antibody binding specifically to FRα. Anti-FRα antibodies, antibody fragments, and their variants are well known in the art and fully described in U.S. Patent Publications U.S 20100055034; U.S. 20090324594; U.S. 20090274697; U.S. 20080260812; U.S. 20060239910; U.S. 20050232919; U.S. 20040235108, all of which are incorporated by reference herein in their entirety. In one embodiment, the FRα binding domain is a homologue, a variant, an isomer, or a functional fragment of an anti-FRα antibody. Each possibility represents a separate embodiment of the present invention.

As used herein, the terms "4-1BB (CD137) costimulatory domain" may refer to any sequence of 4-1BB including, for example, a stimulatory signaling domain of 4-1BB. Stimulatory signaling domains of 4-1BB and their variants are well known in the art and fully described in U.S. Patent Publication 20050113564, which is incorporated by reference herein in its entirety. Nucleic acid and amino acid sequences of 4-1BB and their variants are well known in the art and fully described in U.S. Patent Publications U.S. 20060063923; U.S. 20060029595; U.S. 20030082157; U.S. 20020168719; U.S. 20040091476; U.S. 20050113564; and U.S. 20060002904, all of which are incorporated by reference herein in their entirety. In one embodiment, the 4-1BB (CD137) costimulatory domain is a homologue, a variant, an isomer, or a functional fragment of 4-1BB (CD137). Each possibility represents a separate embodiment of the present invention.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')$_2$, and Fv fragments, linear antibodies, scFv antibodies, and multispecific antibodies formed from antibody fragments. An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for treating cancer among other diseases. The cancer may be a hematological malignancy, a solid tumor, a primary or a metastasizing tumor. Preferably, the cancer is an epithelial cancer, or in other words, a carcinoma. More preferably, the cancer is epithelial ovarian cancer. Other diseases treatable using the compositions and methods of the invention include viral, bacterial and parasitic infections as well as autoimmune diseases.

In one embodiment, the invention provides a cell (e.g., T cell) engineered to express a CAR wherein the CAR T cell exhibits an antitumor property. The CAR of the invention can be engineered to comprise an extracellular domain having an antigen binding domain fused to an intracellular signaling domain of the T cell antigen receptor complex zeta chain (e.g., CD3 zeta). The CAR of the invention when expressed in a T cell is able to redirect antigen recognition based on the antigen binding specificity. An exemplary antigen is FRα because this antigen is expressed on malignant epithelial cells. However, the invention is not limited to targeting FRα. Rather, the invention includes any antigen binding moiety that when bound to its cognate antigen, affects a tumor cell so that the tumor cell fails to grow, is prompted to die, or otherwise is affected so that the tumor burden in a patient is diminished or eliminated. The antigen binding moiety is preferably fused with an intracellular domain from one or more of a costimulatory molecule and a zeta chain. Preferably, the antigen binding moiety is fused with one or more intracellular domains selected from the group of a CD137 (4-1BB) signaling domain, a CD28 signaling domain, a CD3zeta signal domain, and any combination thereof.

In one embodiment, the CAR of the invention comprises a CD137 (4-1BB) signaling domain. This is because the present invention is partly based on the discovery that CAR-mediated T-cell responses can be further enhanced with the addition of costimulatory domains. For example, inclusion of the CD137 (4-1BB) signaling domain significantly increased anti-tumor activity and in vivo persistence of CAR T cells compared to an otherwise identical CAR T cell not engineered to express CD137 (4-1BB).

Composition

The present invention provides chimeric antigen receptor (CAR) comprising an extracellular and intracellular domain. The extracellular domain comprises a target-specific binding element otherwise referred to as an antigen binding moiety. The intracellular domain or otherwise the cytoplasmic domain comprises, a costimulatory signaling region and a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding moiety that specifically binds to an antigen on a tumor cell. In the context of the present invention, "tumor antigen" or "hyperproliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding moiety of the invention will depend on the particular type of cancer to be treated. Tumor antigens are well known in the art and include, for example, a glioma-associated antigen, carcinoembryonic antigen (CEA), (3-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/ MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BC A225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding moiety portion of the CAR targets an antigen that includes but is not limited to FRα, CD24, CD44, CD133, CD166, epCAM, CA-125, HE4, Oval, estrogen receptor, progesterone receptor, HER-2/neu, uPA, PAI-1, and the like.

Depending on the desired antigen to be targeted, the CAR of the invention can be engineered to include the appropriate antigen bind moiety that is specific to the desired antigen target. For example, if FRα is the desired antigen that is to be targeted, an antibody for FRα can be used as the antigen bind moiety for incorporation into the CAR of the invention.

In one embodiment, the antigen binding moiety portion of the CAR of the invention targets FRα. Preferably, the antigen binding moiety portion in the CAR of the invention is anti-FRα scFV, wherein the nucleic acid sequence of the anti-FRα scFV comprises the sequence set forth in SEQ ID: 3. In one embodiment, the anti-FRα scFV comprise the nucleic acid sequence that encodes the amino acid sequence of SEQ ID NO: 15. In another embodiment, the anti-FRα scFV portion of the CAR of the invention comprises the amino acid sequence set forth in SEQ ID NO: 15.

In one embodiment, the antigen binding moiety portion in the CAR of the invention is a humanized anti-FRα scFV, wherein the nucleic acid sequence of the humanized anti-FRα scFV comprises the sequence set forth in SEQ ID: 21. In one embodiment, the humanized anti-FRα scFV comprise the nucleic acid sequence that encodes the amino acid sequence of SEQ ID NO: 23. In another embodiment, the humanized anti-FRα scFV portion of the CAR of the invention comprises the amino acid sequence set forth in SEQ ID NO: 23.

Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Preferably, the transmembrane domain in the CAR of the invention is the CD8 transmembrane domain. In one embodiment, the CD8 transmembrane domain comprises the nucleic acid sequence of SEQ ID NO: 5. In one embodiment, the CD8 transmembrane domain comprises the nucleic acid sequence that encodes the amino acid sequence of SEQ ID NO: 17. In another embodiment, the CD8 transmembrane domain comprises the amino acid sequence of SEQ ID NO: 17.

In some instances, the transmembrane domain of the CAR of the invention comprises the CD8 hinge domain. In one embodiment, the CD8 hinge domain comprises the nucleic acid sequence of SEQ ID NO: 4. In one embodiment, the CD8 hinge domain comprises the nucleic acid sequence that encodes the amino acid sequence of SEQ ID NO: 16. In another embodiment, the CD8 hinge domain comprises the amino acid sequence of SEQ ID NO: 16.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3 zeta.

In a preferred embodiment, the cytoplasmic domain of the CAR can be designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB. In yet another embodiment, the cytoplasmic domain is designed to comprise the signaling domain of CD3-zeta and the signaling domain of CD28 and 4-1BB.

In one embodiment, the cytoplasmic domain in the CAR of the invention is designed to comprise the signaling domain of 4-1BB and the signaling domain of CD3-zeta, wherein the signaling domain of 4-1BB comprises the nucleic acid sequence set forth in SEQ ID NO: 6 and the signaling domain of CD3-zeta comprises the nucleic acid sequence set forth in SEQ ID NO: 7.

In one embodiment, the cytoplasmic domain in the CAR of the invention is designed to comprise the signaling domain of 4-1BB and the signaling domain of CD3-zeta, wherein the signaling domain of 4-1BB comprises the nucleic acid sequence that encodes the amino acid sequence of SEQ ID NO: 18 and the signaling domain of CD3-zeta comprises the nucleic acid sequence that encodes the amino acid sequence of SEQ ID NO: 19.

In one embodiment, the cytoplasmic domain in the CAR of the invention is designed to comprise the signaling domain of 4-1BB and the signaling domain of CD3-zeta, wherein the signaling domain of 4-1BB comprises the amino acid sequence set forth in SEQ ID NO: 18 and the signaling domain of CD3-zeta comprises the amino acid sequence set forth in SEQ ID NO: 19.

Vectors

The present invention encompasses a DNA construct comprising sequences of a CAR, wherein the sequence comprises the nucleic acid sequence of an antigen binding moiety operably linked to the nucleic acid sequence of an intracellular domain. An exemplary intracellular domain that can be used in the CAR of the invention includes but is not limited to the intracellular domain of CD3-zeta, CD28, 4-1BB, and the like. In some instances, the CAR can comprise any combination of CD3-zeta, CD28, 4-1BB, and the like.

In one embodiment, the CAR of the invention comprises anti-FRα scFv, human CD8 hinge and transmembrane domain, and human 4-1BB and CD3zeta signaling domains. In one embodiment, the CAR of the invention comprises the nucleic acid sequence set forth in SEQ ID NO: 1. In another embodiment, the CAR of the invention comprises the nucleic acid sequence that encodes the amino acid sequence of SEQ ID NO: 13. In another embodiment, the CAR of the invention comprises the amino acid sequence set forth in SEQ ID NO: 13.

In one embodiment, the CAR of the invention comprises humanized anti-FRα scFv, human CD8 hinge and transmembrane domain, and human 4-1BB and CD3zeta signaling domains. In one embodiment, the CAR of the invention comprises the nucleic acid sequence set forth in SEQ ID NO: 20. In another embodiment, the CAR of the invention comprises the nucleic acid sequence that encodes the amino acid sequence of SEQ ID NO: 22. In another embodiment, the CAR of the invention comprises the amino acid sequence set forth in SEQ ID NO: 22.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots)

or by assays described herein to identify agents falling within the scope of the invention.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, IL-10, IL-12, IL-15, TGF$\beta$, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) transduced with a lentiviral vector (LV). For example, the LV encodes a CAR that combines an antigen recognition domain of a specific antibody with an intracellular domain of CD3-zeta, CD28, 4-1BB, or any combinations thereof. Therefore, in some instances, the transduced T cell can elicit a CAR-mediated T-cell response.

The invention provides the use of a CAR to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a CAR, wherein the CAR comprises a binding moiety that specifically interacts with a predetermined target, a zeta chain portion comprising for example the intracellular domain of human CD3zeta, and a costimulatory signaling region.

In one embodiment, the present invention includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control.

In one embodiment, the CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, it was unexpected that the FR$\alpha$-specific CAR T cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the CAR-modified T cells may be an active or a passive immune response. In addition, the CAR mediated immune response may be part of an adoptive immunotherapy approach in which CAR-modified T cells induce an immune response specific to the antigen binding moiety in the CAR. For example, FRα-specific CAR T cells elicit an immune response specific against cells expressing FRα.

While the data disclosed herein specifically disclose lentiviral vector comprising anti-FRα scFv, human CD8α hinge and transmembrane domain, and human 4-1BB and CD3zeta signaling domains, the invention should be construed to include any number of variations for each of the components of the construct as described elsewhere herein. That is, the invention includes the use of any antigen binding moiety in the CAR to generate a CAR-mediated T-cell response specific to the antigen binding moiety. For example, the antigen binding moiety in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

In one embodiment, the antigen bind moiety portion of the CAR of the invention is designed to treat a particular cancer. FRα is a glycosylphosphatidylinositol-anchored protein that is overexpressed on the surface of cancer cells in a spectrum of epithelial malignancies, but is limited in normal tissue. As such, CARs designed to target FRα can be used to treat any disease or disorders, including but not limited to epithelial cancers, characterized by cells and/or tissues displaying an overexpression of FRα. For example, the CAR designed to target FRα can be used to treat cancers and disorders including but are not limited to ovarian cancer, lung cancer, breast cancer, renal cancer, colorectal cancer, other solid cancers and the like.

However, the invention should not be construed to be limited to solely to the antigen targets and diseases disclosed herein. Rather, the invention should be construed to include any antigenic target that is associated with a disease where a CAR can be used to treat the disease.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of ovarian cancer. In certain embodiments, the cells of the invention are used in the treatment of patients at risk for developing ovarian cancer. Thus, the present invention provides methods for the treatment or prevention of ovarian cancer comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rittman. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Generation of Anti-α Folate Receptor (αFR) T-Body Molecules

The anti-αFR scFv (MOv19) was used as a template for PCR amplification of an 780-bp MOv19 fragment using the following primers:

```
                                              (SEQ ID NO: 24)
5'GCGGGATCCTCTAGAGCGGCCCAGCCGGCCATGGCCCAGGTG-3'
(BamHI is underlined)
and
                                              (SEQ ID NO: 25)
5'GCGGCTAGCGGCCGCCCGTTTTATTTCCAACTTTGTCCCCCC-3'
(NheI is underlined).
```

The resulting PCR product contained a BamHI site on the 5α end and a NheI site on the 3α end. The CD8α hinge, transmembrane, and cytosolic regions were amplified by PCR using previously constructed templates and the following primers:

```
                                              (SEQ ID NO: 26)
5'GCTGGGACAAAGTTGGAAATCAAAGCTAGCACCACGACGCCAGCGCC
GCGACC-3'
(NheI is underlined)
and
                                              (SEQ ID NO: 27)
5'TCGACAGTCGACTTAGCGAGGGGGCAGGGCCT-3'
(for the functional TCRζ containing molecules,
SalI is underlined).
```

The chimeric immunoreceptor constructs were generated through gene splicing by overlap extension. Equimolar amounts of the MOv19 PCR product and CD8 hinge, transmembrane, and cytosolic PCR products were combined with (SEQ ID NO: 28)
5'ATAGCA<u>TCTAGA</u>ATGGCCTTACCAGTGACCGCCTTGCTCCTGCCGCT GGCCTTGCTGCTC-3'
(XbaI is underlined)
and (SEQ ID NO: 29)
5'TCGACA<u>GTCGAC</u>TTAGCGAGGGGGCAGGGCCT-3'
(for the functional TCRζ containing molecules,
SalI is underlined).

The final PCR products were then digested with XbaI and SalI and ligated into pELNS, a third generation self-inactivating lentiviral expression vectors based on pRRL-SIN-CMV-eGFP-WPRE in which transgene expression is driven by the EF-1α promoter, which replaced the CMV promoter. High-titer research grade replication-defective lentiviral vectors were produced and concentrated.

Figure 6:
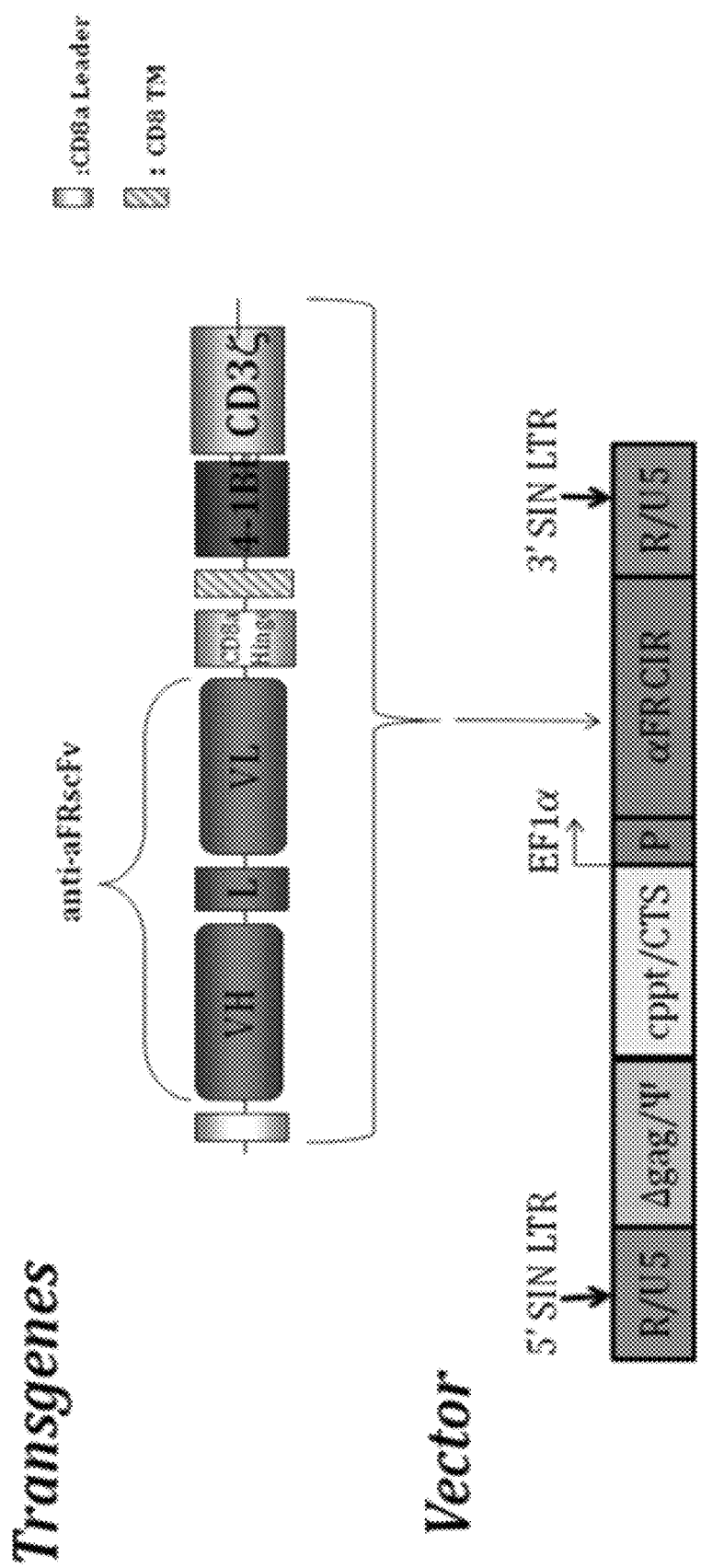
FIG. 6 is an image representing chimeric anti-alpha folate receptor immunoreceptor α-FR 4-1BB:CD3ζ transgene and vector construct. The construct was cloned into the pELNS backbone vector (bottom), which contains the packaging signal (ψ), the central polypurine tract/central termination sequence (cppt/CTS) and the elongation factor 1-α promoter (ef-1α). The transfer vector is driven off of the 5' LTR during packaging and the 3' SIN LTR is copied to the 5' end upon reverse transcription.
Figure 7:
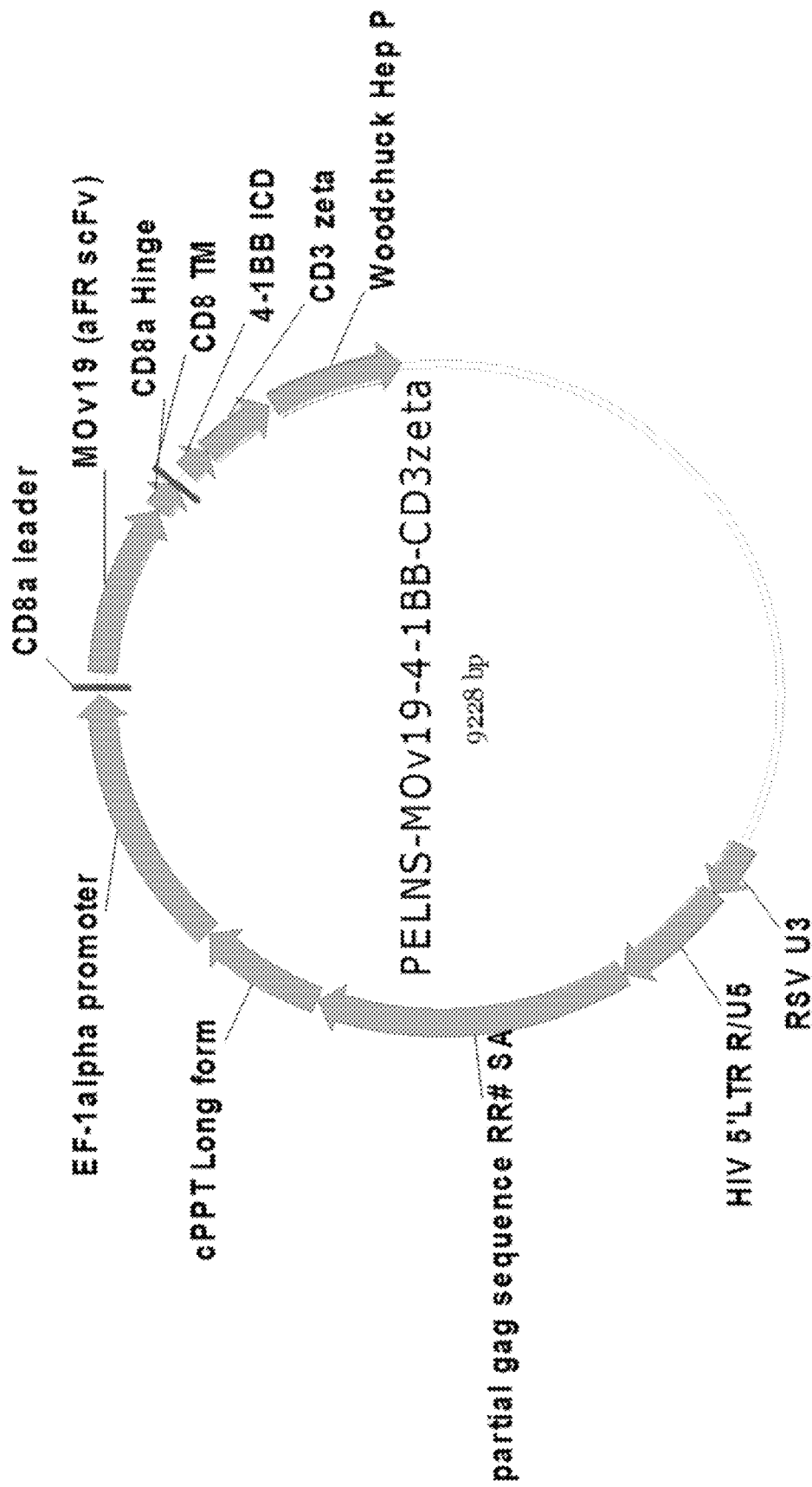
FIG. 7 is an image showing the plasmid map of PELNS—MOv19-4-1BB-CD3zeta.

The investigational agent in this protocol is autologous T cells transduced with α-FR-CAR (FIG. 6). Autologous T cells are transduced with a lentiviral vector expressing the α-FR CAR. This redirects specificity of the transduced T cells for tumor that expresses αFR, which is expressed at high levels in 90% of epithelial ovarian carcinoma (EOC) but is largely absent from normal. The α-FR CAR, is linked to an intracellular signaling molecule comprised of the TCRζ, 4-1BB. The scFv MOv19 is derived from a mouse monoclonal antibody, and thus contains mouse sequences that are immunogenic. If early clinical feasibility and efficacy is established, this scFv is humanized for later stage clinical development. The cytoplasmic signaling domains of the transgene are entirely of the native human sequences. These receptors are "universal" in that they bind antigen in an MHC-independent fashion, thus, one receptor construct can be used to treat a population of patients with alpha folate receptor antigen-positive tumors. The final transgene construct was cloned into the pELNS lentiviral vector (FIGS. 6 and 7).

Figure 8A:
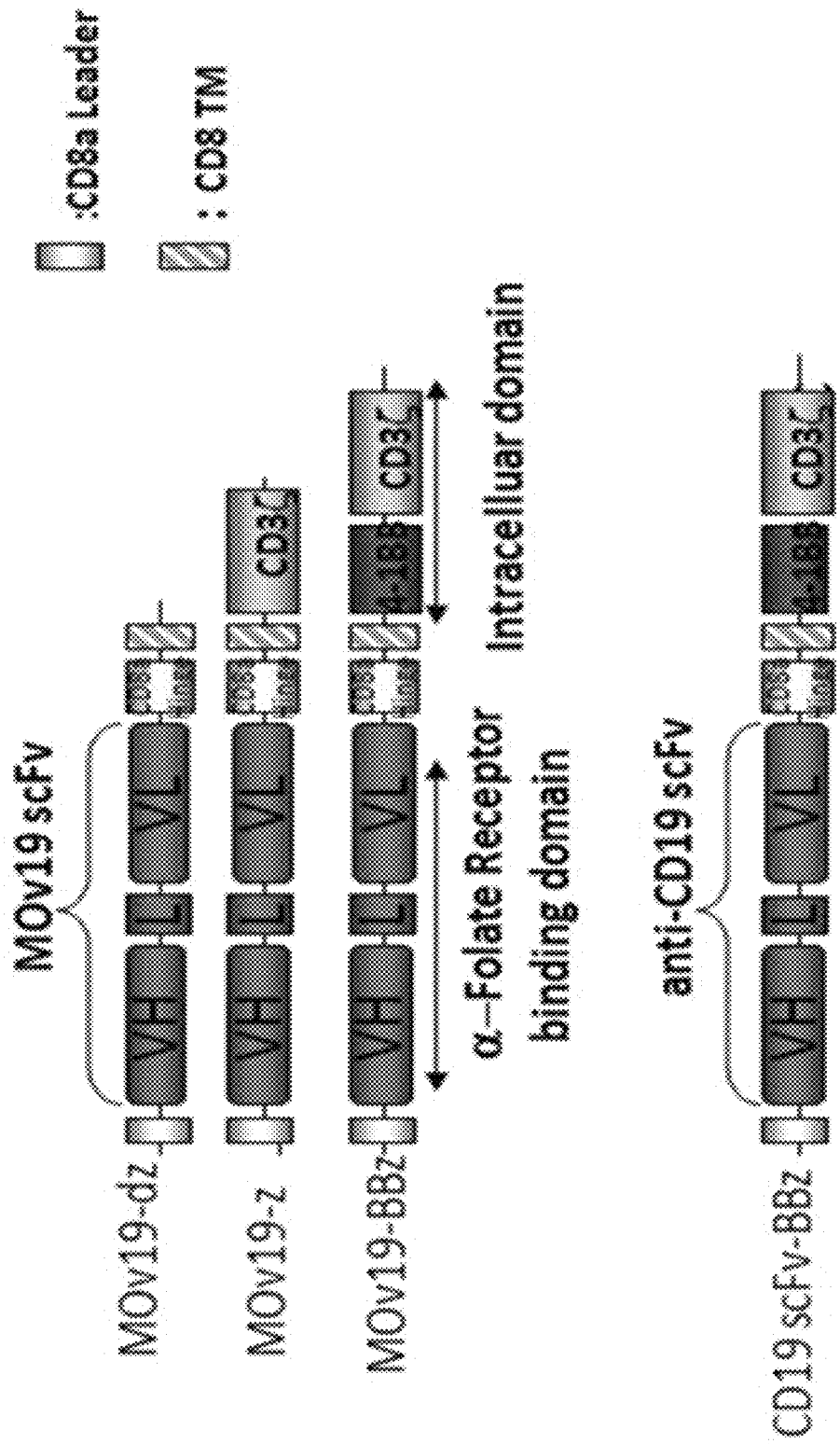
FIGS. 8A-8B are a series of images showing the generation and cytolytic activity of anti-αFR lentiviral vector-engineered T cells.

The plasmids used for alpha folate receptor (αFR) chimeric immune receptor genes delivery are schematically depicted in FIG. 8A. The transfer vector is an HIV derived self inactivating (SIN) vector that comprises a 5' LTR and a 3' U3 deleted LTR. Transgene transcription is driven off the mammalian ef-1α promoter. The transgene is composed of extracellular domain MOv19 (αFR scFv) and signaling domain 4-1BB and CD3zeta chain. The vector also contains the central polypurine tract and central termination sequence (cppt/CTS) for improved transduction efficiency, the rev response element (RRE) for RNA transport, the WPRE element for improved RNA translation and, the packaging sequence.

Novel CARs were constructed that contain a FRα-specific scFv (MOv19) coupled to either an inactive form of the CD3-ζ intracellular domain (MOv19-Δζ), CD3 ζ chain signaling module (MOv19-ζ) or in combination with the CD137 (4-1BB) costimulatory motifs (MOv19-BB-ζ) (FIG. 6). Human T cells were transduced with the CAR using lentivirial vectors. In co-culture assays, CAR transduced T cells were measured for reactivity against ovarian cancer cells expressing FRα via IFN-g ELISA and cytokine bead assay. Cytotoxicity was measured using a bioluminescence system in vitro. The potential antitumor efficacy of αFR CAR in Winn assay and xenograft model in NOG mice was explored.

Preparation, Structure, and Composition of the Materials that can be Given to the Patients or Used to Treat the Patient's Cells.

The CAR constructs were developed at the University of Pennsylvania, and the clinical grade vectors were cloned and are manufactured at The City of Hope under the direction of Dr. Larry Couture. The clinical grade engineered T cells are manufactured in the Clinical Cell and Vaccine Production Facility at the University of Pennsylvania. At the end of cell cultures, the cells are cryopreserved in infusible cryomedia in bags. Each bag contains an aliquot (volume dependent upon dose) of cryomedia containing infusible-grade reagents. Subjects in Stratum 1 can receive a single dose of α-FR CAR transduced T cells by direct intratumoral injection, either ultrasonically guided or intraoperatively using a dose escalation approach. Subjects in Stratum 2 receive split dose intravenous infusions (10%, 30%, and 60% on days 0, 1, and 2, respectively) of the transduced T cells using a dose escalation approach.

Measuring DNA Purity

The DNA used to manufacture the vector is isolated from *E. coli* cells grown in LB medium under ampicillin selection. The DNA undergoes quality control (QC) release testing to ensure its identity and purity. DNA is tested for appearance (clear and odorless), 260/280 ratio (1.7-2.0), agarose gel electrophoresis (≥90% supercoiled), residual RNA (non detected/μg), linear plasmid DNA or chromosomal DNA (none detected/μg), restriction enzyme mapping, endotoxin (<30 EU/mg), and sterility.

Viral Production

Lentiviral vector is produced by City of Hope. City of Hope has built a PhaseI/II cGMP Manufacturing facility consisting of two (2), independent, Class 10,000 manufacturing Suites (A&B) inside a unidirectional GMP support area. Each Suite consists of: an Entry/Gowning Airlock, a Cell Expansion Lab, Production Lab, Purification/Buffer Prep Lab, and Exit/Degowning Airlock. Each Suite has an independent air handler with HEPA supply and controlled exhaust. Pressure differentials between suites and within suites is controlled as well as temperature and humidity. Environmental conditions, and GMP equipment, is monitored, recorded and alarmed through a centralized Building Monitor System. All transfers and any open vessel operations take place in the suites in unidirectional flow, Class 100, hoods.

Supporting GMP areas include: GMP Controlled Storage, −80° C. Controlled Storage, +4° C. Controlled Storage, USP Water System, USP Gas Distribution Systems, Materials Airlock, separate locker room, Gowning Airlock, Entry Hallway, Autoclave/Wash Room, and Exit Hallway. All Airlocks, hallways, and direct access support areas are supplied by multiple GMP air handlers with HEPA filtered supply air to support spaces with an overall Classification of 100,000.

Viral Production in 293T Cells

Viral vector is produced by transient transfection using a three plasmid production system that provides gag/pol, tat, rev, and VSV-G in a system similar to (Zufferey et al, 1997). The only regions of overlap are in the packaging and gag and cppt/CTS sequences. RCL testing is performed in accordance with FDA guidelines as described later.

The process begins with a single vial of frozen, 293T cells from a GMP, validated, Master Cell Bank. Cells are thawed and expanded through a number of passages to increase cell count and volume of cells in a number of sizes of culture flasks. The City of Hope has both adherent and suspension cell lines. This is a general description of the adherent cell line production process:

The thawed cells are centrifuged to a pellet, resuspended in cell culture medium and a cell count is performed. Multiple flasks containing medium are seeded with cells to a specific cell density. The flasks are incubated at 37° C. and 5% $CO_2$ concentration in an incubator for ~24 hours. After 24 hours the medium is removed from the flasks containing cells, and Growth Media is added to the flasks and cells. Flasks are incubated again at same temperature and $CO_2$ for an additional 24 hours. Flasks are removed from the incubator, media removed, cells are loosened from the surface with Trypsin solution, cells counted, and expanded to 5 times more flasks to a specified seeding density with Growth Media in flasks. Flasks are incubated at 37° C. and 5% $CO_2$ for 48 hours. At the end of that time, media is removed from the flasks, cells are trypsinized, cells counted, and up to 10 Cell factories (4 layer) are seeded to a specified cell density and 800 mL of Growth Media per cell factory. Cell factories are incubated at 37° C. and 5% $CO_2$ for approximately 72 hours. Media is then removed from the Cell factories, cells are trypsinized, counted, and used to seed ten (10) Cell factories (10 layer each) with approximately 1.5 L of Growth Media. These ten (10) cell factories are incubated at 37° C. and 5% $CO_2$ for ~24 hours. The media is removed from the cell factories and the cells are transfected with Transfection reagent containing media, transfection reagent and three GMP plasmids.

The Transfection reagent consists of three GMP produced plasmids; the DNA plasmid containing effective gene, and two DNA helper plasmids, p93 and pVSV-G, in a calcium phosphate solution. The GMP plasmids are prepared by fully sequencing the DNA plasmid, transfecting an *E. coli* strain with the DNA, and growing the *E. coli* to produce a Master Cell Bank. A vial from the Master Cell Bank is used to express the DNA plasmid which is purified, aliquoted, and tested for sequence, purity, and sterility.

After the cell factories are transfected with Transfection reagent they are incubated for approximately 20 hours. The transfection reagent is poured off and Growth media is added to the cell factories. They are then incubated for an additional 24 hours before harvest.

Vector Purification and Release Testing

Viral vector is purified in compliance with good manufacturing practices (GMP). The fluids containing vector are poured from the cell factories, pooled, and then filter clarified through a 0.8/0.45 micron clarification filter. The clarified harvest is loaded on to an anion exchange resin in a chromatography column. The ion exchange column is washed with a low salt buffer and then the semi-purified vector is eluted with a 0.7 M NaCl buffer.

The elution buffer is then concentrated using a 500 kD tangential flow filter (TFF) membrane and diafiltered with a low salt buffer to a concentration of 10×. A benzonase endonuclease is added to the solution to remove residual DNA and incubated for approximately 1 hour. The treated solution is further concentrated with the 500 kD TFF membrane for an additional 10×, and then diafiltered with the formulation buffer with approximately ten (10) volumes. Following the diafiltration, the purified vector solution is further concentrated from 10× to 20× as required. The final concentrate is filled into sterile plasma bags with the desired volume, sampled, and then frozen to −80° C.

Samples are tested, and all documentation is reviewed, and approved before the material is released. Vector release testing is performed as follows: purity is tested by visual inspection (clear and colorless), pH (7.0-7.4), conductivity (4-7 mS/cm), fill volume (≥40 ml), total protein ≤0.70 mg/ml and benzonase (≤100 ng/ml or 0.1 ppm); identity is tested by silver stained SDS-page and by RT-PCR specific for the construct/transgene; potency is tested by titer on 293 cells (≥$2.5 \times 10^7$ TU/ml); for safety, the vector is tested for gag DNA by qPCR (undetectable), and for RCL by VSV-G DNA and a biological RCL test (described below); sterility testing includes endotoxin (<100 EU/ml), sterility (no growth), adventitious virus (undetectable) and mycoplasma (undetectable); vector is also tested by p24 ELISA (0.1-10 µg/ml). A separate C of A can be provided for each vector.

RCL Assay

Testing for recombination or replication competent lentivirus (RCL) is performed in accordance with FDA guidelines for the testing for RCR. C8166 cells are exposed to vector supernatant and passaged for 3 weeks. Culture supernatants are monitored for p24 production by ELISA, and for persisting or increasing numbers of packaging DNA measured by PCR. The test article for these assays, in accordance with the guidelines, is 5% or 300 ml of culture supernatant, whichever is less and $10 \times 10^8$ end of production (EOP) cells. Testing is performed at the National Gene Vector Laboratories at Indiana University.

Packaging, Shipment and Storage of the Vector

The first lots of vector is shipped to UPENN in accordance with City of Hope shipping SOPs as described in the Lentigen DMF. Shipment of future vector lots may occur from Omnia Biologics, Indiana University, or from Lentigen Corporation, depending on where the GMP lot is manufactured.

Vector Stability Monitoring Plan

The potency of the vector is determined in each cell product by transduction efficiency as measured by copy number and/or transgene expression levels. A stability monitoring plan is not be put in place for the vector for this study at this stage because each vector lot is individual and small in size. In addition, a stability testing plan requires that the CVPF ship vector back to the manufacturing facility for titration using their standard assay. The introduction of a shipping step to the stability testing introduces a variable.

Intended Target Cells of Recombinant DNA, Cells that are to be Treated Ex Vivo and Returned to the Patient, Characterized of Cells Before and after Treatment, and Target Cells Incorporation of the DNA The target cell product is autologous CD3+ autologous T lymphocytes. T lymphocytes are enriched from a leukapheresis product by depletion of monocytes via counterflow centrifugal elutriation on the Gambro Elutra, which employs a single use closed system disposable set. On day 0, the αFR T-body manufacturing process is initiated with activation of T lymphocytes with anti-CD3/CD28 mAb coated magnetic beads. αFR vector is added in split doses with 50% on day 0 and 50% on day 1. Vector transduction occurs between days 0 and 3. On day 3, the cells are washed and media is replaced. Cultures are typically expanded from 9-12 days. At culture harvest, cells are depleted of magnetic beads, washed, concentrated, and cryopreserved.

At the start of culture, the enriched CD3+ T-cell culture generally contains some amount of residual αFR CAR+ cells (B cells ~5-10%), CD16+ (NK cells ~5-10%) and CD14+ cells (macrophages at ~<5%). Therefore, these cells are exposed to the vector during transduction, and incorporate the recombinant transcript. After expansion in vitro, the final cellular product is typically >90% CD3+ lymphocytes. Culture conditions don't support growth of macrophages or B cells, and by the end of the culture period B cells comprise ~<2%, and macrophages ~<1% of the total culture.

The method of ex-vivo transduction ensures that only peripheral white blood cells enriched for lymphocytes are exposed to the vector. Any residual non-integrated vector is washed away at day 3 during the expansion and again during the harvest and concentration prior to formulation of the final cellular product. The vector cannot mobilize, even in the presence of HIV, accordingly, there are no concerns regarding vertical or horizontal transmission of the vector, or transmission to cells not present in the starting culture.

Below is a detailed description of the manufacturing process:

Cell Collection and Purification

On day 0 of the T-cell manufacturing process, non-mobilized peripheral blood leukocytes is obtained through a leukapheresis collection. Approximately 10 L is collected and processed on the Baxter Amicus Cell Separator or equivalent to obtain a population of approximately $5$-$15 \times 10^9$ white blood cells. The product is taken to the CVPF, where samples are taken for bacterial and fungal cultures and phenotyping by flow cytometry. Cell number is determined on the Coulter Multisizer III and viability is tested by trypan blue exclusion assay. The apheresis product is then processed with the Gambro Elutra, which utilizes counter-flow centrifugal force to separate cell populations based on size and density. The Elutra operates as a closed system and the use of a disposable tubing set further minimizes the risk of contamination. The lymphocyte fractions collected following the Elutra separation are combined and washed using the Baxter CytoMate, Cell Saver 5 or the COBE 2991 Cell Processor. Composition of the cell product (CD4+, CD8+, B-cell and macrophages, etc) is assessed and tracked by flow cytometry performed on the post-Elutra lymphocyte fraction, and the monocyte fraction.

Following the cell enrichment process (day 0), the enriched lymphocytes are activated with anti-CD3/anti-CD28 mAb coated magnetic microbeads at a 3:1 bead to cell ratio. This optimal bead:cell ratio was previously determined (IND #6675 and Levine et al., 1997). Enriched lymphocytes (via elutriation or positive selection) are stimulated with Dynabeads conjugated with mouse anti-human CD3 and CD28 in static tissue culture flasks. Transduction is performed on day 0 and day 1 of culture with a predetermined MOI (25 TU/cell of the FR vector for example) by addition of the αFR CAR lentiviral vector at 50% of the total transduction MOI per day. The vector is washed away by media replacement in a Baxter CytoMate Cell Processing System or Cell Saver 5 device on day 3 of culture. After the vector wash off, the cell and bead mixture are seeded back into gas permeable tissue culture flasks in fresh media and placed at a 37° C. incubator with 5% $CO_2$ and >90% of humidity for cultivation and further expansion. The cell culture is maintained in a closed system. Tubing leads on the tissue culture flasks are connected or disconnected through a variety of sterile tubing connecting devices and heat sealers (e.g. spike connectors, tubing welds from the Terumo Sterile Connecting Device, heat seal from the Sebra Heat Sealer) to prevent the risk of contamination. Cells are counted daily from day 3 to day 5 of culture. After 5 days of cultivation, cells may be counted every other day. Fresh media is added to the culture to maintain the cells at an appropriate density. During the log phase of cell growth, if needed, cultures are transferred to the WAVE Bioreactor, where cell concentrations may reach $1 \times 10^7$ cells/ml or higher. Optimized cell culture conditions in both the WAVE Bioreactor 2/10 and 20/50 has been previously established (June IND 12799 and Hami et al., 2003, 2004). The advantage of the WAVE is that T cells are grown at higher densities, which saves labor on processing and during the cell harvest. For cell doses up to $1 \times 10^{10}$ the WAVE Bioreactor is not needed.

Culture Harvest and Final Formulation, Cryopreservation

On the final day of the culture, cells are harvested and concentrated using the Baxter Fenwal Harvester or an equivalent system. Before and after processing cells through the Harvester, the cell product is placed on the Baxter MaxSep for removal of the anti-CD3/CD28 magnetic microbeads. αFR CAR T cells are resuspended in cryopreservation media. Cells are frozen in bags using a controlled-rate freezer. Cryopreserved αFR CAR T cell products are stored in a monitored freezer at ≤−130° C. Each infusion bag can contain ~10-50 mL of cells depending upon the size of the dose.

Cell Purity and Release Testing

Release testing for αFR-CAR T cells is similar to previous similar gene therapy cellular products manufactured for clinical trials at the Clinical Cell and Vaccine Production Facility (ref June IND #6675, 8568, 12799, 13911). The αFR-CAR T cells are tested and released based on cell viability (sentinel tube, ≥70%), % CD3+ cells (≥80%), residual bead count (≤100 beads/3 million cells), endotoxin (<3.5 EU/ml; the limit of 3.5 EU/ml was derived in the following manner: at a max volume of 100 mls, cryopreserved cell concentration of $100 \times 10^6$/ml equals a cell dose of $1 \times 10^{10}$ cells. $3.5 \times 100 = 350$EU, avg person=70 kg, so limit is 5EU/kg), vector copy number (≥0.2 copies per cell), αFR CAR expression (≥20% expression by flow cytometry), VSV-G DNA (undetectable), RCL by HIVgag DNA and p24 protein (negative), mycoplasma (negative), and bacteria/fungal cultures (no growth).

Structure of the Added DNA Sequences Monitored and Sensitivity of the Analysis.

Lentiviral vectors permanently modify the cell's DNA by integrating a DNA copy of their viral genome into cellular DNA. Thus, these sequences can be monitored in vivo by PCR of DNA isolated from PBMCs. A PCR assay has been developed that detects the junction region between the CAR chimeric signaling domain, so that the genetic construct can be distinguished from the endogenous signaling chains that exist in nature. This allows for monitoring of the persistence of the vector modified cells in each patient.

Stability of the Added DNA Both in Terms of its Continued Presence and its Structural Stability.

For safety purposes, the average culture copy number per cell is limited to the range of 0.2-5. The copy number after expansion is stable since the vector is stably integrated into the cell's DNA. Detection of vector copies in vivo after dosing may increase or decrease over time, as a result of the expansion, trafficking and persistence of the vector modified cells.

The results of the experiments are now described.

Figures 3A, 3B:
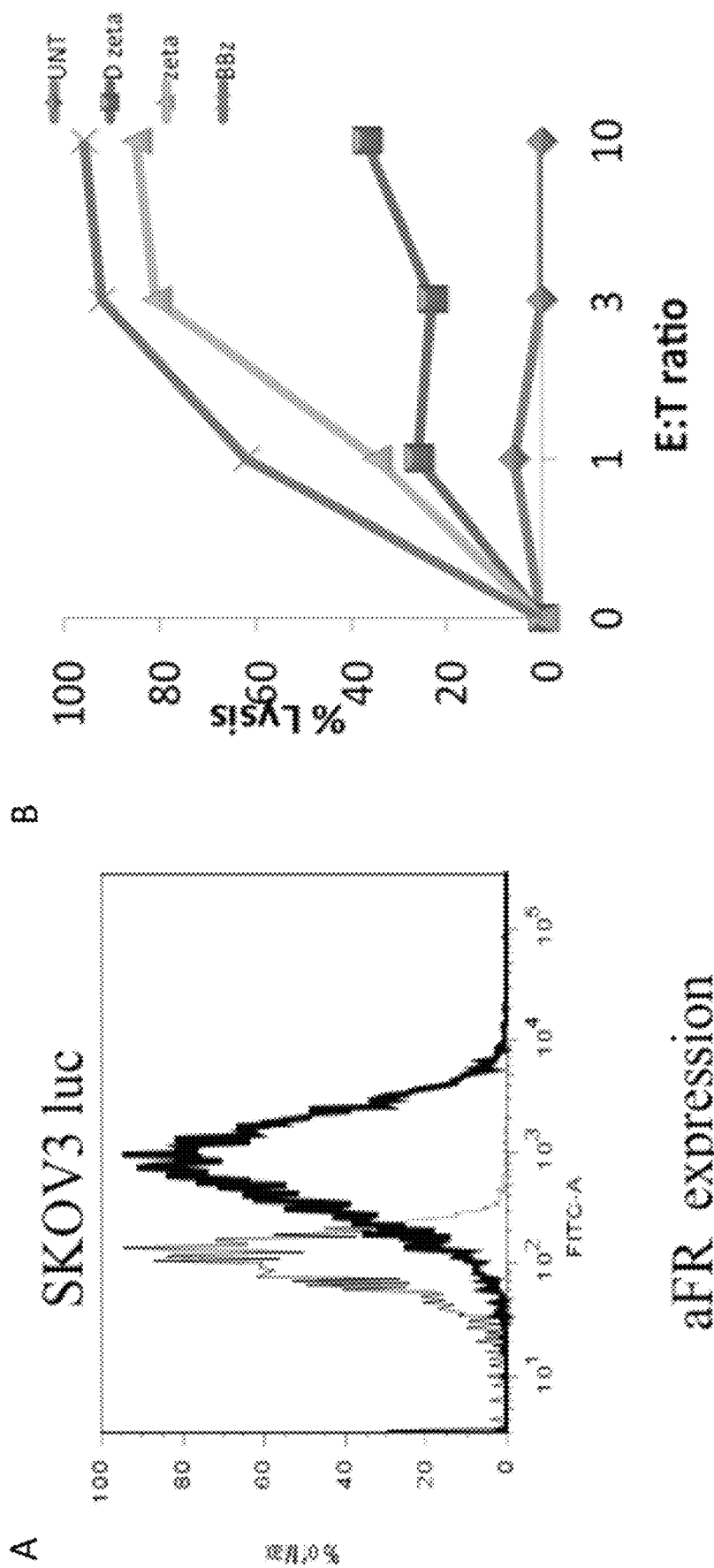
FIGS. 3A-3B are a set of graphs showing direct and specific tumor recognition and killing of αFR+ human ovarian cancer.
Figures 4A, 4B, 4C:
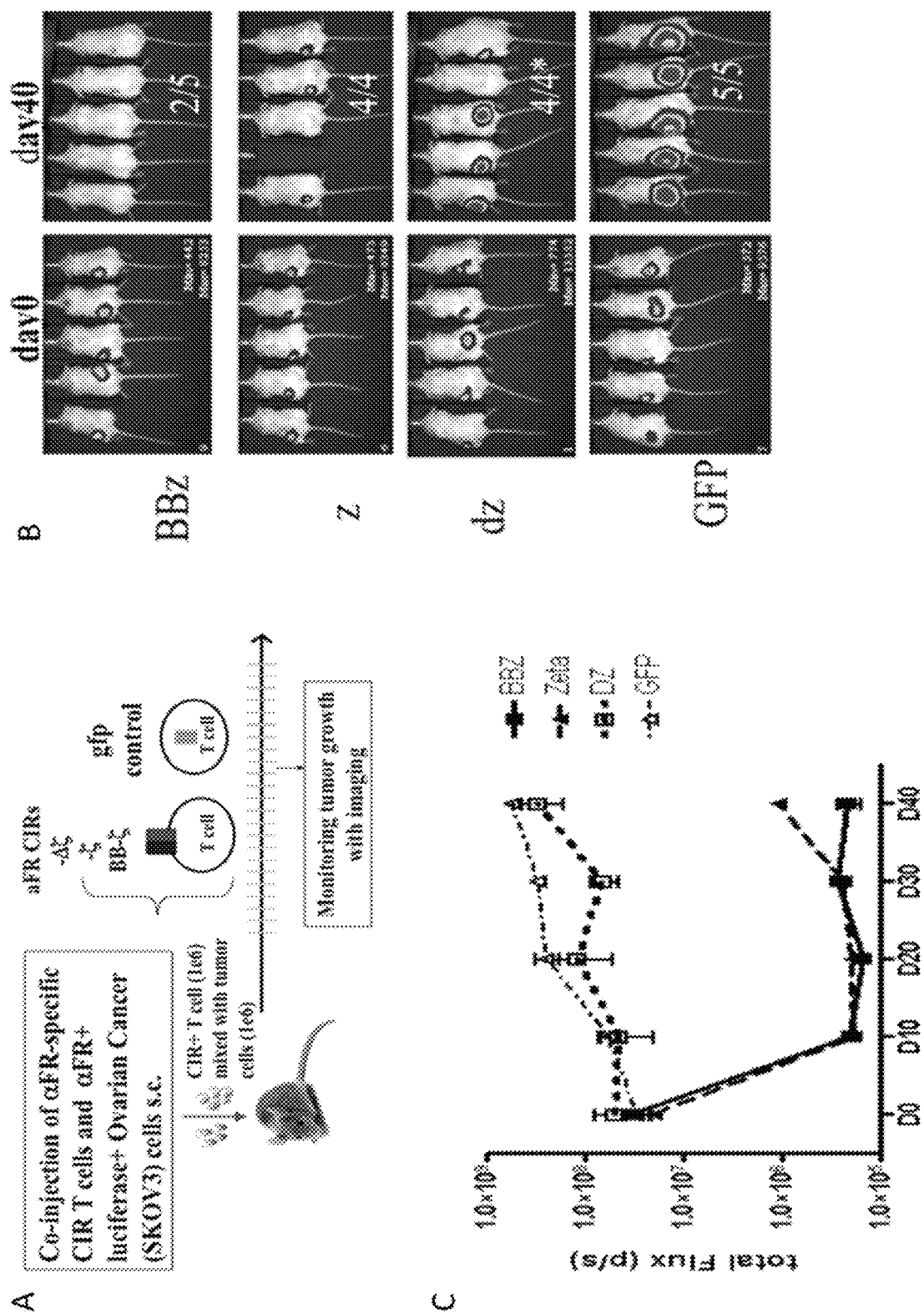
FIGS. 4A-4C are set of images and a graph showing that incorporation of the 4-1BB signaling domain can enhance anti-tumor activity in Winn assay.
Figures 5A, 5B:
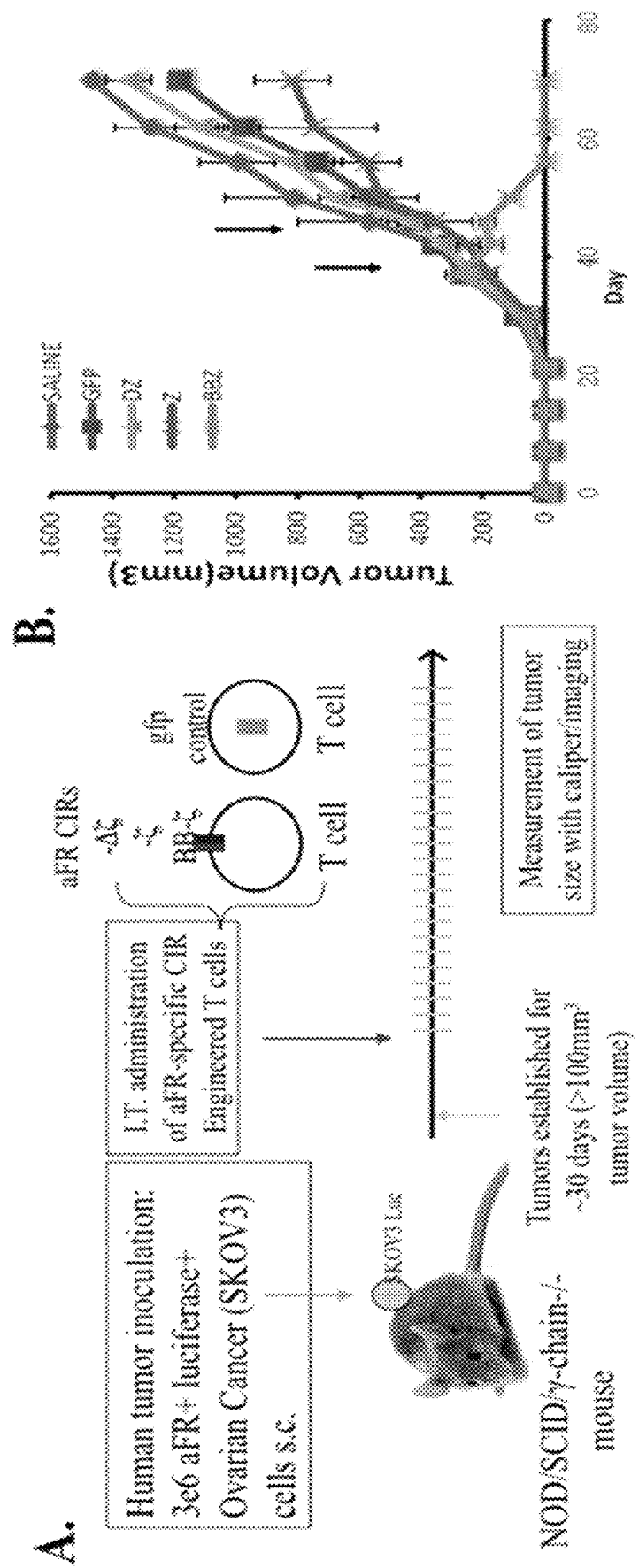
FIGS. 5A-5E, are a series of images showing treatment of large, established human ovarian cancer using CAR gene therapy: 4-1BB costimulation mediates enhanced T cell survival.
Figure 5C:
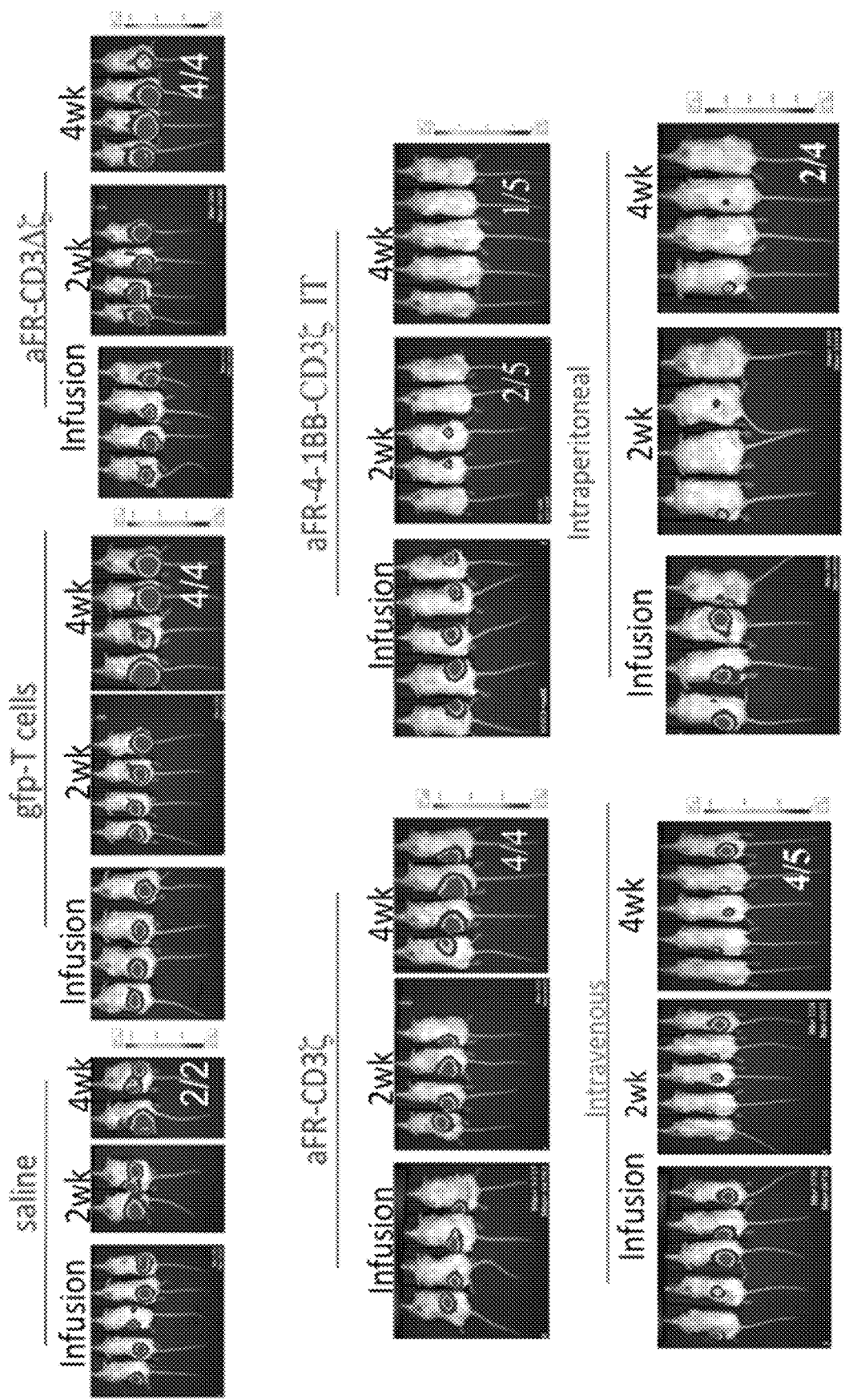
Figures 5D, 5E:
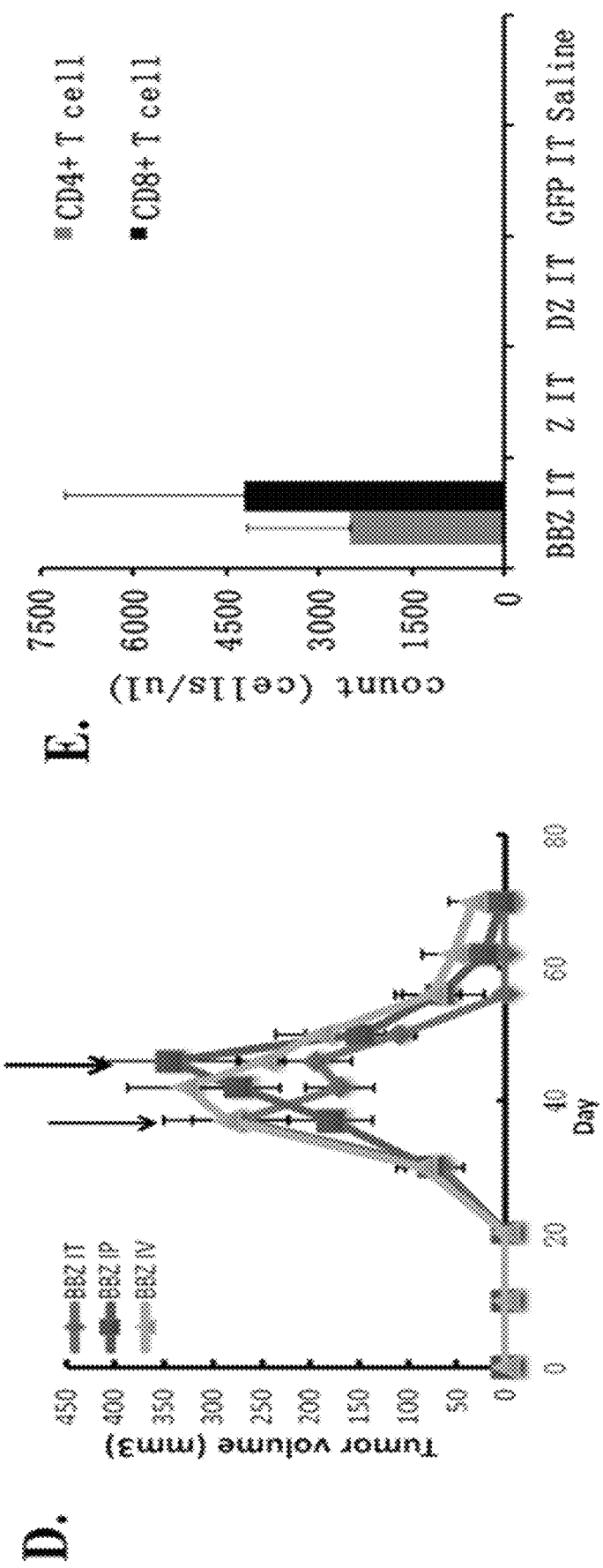

Example 1: Eradication of Human Ovarian Cancer Following Adoptive Transfer of Genetically Modified α-Folate Receptor-Specific T Cells Human T cells expressed cell surface scFv Mov19 40~50% after lentiviral transduction (FIGS. 3A-3B). MOv19-ζ and BB-ζ transduced T cells demonstrated target-specific release of IFN-g, TNF-α and IL-2 cytokines and cytotoxicity function when co-cultured with FRα+ tumor cells, while T cells transduced with MOv19-Δζ or with GFP did not (FIGS. 4A-4C). In an in vivo Winn assay, MOv19-ζ transduced T cells were able to inhibit the out growth of FRα+ ovarian cancer (FIGS. 5A-5E and 6). In contrast, T cells transduced with the MOv19-Δζ or with GFP had no effect on tumor growth (FIGS. 5A-5E and 6). Notably, in vivo anti-tumor activity of MOv19 CAR was improved through provision of 4-1BB (CD137) signaling (FIG. 6). Furthermore, it is demonstrated that incorporation of the costimulatory domains enhanced the persistence of T cells and is associated with improved anti-tumor efficacy in vivo (FIG. 7).

Example 2: Efficiency of DNA Delivery and Target Cell Percentage Containing DNA

Figure 8B:
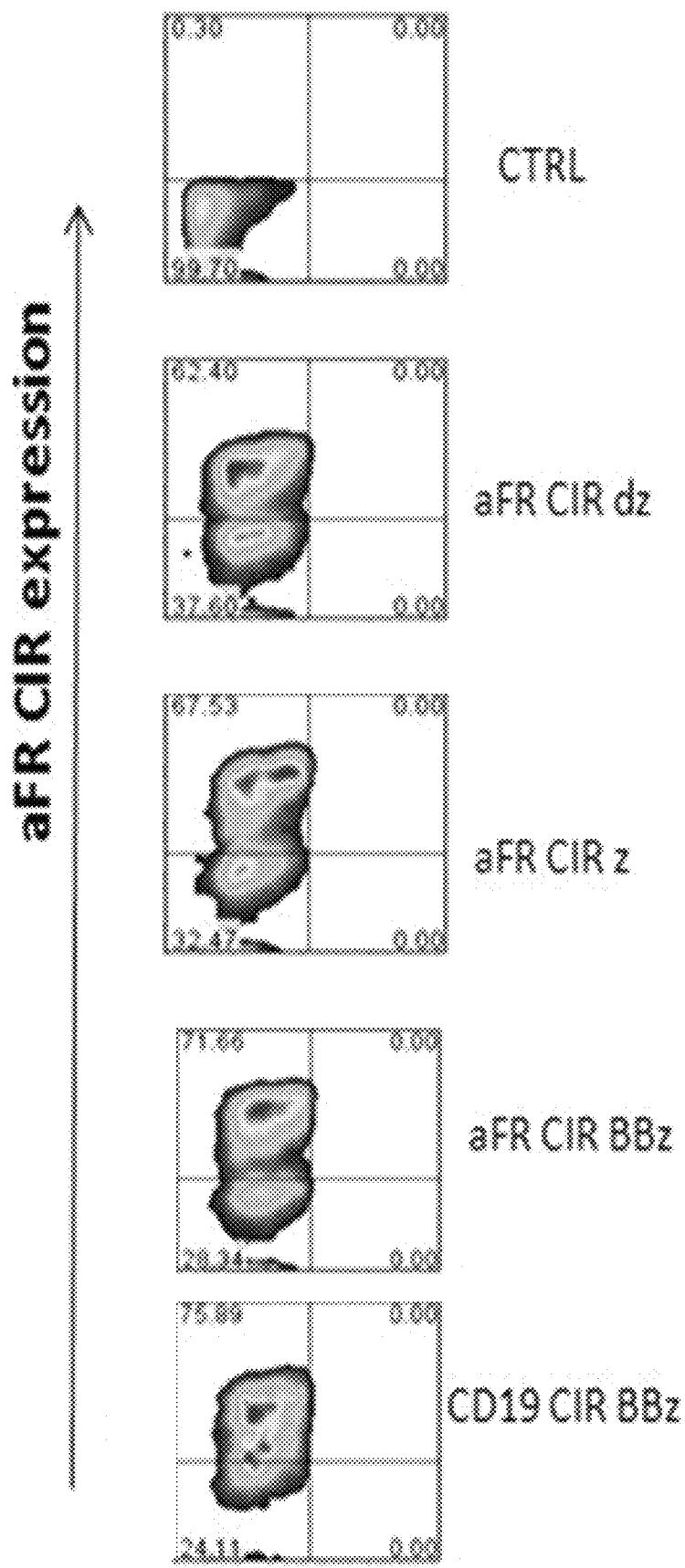

The lentiviral vector delivery system described is highly efficient in delivery of genes to T lymphocytes. In preclinical experiments using the T-body constructs proposed for this trial, it was routinely demonstrated >60% transduction efficiency for the α-FR-CAR protein in CD4+ T cells transduced to express the αFR CAR with CD3 zeta and 4-1BB signaling domains (FIG. 8B). Lentiviral vectors are well known for their superior gene transfer efficiency when compared to murine retroviral vector transduction efficiencies.

Example 3: In Vitro Assessment of Function

Figures 9A, 9B:
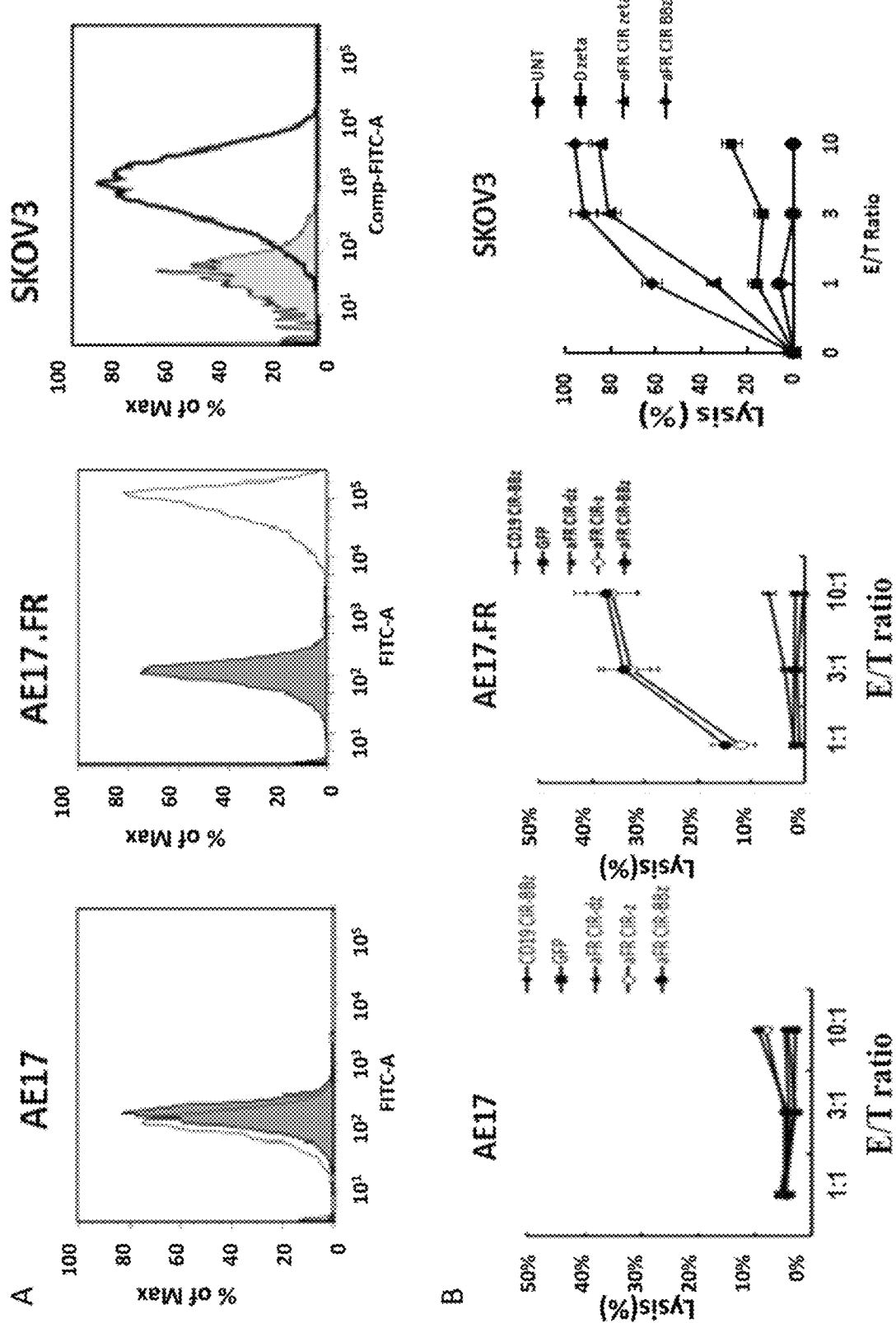
FIG. 9A is a series of images showing that the cell surface expression of FR on AE17, AE17.FR, SKOV3 was determined by flow cytometry. Cells were incubated with either the mouse anti-human αFR antibody MOV18 (light gray histograms) or an isotype control (dark gray histograms) followed by staining with a FITC-conjugated goat anti-mouse Ig.
FIG. 9B is a series of plots showing cytolytic activity of the chimeric receptors on primary human T cells targeting cell lines expressing αFR determined using a 4 h $^{51}Cr$ release assay. FRa+ tumor targets can directly induce T cell cytokine secretion.
Figure 9C:
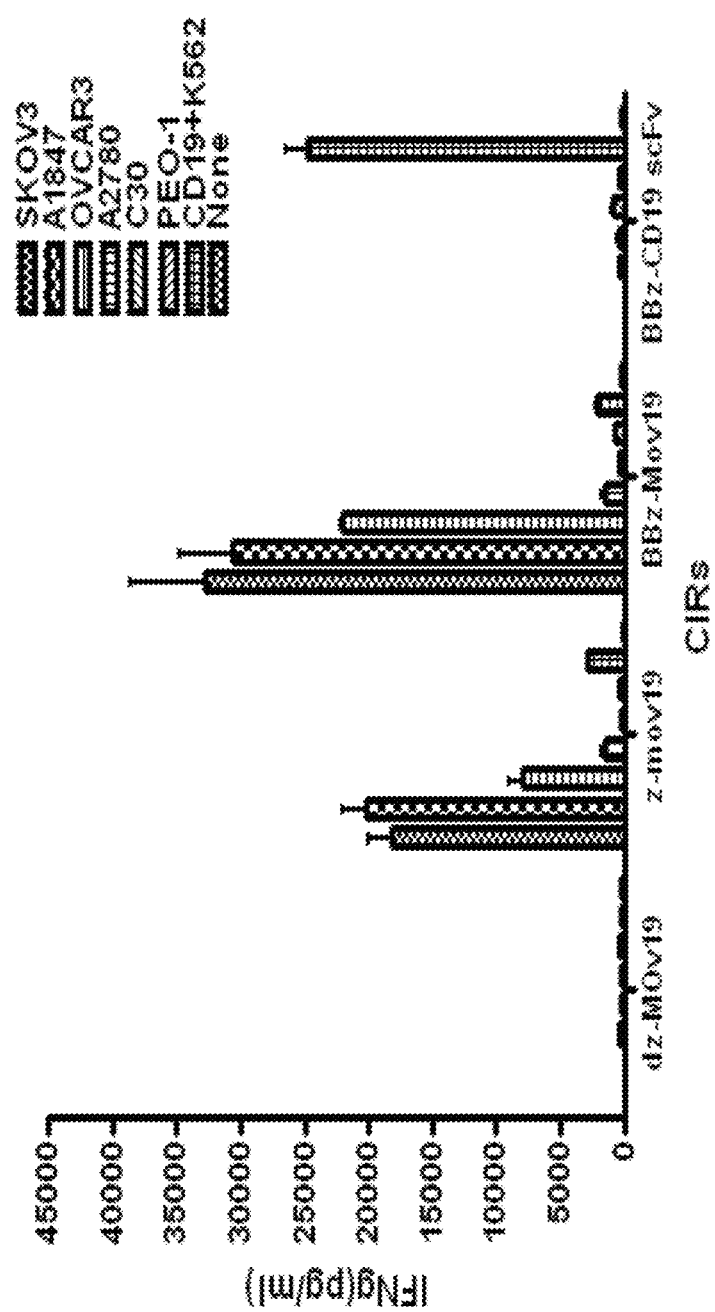
FIG. 9C is a plot showing results expressed as a mean and SD of triplicate wells from 1 of at least 3 separate experiments.
Figure 10:
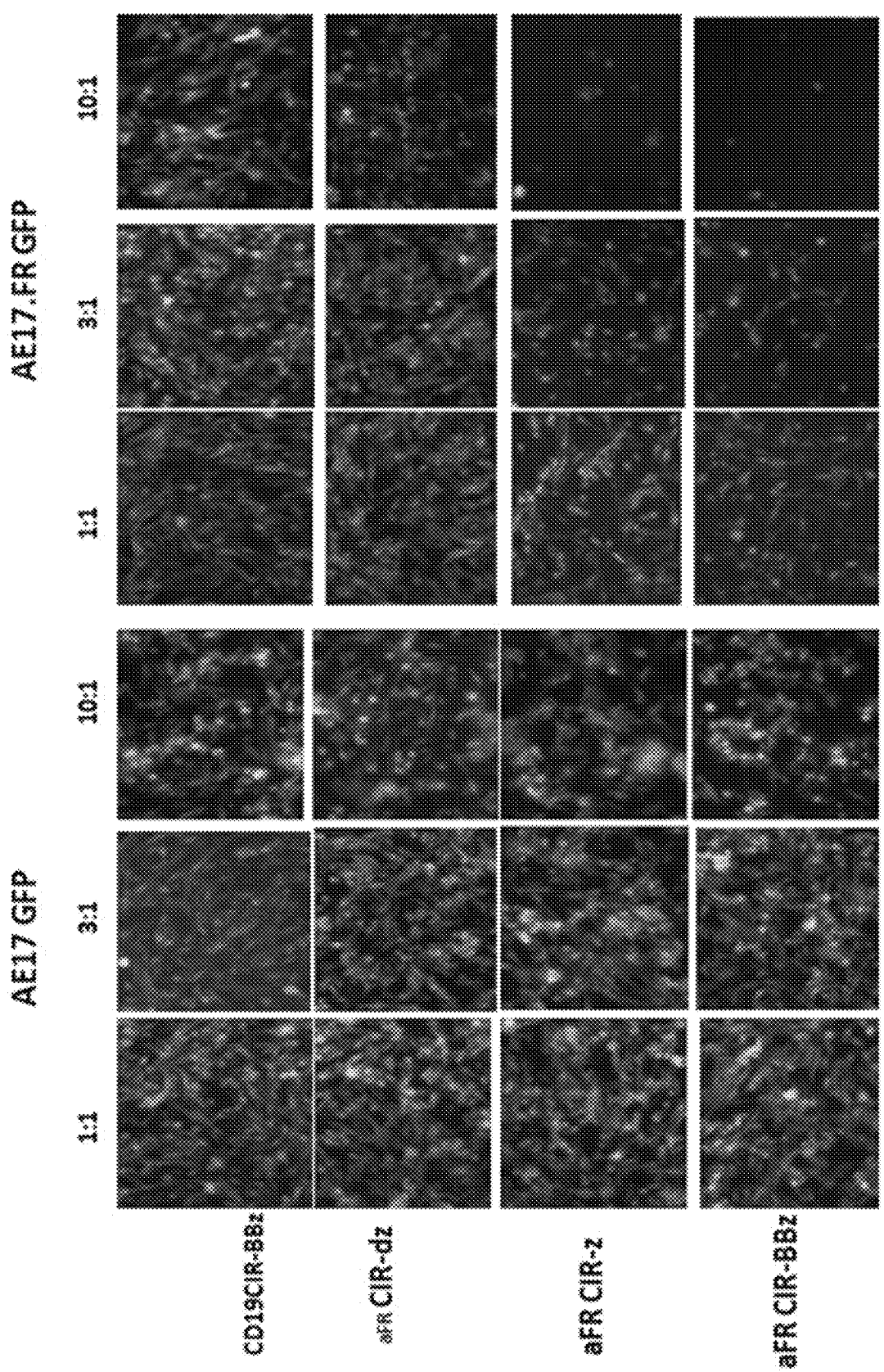
FIG. 10 is a series of images showing efficient αFR-specific killing of AE17.FR tumor cells in vitro. AE17 and AE17.FR cells transduced with GFP incubated CAR+ T cells for about 20 h at the indicated ratios, after which cells were photographed under fluorescence microscopy. The CAR transduction efficiency for each group of T cells was ~40%-50%.

Several preclinical studies have been carried to demonstrate the in vitro and in vivo efficacy of the gene transfer system and its payload (FIGS. 9A-9C). To investigate the antitumor potential of the transduced T cells, effector function was measured in standard chromium release assays using αFR-negative AE17 cells, AE17.FR (a derivative engineered to express αFR), and established human ovarian cancer cell lines. T cells transduced with αFR CAR efficiently lysed AE17.FR but did not kill parental AE17 cells. Importantly, the αFR CAR-transduced T cells were also highly cytotoxic for carcinoma cells that express αFR, killing human ovarian cancer SKOV3 cell lines. The inclusion of 4-1BB (CD137) costimulatory domains in tandem or in triplicate with TCR-ζ generally did not increase in vitro cytotoxicity above that of T cells expressing αFR CAR TCR-ζ only. The killing was efficient, with plateau lysis occurring at a 10:1 E:T ratio during a 20-h culture (FIG. 10) suggesting that the redirected T cells were capable of serial killing. Moreover, the lysis was specific because T cells transduced with GFP or an irrelevant CD19-CAR showed no cytotoxic activity against the same target cells, excluding alloreactivity or nonspecific lysis. Furthermore, T cells expressing a truncated TCR-ζ intracellular domain (αFR-Δz) also failed to kill αFR-expressing targets, demonstrating the requirement for an intact TCR-ζ signaling domain. CAR+ T cells were co-incubated with a panel of tumor cell lines and the amount of secreted effector cytokine IFN-g was determined. CAR+ T cells recognized FRα+ tumor lines SKOV3 and A1847 and secreted IFN-g at very high levels. A moderate level of IFN-g was observed in co-incubated with the OVCAR3 and A2780, which express FRα at moderate level. A low level of IFN-g was observed in co-incubated with the C30 and PEO-1 cell line, which was negative for αFR expression by FACS analysis (FIG. 9C).

Example 4: In Vivo Assessment of Function Winn Assay

Figures 11A, 11B:
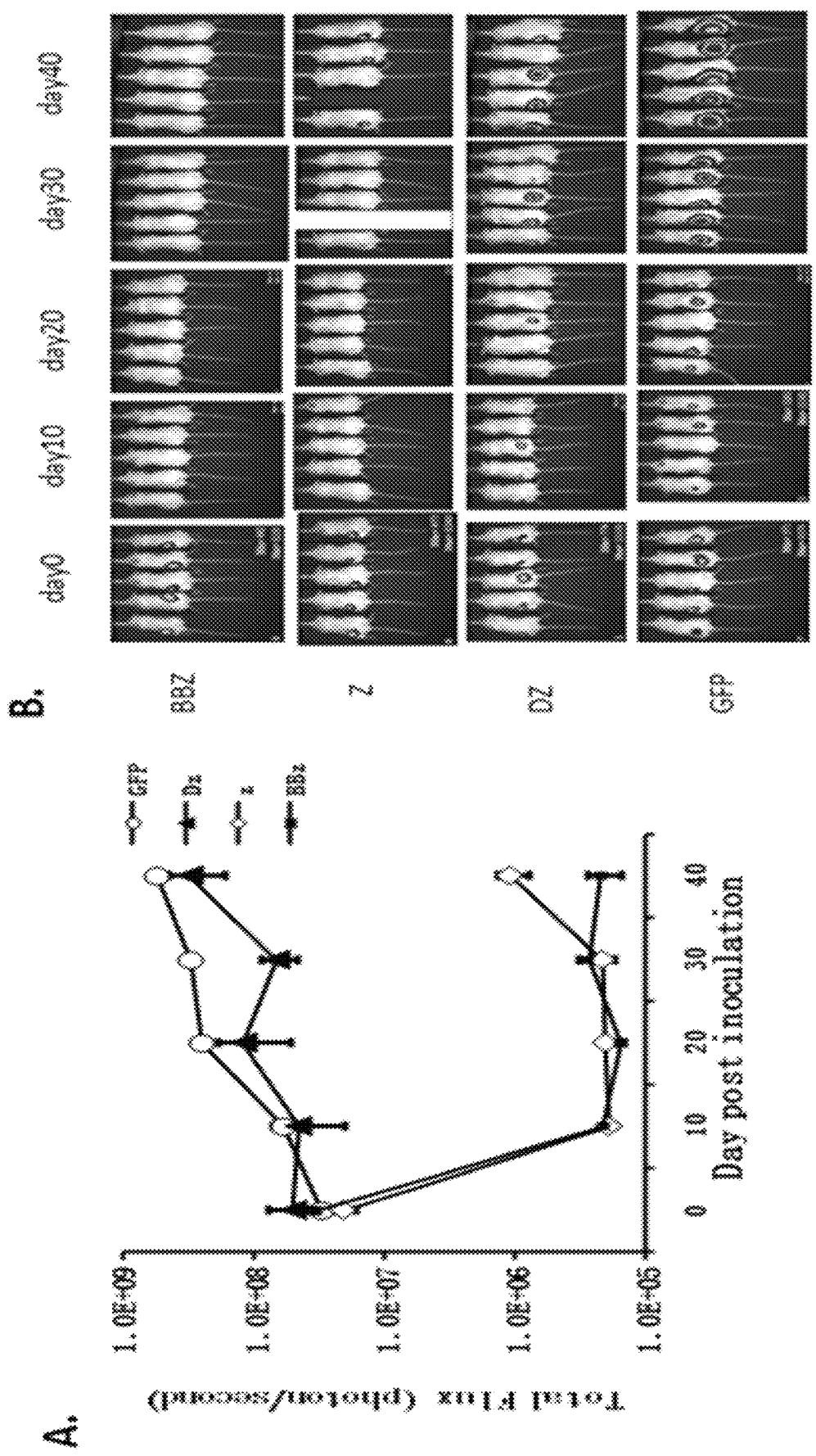
FIGS. 11A-11B are a series of images showing anti-tumor activity of αFR chimeric receptor transduced T cells in vivo. NOD/scid/IL2rγ$^{-/-}$ (NOG) mice were injected s.c. of SKOV3 Luc($1\times10^6$ cells/mouse) mixed with CAR expressing T cells ($1\times10^6$ cells/mouse). Mixing of cells was performed immediately before injection to minimize T cell and target interaction. The animals were imaged after inoculation every 10 days to evaluate tumor growth, and photon emission from luciferase-expressing cells was quantified using the "Living Image" software.

As an initial test of in vivo antitumor activity of the αFR CAR constructs, Winn assay was performed by the s.c. injection of a αFR+ human ovarian cancer cell line SKOV3 expressing Luciferase ($1 \times 10^6$ cells/mouse) mixed with CAR expressing T cells ($1 \times 10^6$ cells/mouse). The animals were imaged after inoculation and every 10 days to evaluate tumor growth, and photon emission from luciferase-expressing cells was quantified using the "Living Image" software (Xenogen). No effect was observed on the tumors growth in mice treated with either GFP or αFRCAR dz transduced T cells (FIG. 11A). In these control groups, animals started to develop a tumor at approximately day 30 after inoculation with all animals developing tumor by day 40 (FIG. 11B). By contrast, mice injected with αFR CAR-z or BBz bearing T cells inhibited tumor outgrowth equally until day 30 after inoculation demonstrating a requirement for an intact TCR CD3 zeta signaling domain in Winn assay. However, after another 10 days, all mice from αFR CAR CD3 zeta group had detectable tumor (4/4), whereas only 3/5 mice from the BBz group had tumors. These tumors are substantially smaller than the CD3zeta group tumors. These data show that incorporation of 4-1BB(CD137) into FRα CAR could enhance anti-tumor activity in vivo.

Example 5: Xenograft Model

Figures 12A, 12B:
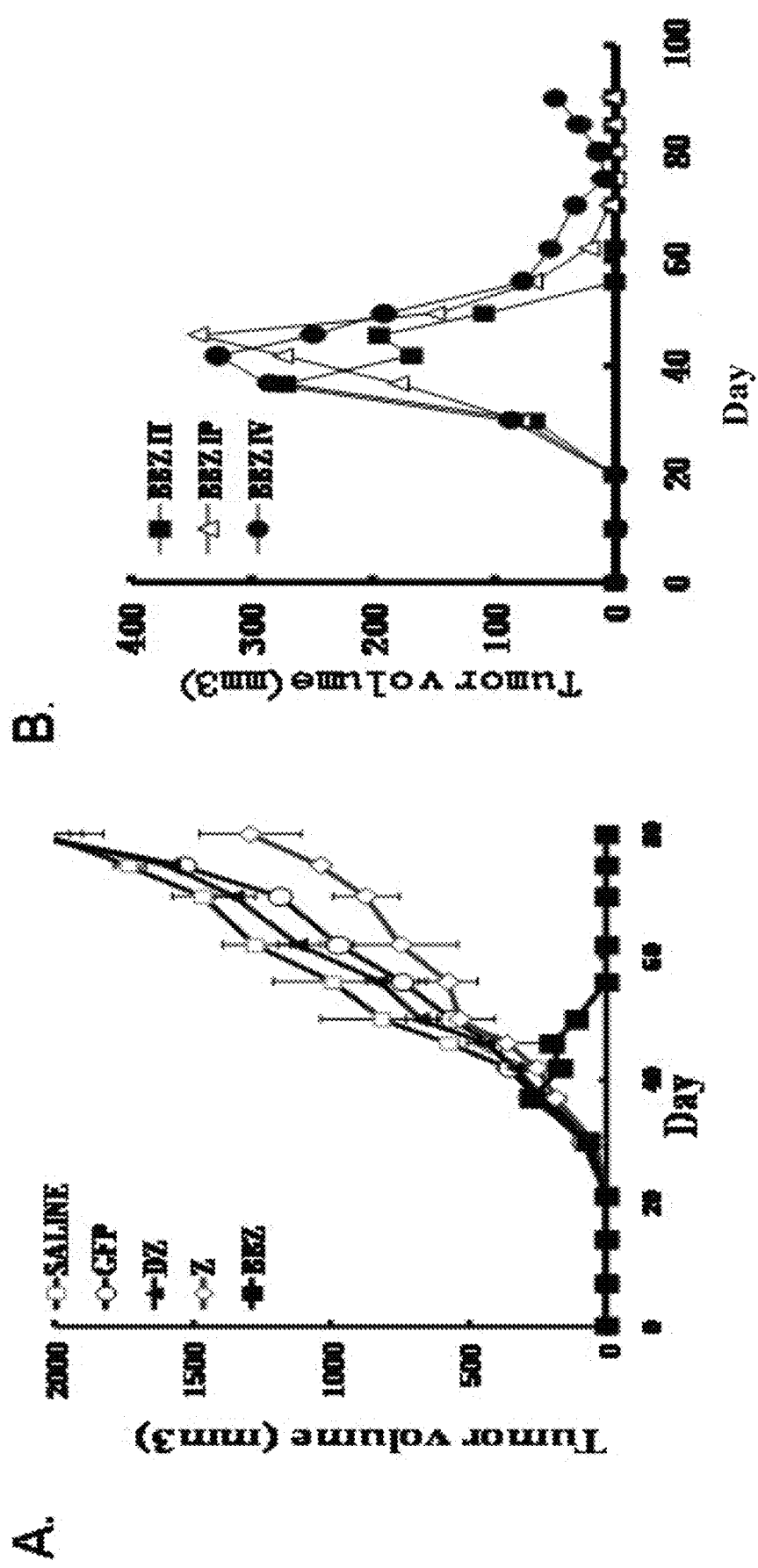
FIGS. 12A-12D are a series of images showing that αFR retargeted T cells eradicate large pre-established tumors in vivo: effect of costimulatory signaling domains and route of administration.
Figures 12C, 12D:
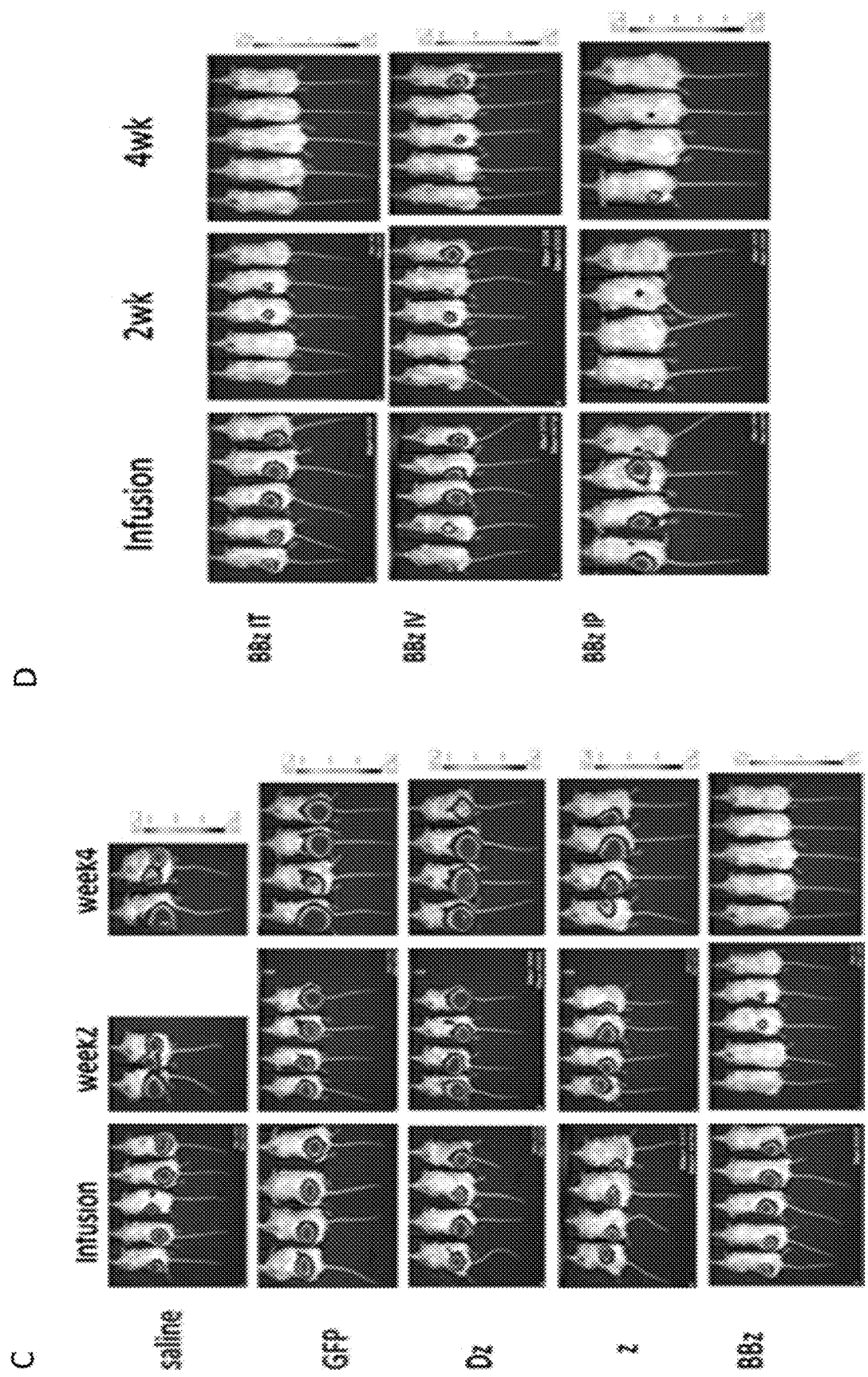

To further explore the potential antitumor efficacy of the αFR-CAR constructs, a xenograft model using SKOV3 Luc tumor cells was developed. 6 to 12-week-old female NOG mice were inoculated s.c. with $3 \times 10^6$ SKOV3 Luc cells on the flank on day 0. After tumors become palpable about 1 month, human primary T cell (CD4+ and CD8+ T cells used were mixed at 1:1 ratio) were activated, and transduced as described above. After 2 weeks ell expansion, when the tumor burden was 200~300 mm³, the mice were treated with T cells (~40%-50% transgene-positive). The route, dose, and timing of T-cell injections is indicated in the individual figure legends. Tumor dimensions were measured with calipers, and tumor volumes calculated using the formula $V=\frac{1}{2}(\text{length} \times \text{width}^2)$, where length is greatest longitudinal diameter and width is greatest transverse diameter. Tumor-bearing mice were treated with intratumoral injections of $20 \times 10^6$ T cells (~40%-50% transgene positive) on day 40 and 45 post tumor inoculation. Human donors were used to generate the transduced T cells. All the mice in the saline group, which did not receive cell based therapy, showed continued tumor growth. Similarly, the mice receiving αFR CAR dz with signaling deficiency or GFP transduced T cells showed continued tumor growth beyond the time of T cell transfer. The mice receiving αFR CAR-z T cells showed slowed tumor growth which was no significantly different when compared to all three control group (FIG. 12 A, C). The mice receiving αFR CAR BBz T cells displayed rapid tumor regression compared to all other the groups, suggesting that 4-1BB signaling mediate enhanced antitumor responses in vivo.

In order to evaluate the effect of different routes of administration, the tumor bearing mice were also treated using αFR CAR BBz transduced T cells by intravenous (i.v.), intraperitoneal (i.p.) injection and intratumoral (i.t.) injection. Following i.v. and i.p. injections, a potent antitumor effect was again observed (FIG. 12 B,D), but showed about 7 days delayed reduction in tumor mass compare to the intratumoral route of administration (FIG. 12 B). The intratumoral injection appears to be the superior route of administration, marginally faster than i.v. and i.p.

Example 6: Persistence of Human T Lymphocytes after Transfer

Figure 13:
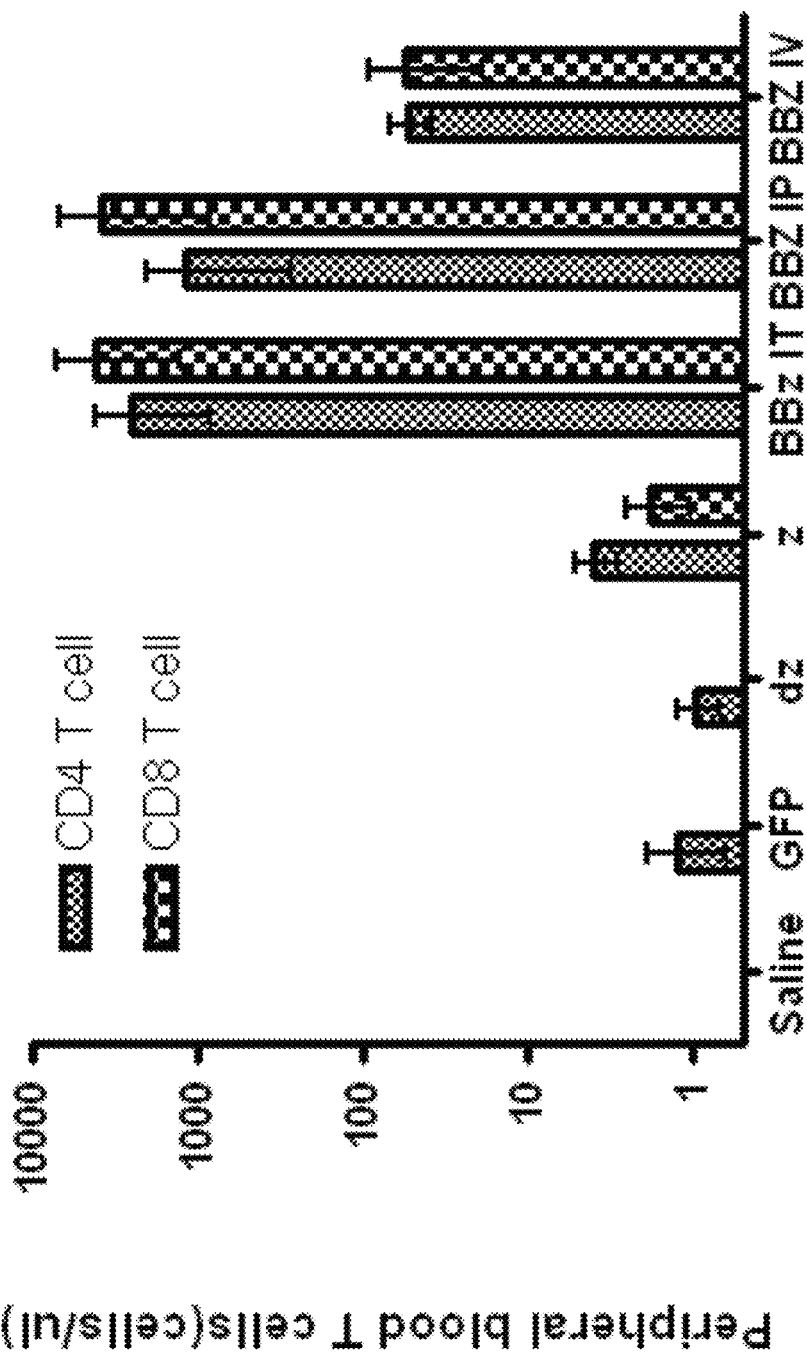
FIG. 13 is a graph showing that 4-1BB signals enhance the persistence of human T lymphocytes in vivo. Peripheral blood was obtained from retro-orbital bleeding on day 74 and stained for the presence of human CD45, CD4, and CD8 T cells. After gating on the human CD45+ population, the CD4+ and CD8+ subsets were quantified using TruCount tubes (BD Biosciences). Persistence was greatest in the BBz group independent of route of injection.

Next, the persistence of the engineered T cells in all mice was determined. Peripheral blood was obtained on day 74, 4 weeks after the last adoptive T cell transfer, and quantified for the presence of CD4 and CD8 T cells. The CD4+ and CD8+ T cell counts were highest in mice after injection with BBz CAR+ T cells by IT, IP and IV route compared to gfp, αFR CAR dz and the CD3zeta group (FIG. 13). Notably, the counts of CD4+ and CD8+ T cells in BBz group was significantly higher than z group (P<0.01), while the total T cell counts in the z group is similar with other control groups including saline group without T cells injection (p>0.05).

Example 7: Antigen Specific Model

Having shown that αFR CAR containing 4-1 BB mediate enhanced survive of T cells and increased anti-tumor activity in vivo, it was next sought to determine whether the αFR CAR anti-tumor activity is antigen specific. A CD19 specific CAR also containing 4-1BB singling domain was evaluated in the xenograft model. On week 6 after establishing the tumor, tumor-bearing mice were treated with intratumoral injections of $20 \times 10^6$ T cells (~40%-50% transgene positive) on day 40 and 45. Following treatment, a rapid reduction in tumor mass was observed in αFR CAR BBz group (FIG. 14A). In contrast, the tumor grew progressively in mice treated with T cells expressing GFP or CD19 CAR group. Thus, αFR CAR BBz eradication of SKOV3 tumor is antigen-specific because the CD19 CAR also containing a 4-1BB co-stimulatory signaling domain displayed no anti-tumor activity (FIGS. 14A-14B). Mice treated with intratumoral αFR CAR BBz had significantly higher (P<0.05) T-cell counts than the intratumoral anti-CD19 group, suggesting that tumor antigen drives the expansion of the adoptively transferred T cells in vivo (FIG. 14C).

Example 8: Intraperitoneal Model of Human Ovarian Cancer

Figures 15A, 15B, 15C:
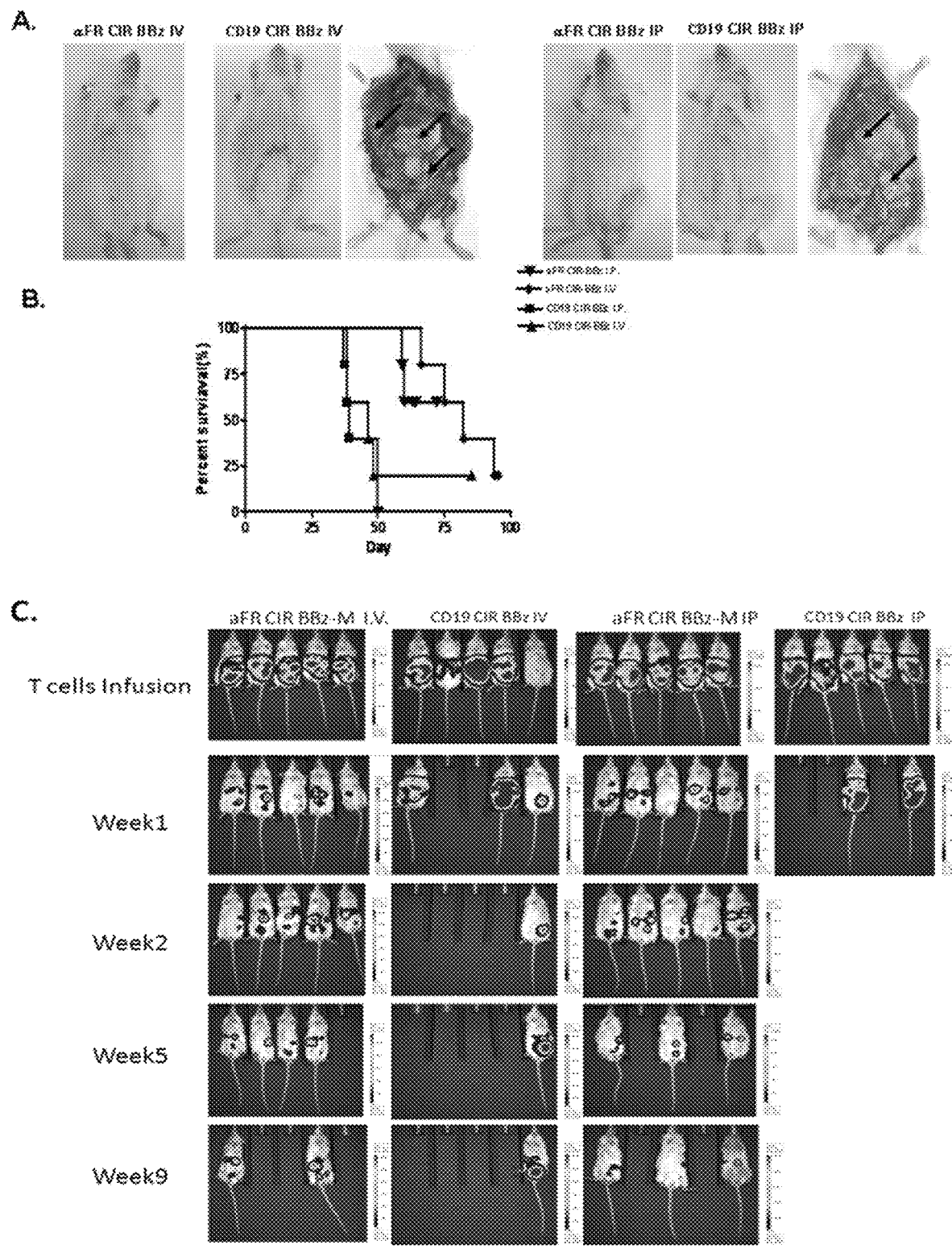
FIGS. 15A-15C are a series of images showing that αFR CAR BBz specific T cells inhibit tumor growth and ascites formation in SKOV3 murine model of peritoneal carcinomatosis.

In the previous experiment, it was demonstrated that local injection of CAR T cells results in eradication of established tumor in vivo. It was further determined the antitumor activity of αFR-specific T cells in an intraperitoneal model, because ovarian cancer is a disease usually confined to the peritoneal cavity. After 30 days, IP inoculation $5 \times 10^6$ SKOV3Luc cells efficiently produced peritoneal carcinomatosis (FIG. 15.C). A swollen abdomen, indicative of ascites formation and heavily peritoneal carcinomatosis, was observed within 1 to 3 weeks after T cells expressing CD19 CAR BBz transfer via IV or IP route (FIG. 15.A). These mice developed marked bloody ascites (5~8 ml) and multiple nodular peritoneal tumors and had to be euthanized within 1 to 3 weeks after T cell injection due to abdominal distention. While all the mice treated with αFR CAR BBz did not form ascites and exhibited enhanced survival (FIG. 15B.). 60% (3/5) and 40% (2/5) mice bearing SKOV3 tumor remain alive by 10 weeks following αFR CAR BBz T cell transfer via IP and IV route, respectively. Thus, αFR CAR BBz specific T cells inhibit tumor growth and ascites formation in SKOV3 murine model of peritoneal carcinomatosis. Importantly, αFR CAR BBz specific T cells improve the survival time.

Example 9: Lung Metastatic Model of Human Ovarian Cancer

Figure 16:
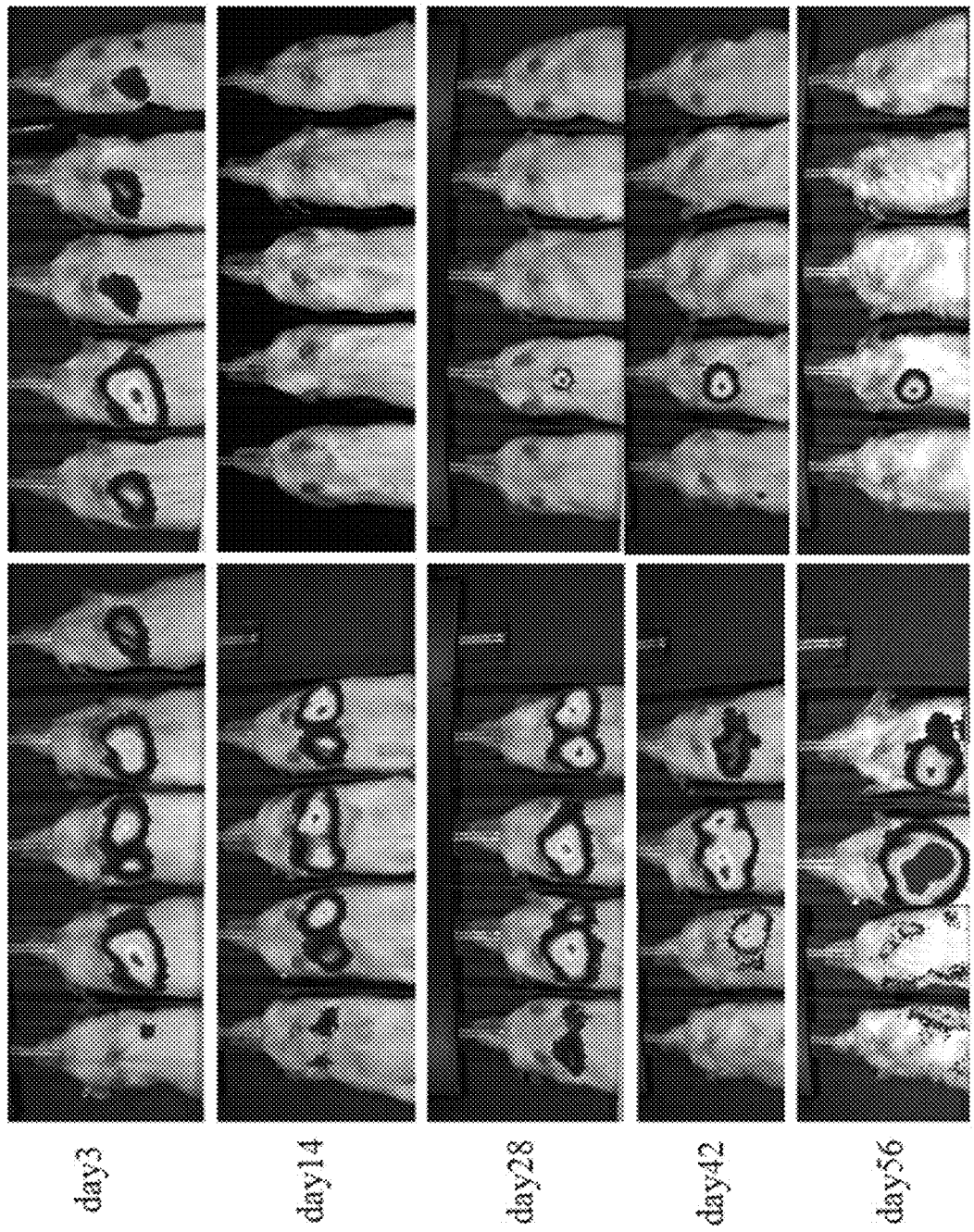
FIG. 16 is a series of images showing that the adoptive transfer of αFR CAR BBz-specific T cells induces regression of ovarian cancer lung metastasis. While tumors regressed in response to injection of αFR-specific T cells, tumors grew progressively in CD19-specific T cells treated mice.

Occasionally, ovarian cancer patients present with aggressive disease, manifested by parenchymal liver or lung metastases, or develop metastases to such distant sites as the brain during disease progression. For the generation of a lung metastatic model of ovarian cancer, 8-12-week-old NOG mice were i.v. injected with $2 \times 10^6$ SKOV3 Luc cells (in 200 μl PBS) on day 0. After evidence of tumor establishment in the lungs on day 3, animals were treated with tail-vein injections of $15 \times 10^6$ either αFR CAR BBz T cells or CD19 CAR BBz T cells on day 3 and day 8 (in 200 μl PBS). This route tumor inoculation established progressive lung metastases in 100% of mice, as judged by bioluminescence imaging (FIG. 16 Top panel). In CD19 CAR T cells treated mice, tumors progressively grew in all animals. In contrast, injections of αFR CAR BBz-specific T cells resulted in regression of lung metastasis in all treated animals (n=5) (FIG. 16 day 14). 80% (4/5) of mice had no evidence of tumor recurrence after >2 months of follow-up. One animal had recurrent lung metastasis and was euthanized on day 70. Thus, adoptive transfer of αFR-specific T cells offers the possibility of regression of lung metastases.

Example 10: Relevance to Human Application

The above studies demonstrate the functionality of the constructs in vivo and in vitro. The multiple human ovarian cancer cell lines such as SKOV3, A1847, OVCAR3, C30, A2780 and PEO-1 were used in vitro experiment (see FIG. 9C). This approach was also in a preclinical xenograft model using human ovarian cancer cell line SKOV3 Luc. A possible difference between the in vitro system and the proposed human treatment is that the in vitro experiments were done on cell lines, which may not reflect the tumor cells in vivo.

The ovarian cancer model used is an orthotopic human xenograft and thus similar to the human ovarian cancer disease that spreads intraperitoneally. A possible difference with human disease is that this model is extremely aggressive. Another obvious difference is that the model is developed in an immunodeficient host, while human ovarian cancer develops in immunocompetent individuals, although patients with ovarian cancer may exhibit elements of suppression of cellular immunity.

Example 11: Minimal Level of Gene Transfer and/or Expression that is Estimated to be Necessary for the Gene Transfer Protocol to be Successful in Humans and Determination of Minimal Level A copy number release specification of 0.2-5 for the final cellular product has been achieved. This specification is above what has been routinely achieved with lentiviral vectors, and the number represents a range that is expected to demonstrate activity while minimizing unnecessary risk from extensive insertions. For Stratum 1, a single infusion of $3 \times 10^7$ CAR T cells/m² I.T. can be administered as the lowest dose where as for Stratum 2, CAR T cells dosed by I.V. infusion using a "split dose" with $3 \times 10^8$ CAR T cells/m² as the lowest dose. Final products can be tested for percent transduction by flow cytometry, and the numbers of transduced cells can be recorded after harvest and at baseline, immediately after infusion.

A major goal of the clinical trial is to establish an optimal biologic dose for the αFR-CAR T cells. The purpose of this pilot trial is to evaluate the safety, tolerability and differential survival and trafficking of cells modified with the αFR-CAR. The numbers of patients proposed can be sufficient to reach this endpoint, as supported by the statistical analysis plan in the protocol.

Example 12: Effectiveness of the Delivery System in Achieving the Minimally Required Level of Gene Transfer and Expression For data demonstrating the in vitro efficiency of transduction of the αFR constructs, please refer to FIGS. 8A-8B, for animal data please refer to FIGS. 11A-11B, 12A-12D, 13, and 14A-14C. Efficient transduction of CD3/28 stimulated autologous T cells using lentiviral vector technology at clinical scale using a lentiviral vector in a pilot clinical trial has been demonstrated. A similar method can be used for the proposed study.

Example 13: Gene-Specific Expression

The lentiviral vector used for this study only encodes a single protein, which is the transgene of interest. Therefore, no other genes are expressed by the vector other than the transgene. In previous lentiviral vector study, a conditionally replicating viral vector, which used the native LTRs as promoters was used. There is very low basal activity in these promoters in the absence of tat, and therefore little read through into neighboring genes was expected, except in the context of HIV infection. An analysis on insertion site patterns in the five patients treated was performed on the original transduced cellular product. It was found that the vector inserted into genes in a pattern similar to that observed with other lentiviral vectors, including SIN vectors. The location of insertion was as expected for lentiviruses, which is predominantly in gene-rich regions (FIG. 3b of Levine et al, 2006). The vector inserted into transcriptionally active genes distributed throughout the coding region. These findings were confirmed in a more recent publication evaluating the insertion site patterns longitudinally in patients who received lentiviral vector transduced T cells. No selection for integration sites was detected indicating that there is no functional modification of onco- or tumor suppressor genes.

The vector used in the proposed study can be a SIN vector with a constitutively active internal promoter as described in FIGS. 6 and 7. A recent study evaluated transcriptional activity of SIN vectors and their effect on activation of oncogenes, in direct comparison to a murine retroviral vector with intact LTRs, in the context of a tumor prone mouse model. Molecular analysis of the genes in tumors developing in the mice did not support oncogene transcriptional activation by the SIN vectors, although the murine retroviral vectors induced oncogene activation in myeloid tumor subsets. This is a result of a greater enhancer effect from the MLV LTR, and the insertion pattern of the MLV vector, which dominates in the 5' control region of genes where it is more likely to modulate gene expression.

Although transcriptional activation of neighboring genes is possible in cells transduced with SIN lentiviral vectors, the frequency of the event appears to be much lower than with MLV vectors. It is worthwhile to note that the natural experiment has been conducted in HIV infection, where T cell leukemia is not a known side effect of infection with the wild type lentivirus.

Example 14: Cell Expression of DNA Insert and Percentage of Normal Activity

Expression of the transgene is under the control of the ubiquitous mammalian ef-1α promoter which has previously been shown to have optimal transgene expression in T cells, and therefore expression in all transduced cells was observed.

The transduced T-cells ready for infusion are biologically active. In preclinical data in NOG mice, expression of αFR constructs in transduced cells persisted in the mouse models till day 74 (see FIG. 13). In patients, persistence of transduced T cells by monitoring peripheral blood by both PCR and flow cytometry can be tested throughout the trial.

Example 15: Gene Mis-Expression

An advantage of the ex vivo manufacturing process is that the cells exposed to the vector can be carefully controlled. As a result, the αFR CAR constructs can only be expressed in cells targeted by the vector during cell processing. Since the T lymphocytes are isolated by negative selection, a small percentage of monocytes and B cells can be present in the culture during transduction. Monocytes are not present in the final product but a small percentage of B cells may remain (<2%).

In the first lentiviral vector trial, the phenotype of the final product averaged 93.4% (range 80 to >99%) CD3+ T cells. A similar target population in the present protocol is expected.

Example 16: Production of Retroviral Particles 293 cells and primary T cells have been transduced with the lentiviral vector preparation. The vector is a third generation self inactivating (SIN) vector and does not contain any viral proteins and is replication incompetent. Therefore, no infectious particles are produced by cells that have been transduced with the vector.

Vector is produced in 293T cells by transient transfection. The release test for the lentiviral vector preparation includes a sensitive biological assay for a replication competent lentivirus (RCL). Although the chances of generation of an RCL are negligible due to the lack of accessory proteins and homology regions in the production system, this final biological assay provides functional evidence to the lack of any replicating moiety in the vector preparation.

To date, no RCL has been detected in any GMP vector lots from prior and ongoing clinical trials. More importantly, there is no evidence of RCL in any of the 23 patients that have been treated so far with lentiviral vector modified cells. Development lots and GMP lots of the vectors for the proposed study are in progress and can be tested for RCL in accordance with FDA Guidelines.

Figure 17:
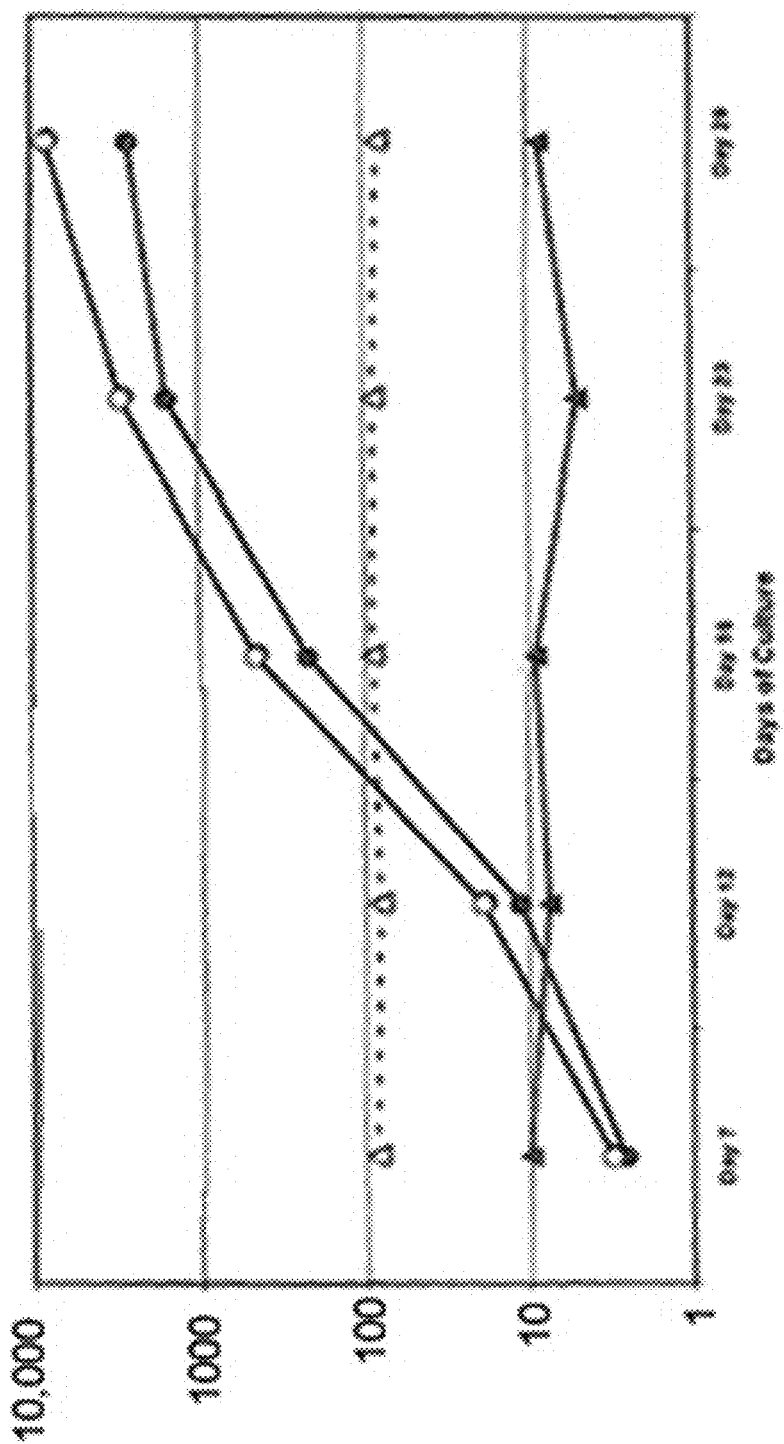
FIG. 17 is a graph showing that CD4 T cells isolated from a healthy donor were transduced at an MOT of 20 with a GFP-expressing HIV derived lentiviral vector, and cultured for 29 days. The X-axis represents fold-expansion (circles) or percent GFP expression (triangles). Transduced cells are open symbols and mock transduced cells are closed symbols.

For the previous clinical study using a conditionally replicating viral vector, the stability of the vector in primary CD4 T cells was examined and it was demonstrated that the vector copy number is stable for the duration of the experiment (FIG. 17). If significant rearrangement of the vector had occurred, then this would have been reflected in changes in the vector copy number. It is important to note that the vector copy number in the experiment remained stable even though the cells expanded over 1000-fold, since these experiments showed no decrease in vector copy number, as measured by TaqMan PCR (sensitivity of 1 copy per reaction that contains 10,000 to 30,000 cells).

A stability study for this vector was also carried out in primary T cells to evaluate the stability of the vector from production to transduction (i.e. a single reverse transcription step). Sequencing of the entire vector genome showed 100% fidelity between the production vector and the provirus in the transduced cells. Although the error rate for reverse transcription is about 1 in 10,000, resulting in approximately 1 error on average for every 2 proviruses, when a transduced cellular population is taken together, such mutations likely fall into the background as noise, thus providing an overall picture of 100% fidelity. Since there is only a single round of reverse transcription for each vector, the effect of the mutation rate on the function of the transcript should be negligible. In order to minimize instability of the vector, the αFR-CAR vectors have been designed such that they have no direct or inverted repeat elements.

No information exists as to whether these vectors could recombine with an endogenous retro-element present in human cells. However, considerable knowledge exists about the parental wt-HIV genome and how it replicates in human cells. To date there has been no description of a productive recombination event between wt-HIV and an endogenous retroviral element, even though 40 million humans are infected with the virus. Given the occurrence of this hypothetical recombination event, the issue becomes whether it would result in the generation of a recombinant with greater pathogenicity than wt-HIV. If this occurs, then it would likely have already occurred in the infected population. The fact that no such event has been described in the worldwide infected population suggests that if a recombination event between wt-HIV and an endogenous sequence occurs, then the resulting recombinant is rare or is not pathogenic in humans.

Example 17: Laboratory Evidence Concerning Potential Harmful Effects of the Transfer (e.g., Development of Neoplasia, Harmful Mutations, Regeneration of Infectious Particles, or Immune Responses)

To date there are no reports of tumorigenesis caused by an HIV-derived lentiviral vector. A recent report by Montini et al (Montini et al., 2006) provides evidence supporting the relative biosafety of SIN lentiviral vectors in terms of genotoxicity. Although it remains theoretically possible that HIV-derived lentiviral vectors could cause insertional oncogenesis, to date no data exist to support this theory.

The vector used in the proposed studies is a SIN vector, which has been meticulously designed to contain only the minimal genetic elements required for function, and no vector proteins for maximum Biosafety (Dull et al., 1998). Vector is manufactured and purified under good manufacturing conditions, in a manner consistent with FDA requirements for purity as specified in the 2006 FDA Guidance on RCR testing, the US Pharmacopeia Guidance on Cell and Gene Therapy Products, and the CFR regulations on Pharmaceutical and Bulk Chemical GMPs.

In the present application, the vector is used ex vivo and therefore is less likely to induce an immune response. However, in the ongoing Phase I/II clinical trial, it was observed that generation of antibodies to the vector envelope protein in 50% of patients after the third dose of vector modified cells. Since the dosing schedule is biweekly, it is possible in some or all patients that the immune response was generated as early as by the second infusion. It was not believed that a single infusion would generate an antibody response since none of the patients in the single dose Phase I clinical study became positive for VSV-G Ab (Levine et al., 2006). Generation of antibody to VSV-G did not impact the persistence of vector modified cells in the patients, nor did it coincide with adverse events in the patients. Therefore, the development of VSV-G antibodies has little to no detectable clinical impact. In the proposed clinical study, two infusions per patient are given. Therefore, it is possible to observe an antibody response to VSV-G in this trial.

Example 18: Animal Studies for Pathogenicity

Extensive biodistribution and biotoxicity studies were performed for the first lentiviral vector clinical trial. For the biodistribution study, a total of 192 mice were divided into four groups of 48 mice who received a 0.3 ml tail vein injection of the following: infusion media alone (group 1), 20 million mock transduced human T cells (group 2), 300,000 vector transduced human T cells (group 3) or 20 million vector transduced human T cells (group 4). Male and female mice were tested separately. Mice were analyzed at days 2, 15, 30, 91, and 123, and mice were evaluated for in-life parameters which included mortality, clinical observations/physical examinations, and body weights. The study showed that vector transduced human T cells had no effect on mortality, clinical observations or body weights. No mice developed T cell tumors. The presence of vector sequences was assessed by PCR. On days 2 and 30, vector sequences were present in all tissues tested from groups 3 and 4. By day 91, only lung, liver, spleen and tail from four mice were positive for vector, and by day 123 no vector was detected (Table 1).

TABLE 1

Results from a biodistribution study evaluating lentiviral vector-transduced human T cells in immunodeficient mice. Shown are the results from the mice given the highest dose of transduced cells (20 million human CD4 cells per mouse i.v.) as described in the text. Male and female mice are combined for n = 10 per timepoint.

| Tissue | Day 2 | Day 30 | Day 91 | Day 123 |
| --- | --- | --- | --- | --- |
| Heart | 100% | 30% | * | * |
| Gonads (testes/ovaries) | 80% | 50% | * | * |
| Liver | 100% | 90% | 10% | * |
| Inguinal lymph node | 90% | 20% | * | * |
| Bone Marrow | 100% | * | * | * |
| Lung | 100% | 40% | * | * |
| Spleen | 100% | 10% | 10% | * |
| Tail | 100% | 40% | 10% | * |
| Blood | 100% | 40% | * | * |

* no vector detected.

In other experiments, the biotoxicity of lentiviral vector modified T cells was evaluated a total of 144 mice divided into four groups of 36 mice per group who received a tail vein injection of 0.3 ml divided into the same groups as listed above. Male and female mice were tested separately. Mice were evaluated for mortality, clinical observations/physical examinations, body weights, clinical pathology results, gross pathology findings, organ weight data, bone marrow evaluation, and histopathology results. The results from this study were that vector transduced human T cells were not associated with any toxicity, and had no effect on any of the parameters evaluated.

The vector used for the proposed study is different in structure and payload, however the lentiviral transduced cellular vehicle (human T cells) is anticipated to behave in a similar manner in the mouse model.

The genotoxicity of SIN vectors has recently been tested in a tumor prone mouse model, and no toxicity could be detected within the sensitivity of the model, although toxicity with a murine retrovirus vector was detected. Studies for tolerability of the αFR-CAR cells can only be accurately determined in an early phase clinical trial, as even in the humanized mouse model, antigen, T cell trafficking, and tumor antigen expression across various tissues can be different in the animal model.

There is no evidence to support vector DNA mobilizing or entering untreated cells. In the biodistribution study described above, the vector sequence was only detected in vivo in mice in conjunction with human cell markers, indicating that it did not mobilized to non-targeted cells.

Gonads in mice did not have detectable vector sequences at days 91 or 123 (end of study) (Table 1). This can be evaluated as well in the planned biotoxicity and biodistribution study for the αFR CAR.

All preclinical animal studies have been conducted in the immunodeficient NOD/SCIDγ−/− (NSG) human xenotransplantation animal model.

Example 19: In Vivo Persistence, Tumor Localization, and Antitumor Activity of CAR-Engineered T Cells is Enhanced by Costimulatory Signaling Through CD137 (4-1BB)

Human T cells engineered to express a chimeric antigen receptor (CAR) specific for folate receptor-α (FRα) have shown robust antitumor activity against epithelial cancers in vitro but not in the clinic because of their inability to persist and home to tumor in vivo. In this study, CARs were constructed containing a FRα-specific scFv (MOv19) coupled to the T-cell receptor CD3ζ chain signaling module alone (MOv19-ζ) or in combination with the CD137 (4-1BB) costimulatory motif in tandem (MOv19-BBζ). Primary human T cells transduced to express conventional MOv19-ζ or costimulated MOv19-BBζ CARs secreted various proinflammatory cytokines, and exerted cytotoxic function when co-cultured with FRα⁺ tumor cells in vitro. However, only transfer of human T cells expressing the costimulated MOv19-BBζ CAR mediated tumor regression in immunodeficient mice bearing large, established FRα⁺ human cancer. MOv19-BBζ CAR T-cell infusion mediated tumor regression in models of metastatic intraperitoneal, subcutaneous, and lung-involved human ovarian cancer. Importantly, tumor response was associated with the selective survival and tumor localization of human T cells in vivo and was only observed in mice receiving costimulated MOv19-BBζ CAR T cells. T-cell persistence and antitumor activity were primarily antigen-driven; however, antigen-independent CD137 signaling by CAR improved T-cell persistence but not antitumor activity in vivo. Results described herein show that anti-FRα CAR outfitted with CD137 costimulatory signaling in tandem overcome issues of T-cell persistence and tumor localization that limit the conventional FRα T-cell targeting strategy to provide potent antitumor activity in vivo.

As described herein, the issue of limited FRα-specific T-cell persistence and tumor activity in vivo is addressed through the introduction of the CD137 costimulatory signaling domain into a FRα-specific CAR and studied the role of CD137 signaling in FRα-directed CAR T-cell therapy of human cancer. Compared with "first-generation" CAR that provide CD3 signaling to T cells but lack cis costimulatory signaling capacity, T cells expressing FRα-specific CAR with a CD137 signaling domain in tandem showed minimally improved antitumor activity in vitro, but markedly superior tumor regression capacity in established human ovarian cancer xenograft models, which was associated with enhanced T-cell persistence and tumor localization in vivo. Tumor regression and T-cell persistence were both attainable by various routes of T-cell infusion, and intravenous (i.v.) cell infusion mediates the regression of human cancer in xenograft models of advanced intraperitoneal (i.p.), subcutaneous (s.c.), and lung-involved metastatic disease. T-cell persistence and tumor activity in vivo were largely antigen-driven; however, provision of CD137 signaling in the absence of specific antigen recognition by CAR could improve T-cell persistence but not antitumor activity in vivo. Incorporation of the CD137 signaling domain in FRα-specific CARs thus overcomes the limitation of past CAR approaches by improving the persistence of transferred T cells in vivo, and bolstering their accumulation in tumor and antitumor potency. The materials and methods employed in these experiments are now described.

Materials and Methods

Anti-FRα Chimeric Immune Receptor Construction

The chimeric immune receptor backbone constructs were generated as previously described (Carpenito et al., 2009, Proc Natl Acad Sci USA 106:3360-65). The anti-FRα scFv sequence was derived from MOv19 (Miotti et al., 1987, Int J Cancer 39: 297-303; Figini et al., 1998, Cancer Res 58(5):991-6), a monoclonal antibody directed against FRα. The MOv19 scFv has been fully characterized (Figini et al., 2009, Cancer Immunol Immunother 58(4):531-46; Melani et al., 1998, Cancer Res 58: 4146-54) and was amplified using the following primers:

```
                                       (SEQ ID NO: 24)
5'-GCGGGATCCTCTAGAGCGGCCCAGCCGGCCATGGCCCAGGTG-3'
(Bam-HI is underlined)
and
                                       (SEQ ID NO: 25)
5'-GCGGCTAGCGGCCGCCCGTTTTATTTCCAACTTTGTCCCCCC-3'
(Nhe-I is underlined)
``` and then cloned into the CAR backbone vector. The scFv PCR product was digested with BamHI and NheI endonucleases and gel purified before ligation into the pCLPS vector, a third generation self-inactivating CMV promoter based lentiviral expression vector based on pRRL-SIN-CMV-eGFP-WPRE (Dull et al., 1998, J Virol 72(11):8463-71). The anti-CD19-BBζ CAR construct has been previously described (Milone et al., 2009, Mol Ther 17:1453-64). High-titer lentiviral vectors were produced and concentrated 10-fold by ultracentrifugation for 3 h at 26,000 rpm as previously described (Parry et al., 2003, J Immunol 171: 166-74).

Cell Lines

Lentivirus packaging was performed in the immortalized normal fetal renal 293T cell line purchased from ATCC. Human cell lines used in immune based assays include the established human ovarian cancer cell lines SKOV3, A1847, OVCAR3, C30, and PEO-1. For bioluminescence assays, target cancer cell lines were transfected to express firefly luciferase (fLuc), enriched by antibiotic selection positive expression by bioluminescence imaging. For specificity controls, the mouse malignant mesothelioma cell line, AE17 was transduced with lentivirus to express FRα(AE17.FRα). CD19-expressing K562 (CD19+K562) cells, a human erythroleukemic cell line, were obtained (Milone et al., 2009, Mol Ther 17:1453-64). 293T cells and tumor cell lines were maintained in RPMI-1640 (Invitrogen) supplemented with 10% (v/v) heat-inactivated FBS, 2 mM L-glutamine, 100 μg/mL penicillin and 100 U/mL streptomycin. All cell lines were routinely tested for mycoplasma contamination.

Human T Cells

Primary human CD4⁺ and CD8⁺ T cells, which were purchased from the Human Immunology Core at University of Pennsylvania, were isolated from healthy volunteer donors following leukapheresis by negative selection. All specimens were collected under a protocol approved by a University Institutional Review Board, and written informed consent was obtained from each donor. T cells were cultured in complete media (RPMI 1640 supplemented with 10% heat inactivated FBS, 100 U/mL penicillin, 100 μg/mL streptomycin sulfate, 10 mmol/L HEPES), and stimulated with anti-CD3 and anti-CD28 monoclonal antibodies (mAb)-coated beads (Invitrogen) as described (Levine et al., 1997, J Immunol 159:5921-30). Twelve to twenty-four hours after activation, T cells were transduced with lentiviral vectors at multiplicity of infection of approximately 5 to 10. CD4+ and CD8+ T cells used for in vivo experiments were mixed at 1:1 ratio, activated, and transduced. Human recombinant interleukin-2 (IL-2; Novartis) was added every other day to a 50 IU/mL final concentration and a cell density of $0.5 \times 10^6$ to $1 \times 10^6$ cells/mL was maintained. Once T cells seemed to rest down, as determined by both decreased growth kinetics and cell sizing by using the Multisizer 3 Coulter Counter (Beckman Coulter), engineered T-cell cultures were adjusted to equalize the frequency of transgene expressing cells prior to functional assays.

Flow Cytometric Analysis

The following MAbs were used for phenotypic analysis: APC-Cy7 Mouse Anti-Human CD3; FITC anti-human CD4; APC anti-human CD8; PE-anti human CD45. All mAbs were purchased from BD Biosciences PharMingen. In T cell transfer experiments, peripheral blood was obtained via retro-orbital bleeding and stained for the presence of human CD45, CD4, and CD8 T cells. After gating on the human CD45+ population, the CD4+ and CD8+ subsets were quantified using TruCount tubes (BD Biosciences) with known numbers of fluorescent beads as described in the manufacturer's instructions. Tumor cell surface expression of FRα was detected by Mov18/ZEL antibody (Enzo Life Sciences). FRα specific CAR expression was detected by PE conjugated goat anti-mouse IgG F(ab')$_2$ (specific for scFvs of murine origin) that was purchased from Jackson ImmunoResearch. For intracellular staining, cells were fixed, permeabilized, and stained with PE-conjugated anti-Bcl-X$_L$ antibody (Southern Biotech). Isotype matched control Abs were used in all analyses. Flow cytometric data were analyzed by FlowJo software.

Cytokine Release Assays

Cytokine release assays were performed by co-culture of $1 \times 10^5$ T cells with $1 \times 10^5$ target cells per well in triplicate in 96-well round bottom plates in a final volume of 200 μl of T cell media. After 20-24 hr, co-culture supernatants were assayed for presence of IFN-γ using an ELISA Kit, according to manufacturer's instructions (Biolegend). Values represent the mean of triplicate wells. IL-2, IL-4, IL-10, TNF-α cytokines were measured by flow cytometry using Cytokine Bead Array, according to manufacturer's instructions (BD Biosciences).

Cytotoxicity Assays

For the cell based bioluminescence assay, $5 \times 10^4$ firefly Luciferase expressing (fLuc+) tumor cells were cultured with complete media in the presence of different ratios of transduced T cells using a 96-well Microplate (BD Biosciences). After incubation for 18-20 hours at 37° C., each well was filled with 50 μl DPBS resuspended with 1 μl D-luciferin (0.015 g/ml) and imaged using a Xenogen IVIS Spectrum. Percent tumor cell viability was calculated as the mean luminescence of the experimental sample minus background divided by the mean luminescence of the input number of target cells used in the assay minus background times 100. All data are represented as a mean of triplicate wells. $^{51}$Cr release assays were performed as described (Johnson et al., 2006, J Immunol 177(9):6548-59). Target cells were labeled with 100 μCi 51Cr at 37° C. for 1.5 hours. Target cells were washed three times in PBS, resuspended in CM at $10^5$ viable cells/mL and 1004 added per well of a 96-well V-bottom plate. Effector cells were washed twice in CM and added to wells at the given ratios. Plates were quickly centrifuged to settle cells, and incubated at 37° C. in a 5% CO$_2$ incubator for 4 or 8 hours after which time the supernatants were harvested and counted using a 1450 Microbeta Liquid Scintillation Counter (Perkin-Elmer). Percent specific lysis was calculated as (experimental−spontaneous lysis/maximal−spontaneous lysis) times 100. For gfp target cell lysis assays, transduced T cells were co-cultured at various effector to target ratios for 24 hrs with $5 \times 10^4$ gfp expressing AE17 or AE17.FRα cells and photographed under fluorescent microscopy. Target cell lysis was indicated by imaging reduction in gfp-labeled adherent tumor cells.

Xenograft Model of Ovarian Cancer

Mouse studies were carried out as previously described (Carpenito et al., 2009, Proc Natl Acad Sci USA 106:3360-5, Milone et al., 2009, Mol Ther 17:1453-64) with modifications detailed herein. All animals were obtained from the Stem Cell and Xenograft Core of the Abramson Cancer Center, University of Pennsylvania. Eight to 12-weekold NOD/SCID/γ-chain−/− (NSG) mice were bred, treated and maintained under pathogen-free conditions in-house under University of Pennsylvania IACUC approved protocols. For an established ovarian cancer model, 6 to 12-week-old female NSG mice were inoculated s.c. with $3 \times 10^6$ SKOV3 fLuc+ cells on the flank on day 0. After tumors become palpable at about 1 month, human primary T cell (CD4+ and CD8+ T cells used were mixed at 1:1 ratio) were activated, and transduced as described elsewhere herein. After 2 weeks T cell expansion, when the tumor burden was ~200-300 mm$^3$, mice were treated with T cells. The route, dose, and timing of T-cell injections are indicated elsewhere herein. Tumor dimensions were measured with calipers, and tumor volumes calculated using the formula V=½(length×width$^2$), where length is greatest longitudinal diameter and width is greatest transverse diameter. Animals were imaged prior to T cell transfer and about every week thereafter to evaluate tumor growth. Photon emission from fLuc+ cells was quantified using the "Living Image" software (Xenogen) for all in vivo experiments. Tumors were resected immediately after euthanasia approximately 40 days after first T cell dose for size measurement and immunohistochemistry. For the intraperitoneal model of ovarian cancer, 8 to 12-week-old NSG mice were injected i.p. with $5 \times 10^6$ SKOV3 fLuc+ cells. Thirty days after peritoneal inoculation, mice bearing well-established SKOV3 tumors were divided into groups and treated. Mice were sacrificed and necropsied when the mice became distressed and moribund. Lung metastases were established by injecting $2 \times 10^6$ SKOV3 fLuc+ cells into the tail vein of female NSG mice. After evidence of tumor establishment in the lungs on day 3, animals were treated with tail-vein injections of engineered T cells on day 3 and day 8. To monitor the extent of tumor progression, the mice were imaged weekly or biweekly and body weights of the mice were measured. In all models, 4-5 mice were randomized per group prior to treatment.

Bioluminescence Imaging

Tumor growth was also monitored by Bioluminescent imaging (BLI). BLI was done using Xenogen IVIS imaging system and the photons emitted from fLuc-expressing cells within the animal body were quantified using Living Image software (Xenogen). Briefly, mice bearing SKOV3 fLuc+ tumor cells were injected intraperitoneally with D-luciferin (150 mg/kg stock, 100 μL of D-luciferin per 10 grams of mouse body weight) suspended in PBS and imaged under isoflurane anesthesia after 5-10 minutes. A pseudocolor image representing light intensity (blue, least intense; red, most intense) was generated using Living Image. BLI findings were confirmed at necropsy.

Immunohistochemistry

Mice were euthanized by $CO_2$ inhalation and tumors were collected in Tissue-Tek O.C.T. Compound, and frozen at −80° C. A standard Strept-avidin horseradish immunoperoxidase method was used for human CD3 staining. Primary and secondary antibodies were diluted in buffer containing 10% normal goat serum. 7 μm cryosections were fixed in cold acetone for 5 min at 4° C. and blocked with Dako's (Carpentaria, Calif.) peroxidase blocking system for 10 minutes. Sequential incubations included the following: 10% normal goat serum (30 min at room temperature (RT)); primary rabbit anti-human CD3 monoclonal antibody (Thermo Scientific RM-9107) at 1:100 dilution (45 min. at RT); secondary biotinylated goat anti-rabbit antibody at 1:200 dilution (30 min at RT); strept-avidin-biotinylated horseradish peroxidase complex reagent (Dako) (30 min at RT); and three 5 minute washes in buffer after each incubations. Sections were then exposed to the chromagen DAB plus from Dako for 5 min at RT and counterstained with hematoxylin, dehydrated, cleared and mounted.

Statistical Analysis

Statistical analysis was carried out by 2-way repeated measures ANOVA for the tumor burden (tumor volume, photon counts). Student's t test was used to evaluate differences in absolute number of transferred T cells, cytokine secretion, and specific cytolysis. Kaplan-Meier survival curves were compared by using the log-rank test. GraphPad Prism 4.0 (GraphPad Software) was used for the statistical calculations. $P<0.05$ was considered significant.

The results of the experiments are now described.

CAR Construction

Figure 18A:
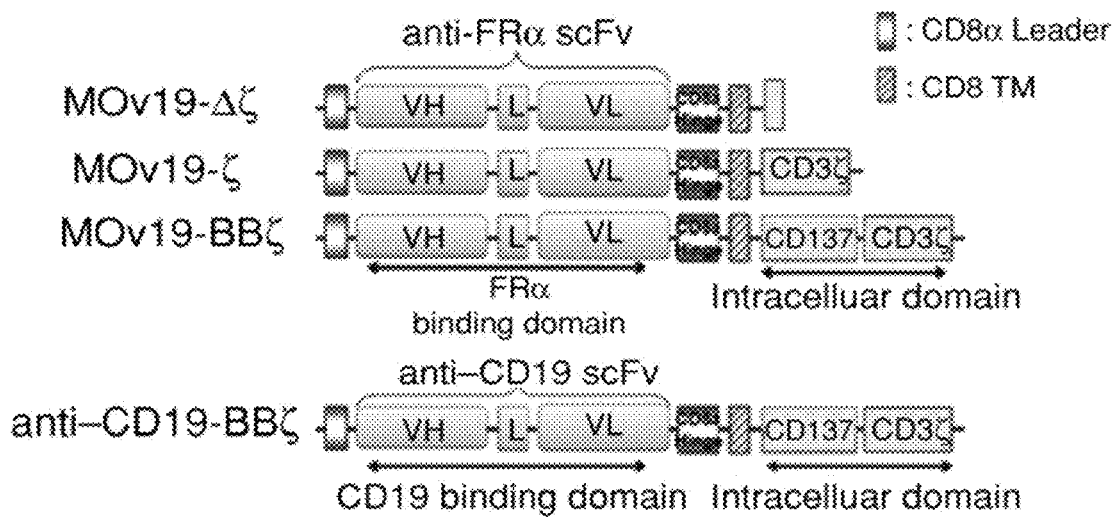
FIGS. 18A-18E are a series of plots and images depicting the generation and specific immune recognition by FRα CAR-transduced human T cells in vitro.
Figure 18B:
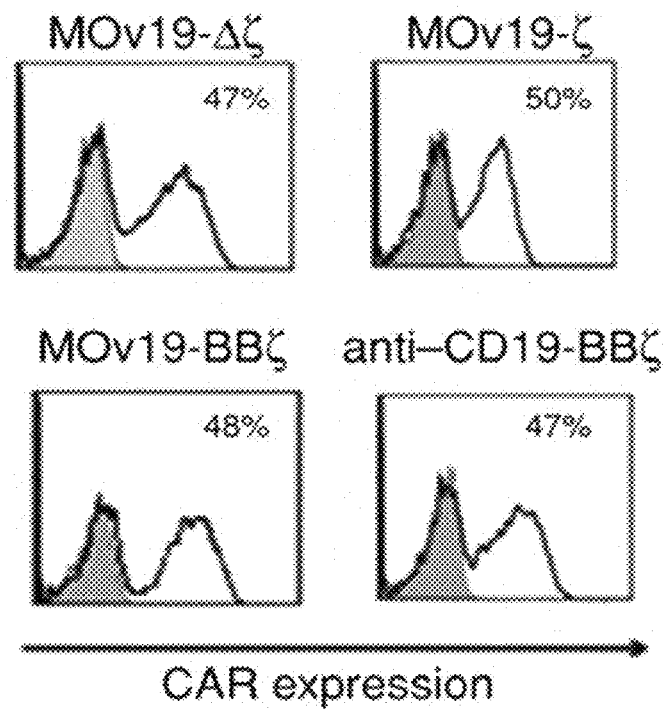

The mouse anti-human FRα-specific scFv MOv19 was selected on the basis of its high binding affinity for FRα ($10^8$-$10^9$ $M^{-1}$; refs. Miotti et al., 1987, Int J Cancer 39:297-303; Melani et al., 1998, Cancer Res 58:4146-54; Figini et al., 1998, Cancer Res 58:991-6). FRα CAR constructs were comprised of the MOv19 scFv linked to a CD8α hinge and transmembrane region, followed by a CD3 signaling moiety alone (MOv19-0 or in tandem with the CD137 intracellular signaling motif (MOv19-BBζ; FIG. 18A). A signaling deficient FRα-specific CAR containing a truncated CD3ζ intracellular domain (MOv19-Δζ) was designed to assess the contribution of CD3ζ signaling. An anti-CD19 CAR containing CD3ζ and CD137 signaling motifs in tandem (anti-CD19-BBζ) was used as an antigen specificity control (Milone et al., 2009, Mol Ther 17:1453-64). CAR constructs were subcloned into the pCLPS lentiviral vector where transgene expression is driven off the cytomegalovirus promoter. Using gene transfer technology established for clinical application, lentiviral vectors efficiently transduced primary human T cells to express the anti-FRα CAR (FIG. 18B). T-cell transduction efficiency, as assessed by flow cytometry, was equilibrated for all constructs at approximately 50% in all assays.

Primary Human FRα CAR T Cells Exert Antigen-Specific Function In Vitro

Figure 18C:
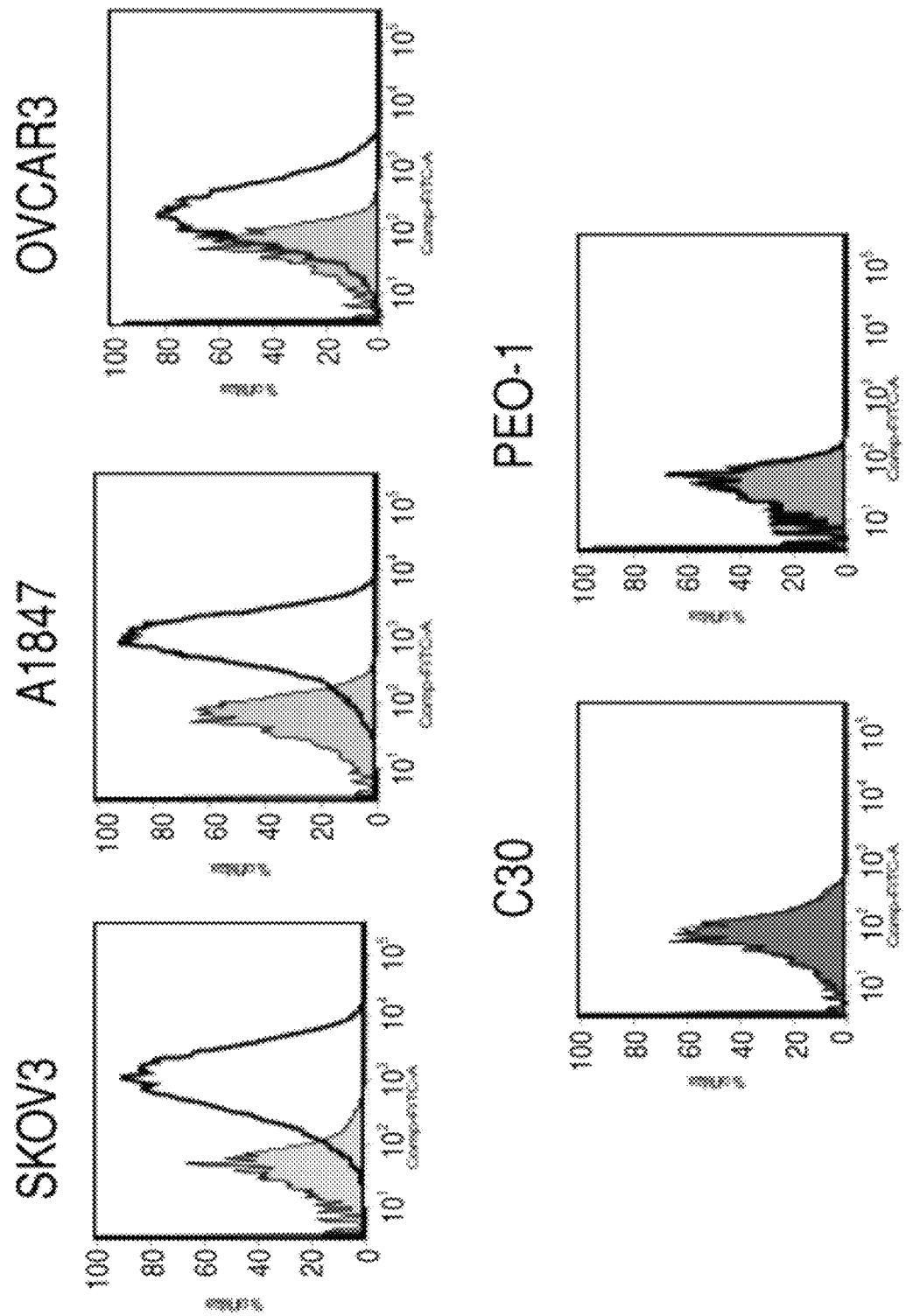
Figure 18D:
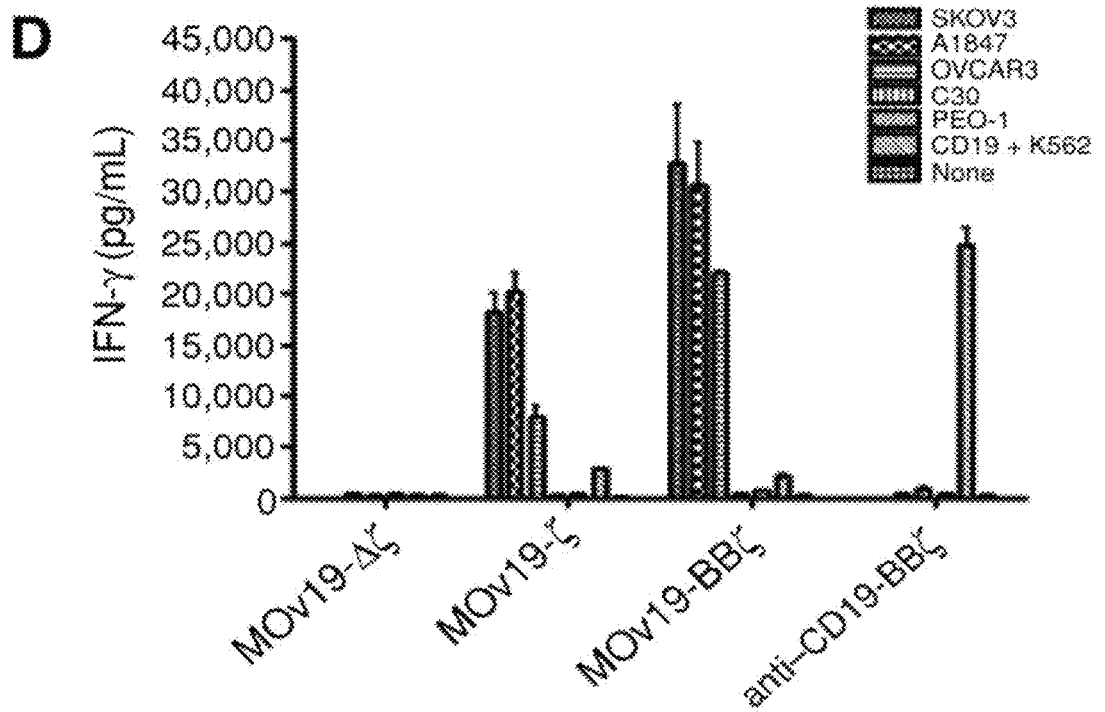
Figure 24:
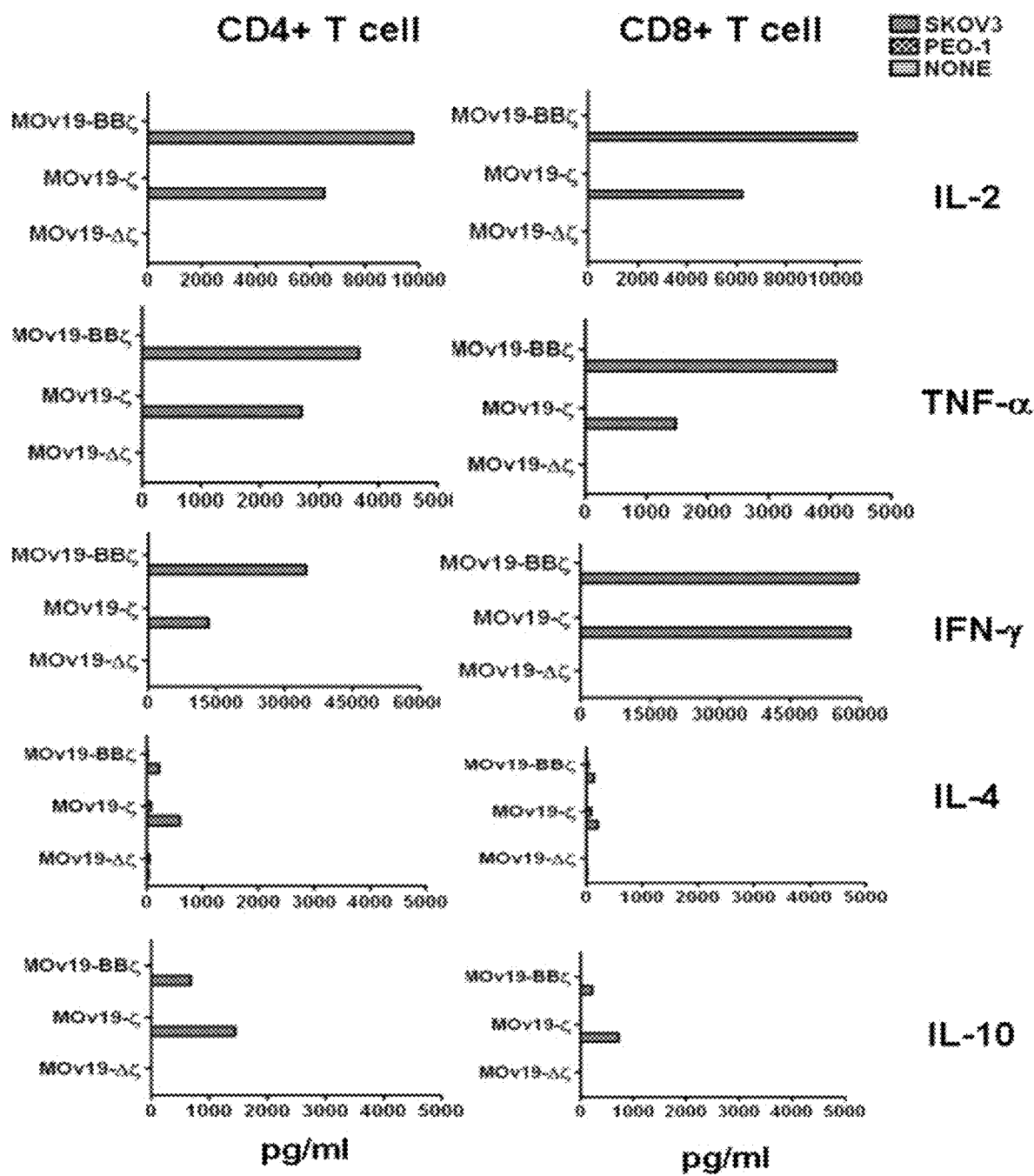
FIG. 24 is a series of graphs showing that primary human T cells transduced with MOv19-BBζ or MOv19-ζ preferentially produce Th1 cytokines after stimulation with FRα+ cancer cell lines. Transduced T cells ($1\times10^5$ CAR+ T cells) were cultured alone (none) or stimulated overnight with an equal number of human FRα+ SKOV3 or antigen negative PEO-1 ovarian cancer cells. Cell free supernatant from three independent cultures was harvested and pooled after ~20 hours of incubation, and the indicated human Th1/Th2 cytokines were quantified using cytometric bead array technology. Values represent IFN-γ concentration (pg/ml) for the indicated cytokine.

Because ovarian cancer frequently express FRα (Miotti et al., 1987, Int J Cancer 39:297-303), a panel of established human ovarian cancer cell lines that express surface FRα at varying levels (SKOV3, A1847, and OVCAR3) was selected for assays (FIG. 18C). Two ovarian cancer lines, C30 and PEO-1, were negative for FRα. Transduced T cells expressing MOv19-BBζ or MOv19-ζ CARs recognized FRα⁺ tumor lines and secreted high levels of IFN-γ, but not when stimulated with FRα lines (FIG. 18D). FRα-specific CAR T cells also secreted high levels of IL-2 and TNF-α when stimulated with FRα⁺ cancer cells and low but detectable levels of IL-4 and IL-10 (FIG. 24). MOv19 CARs functioned in both primary human CD4⁺ and CD8⁺ T cells. In all cases, MOv19-BBζ T cells secreted more IFN-γ than MOv19-ζ T cells after specific stimulation. CD19-BBζ CAR did not produce IFN-γ, except when co-incubated with K562 cells engineered to express surface CD19 antigen, and human T cells expressing MOv19-Δζ CAR did not secrete cytokine when stimulated with FRα⁺ cancer cells (FIG. 18D), showing that antigen specificity and CD3 signaling are required for CAR activity in T cells.

Figure 18E:
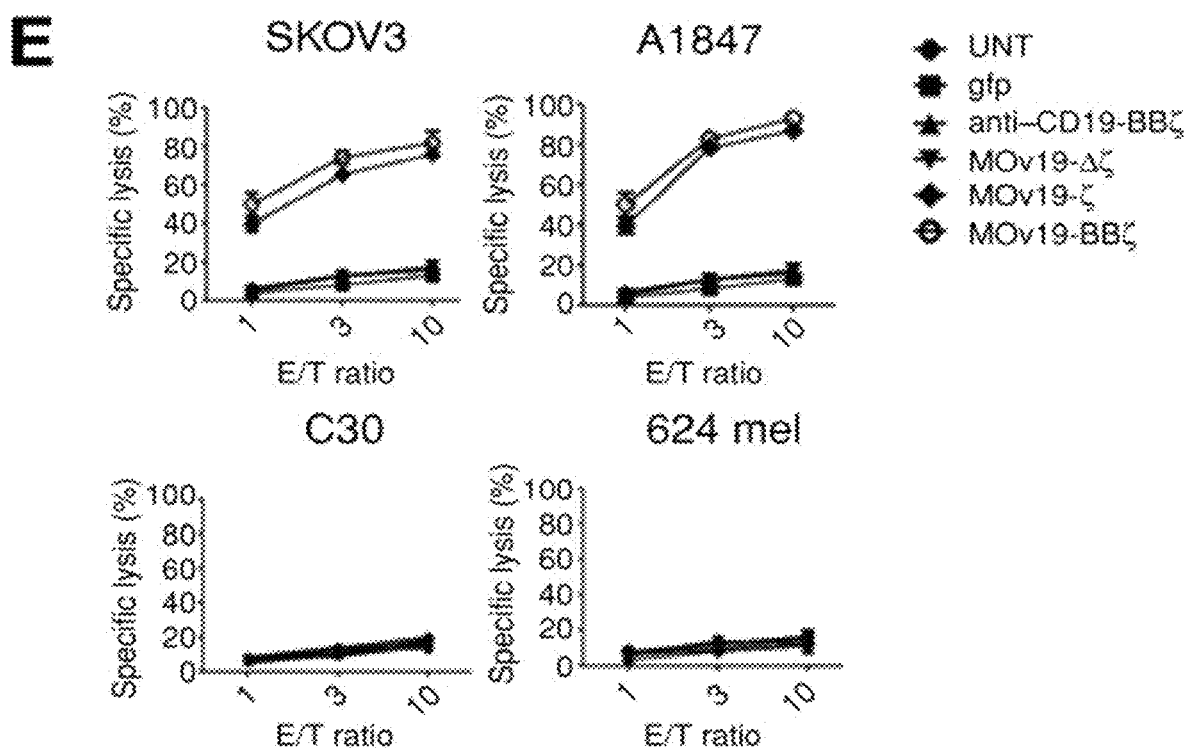
Figures 25A, 25B, 25C:
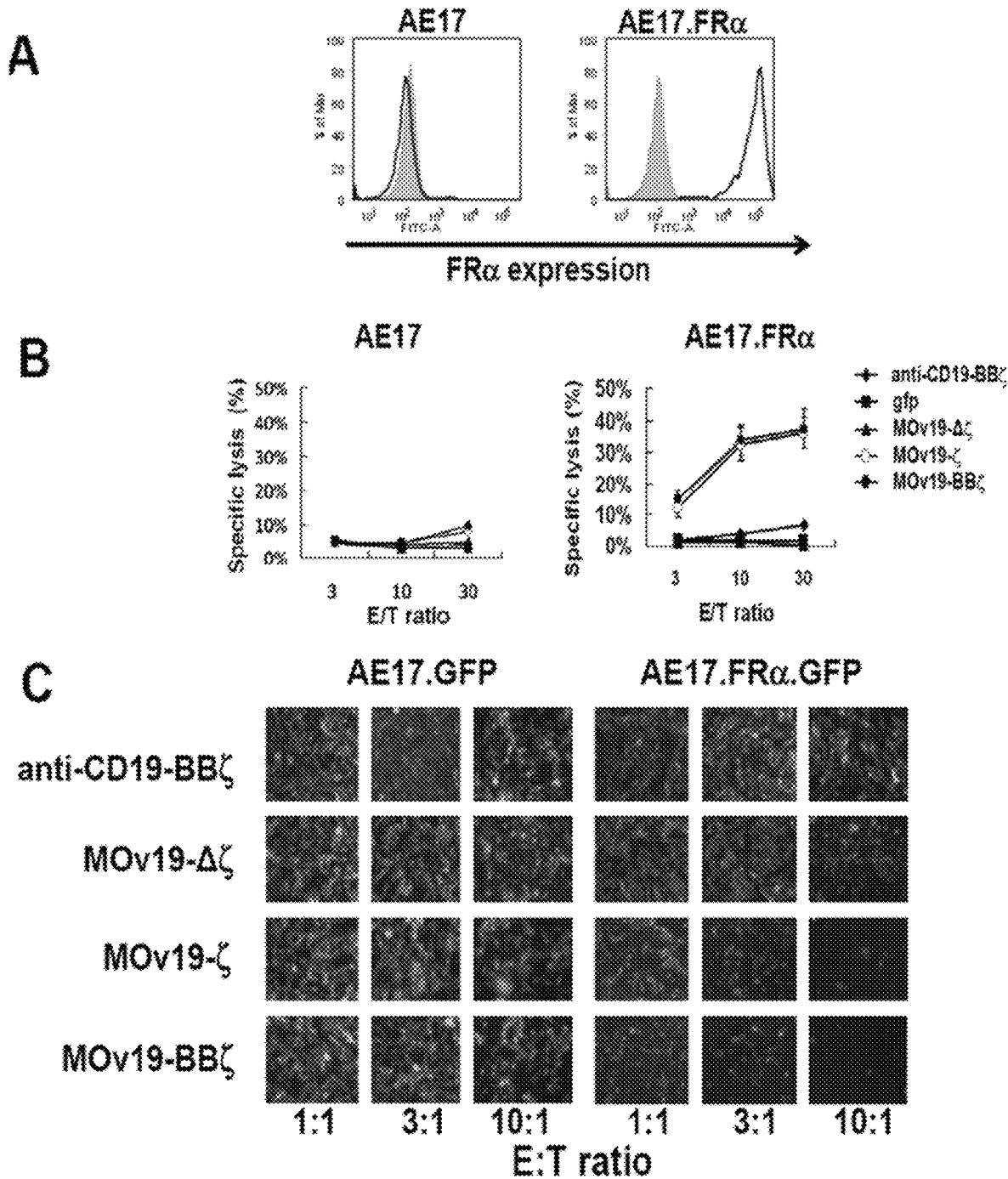
FIGS. 25A-25C are a series of plots and images showing that primary human T cells engineered to express FRα-specific CAR lyse FRα+ cell lines in vitro.
Figures 26A, 26B, 26C, 26D:
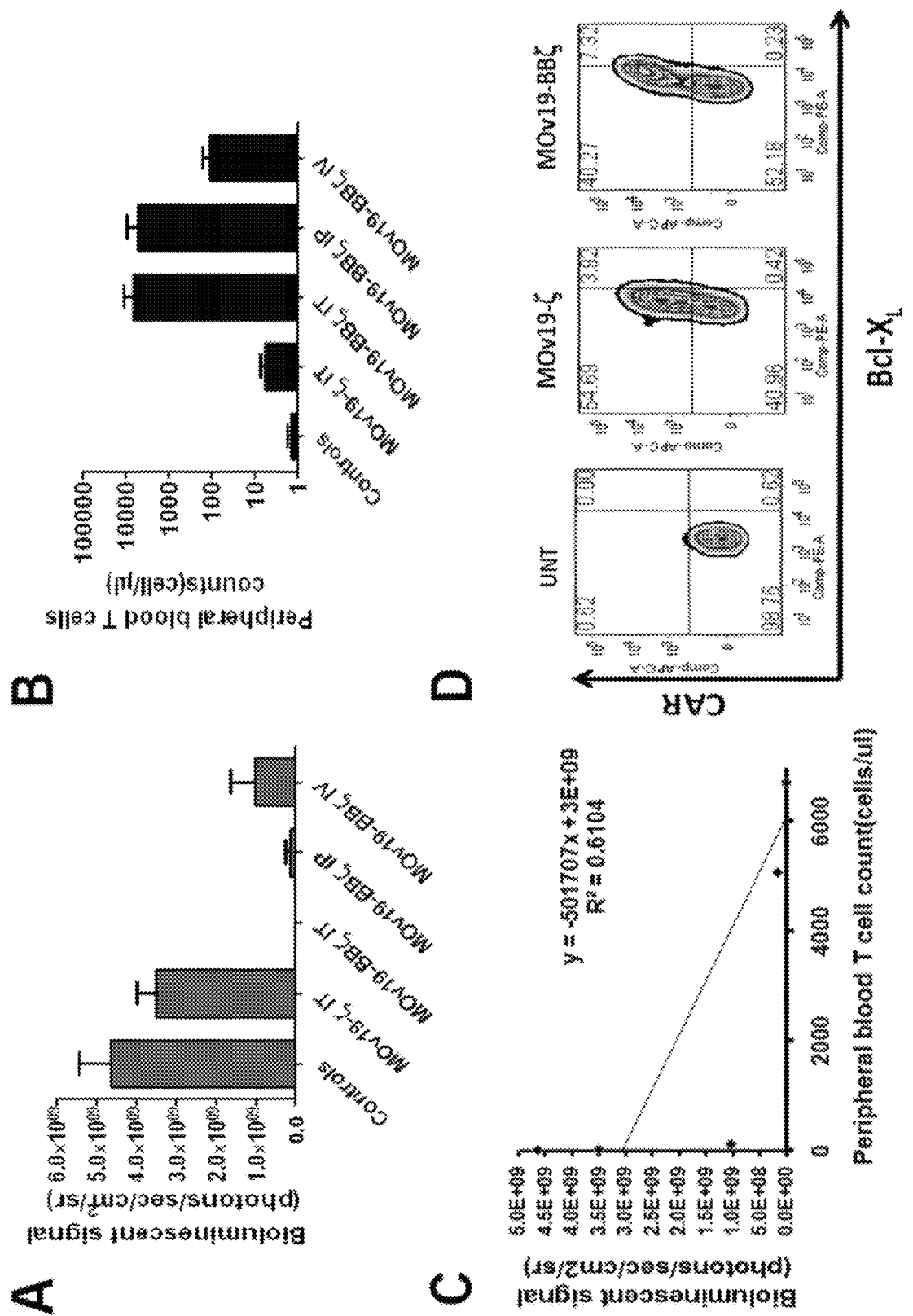
FIGS. 26A-26D are a series of plots showing that tumor regression is associated with the stable persistence of engineered human T cells in vivo and dependent upon provision of CD137 costimulatory signaling.

To interrogate antigen-specific cytolytic potential, anti-FRα CAR CD8⁺ T cells were co-cultured with FRα AE17 (Jackaman et al., 2003, J Immunol 171:5051-63), a mouse malignant mesothelioma cell line, or AE17.FRα (an AE17 line derivative transduced to express high surface levels of human FRα). In standard 4-hour chromium release and 24-hour bioluminescence assays, FRα-specific CAR T cells (MOv19-ζ and MOv19-BBζ) specifically lysed AE17.FRα cells but not the parental AE17 line (FIGS. 25A-25C). T cells expressing anti-CD19-BBζ, MOv19-Δζ, or green fluorescent protein (gfp) did not lyse AE17.FRα or AE17 cells. Consistent with cytokine production results, primary human CD8⁺ T cells expressing MOv19-ζ or MOv19-BBζ CAR directly and efficiently lysed FRα⁺ human ovarian cancer cell lines SKOV3 and A1847, but not FRα⁻ lines C30 or 624mel, a melanoma cell line (FIG. 18E). MOv19-BBζ CAR T cells exhibited increased cytotoxicity compared with MOv19-ζ CAR T cells, but not at a level of statistical significance. Thus, human T cells transduced with FRα-specific CAR specifically recognize FRα⁺ human and mouse cancer cells and exert MHC-unrestricted cytotoxic activity in vitro.

Antitumor Activity of Primary Human FRα CAR T Cells In Vivo

Figures 19A, 19B, 19C, 19D:
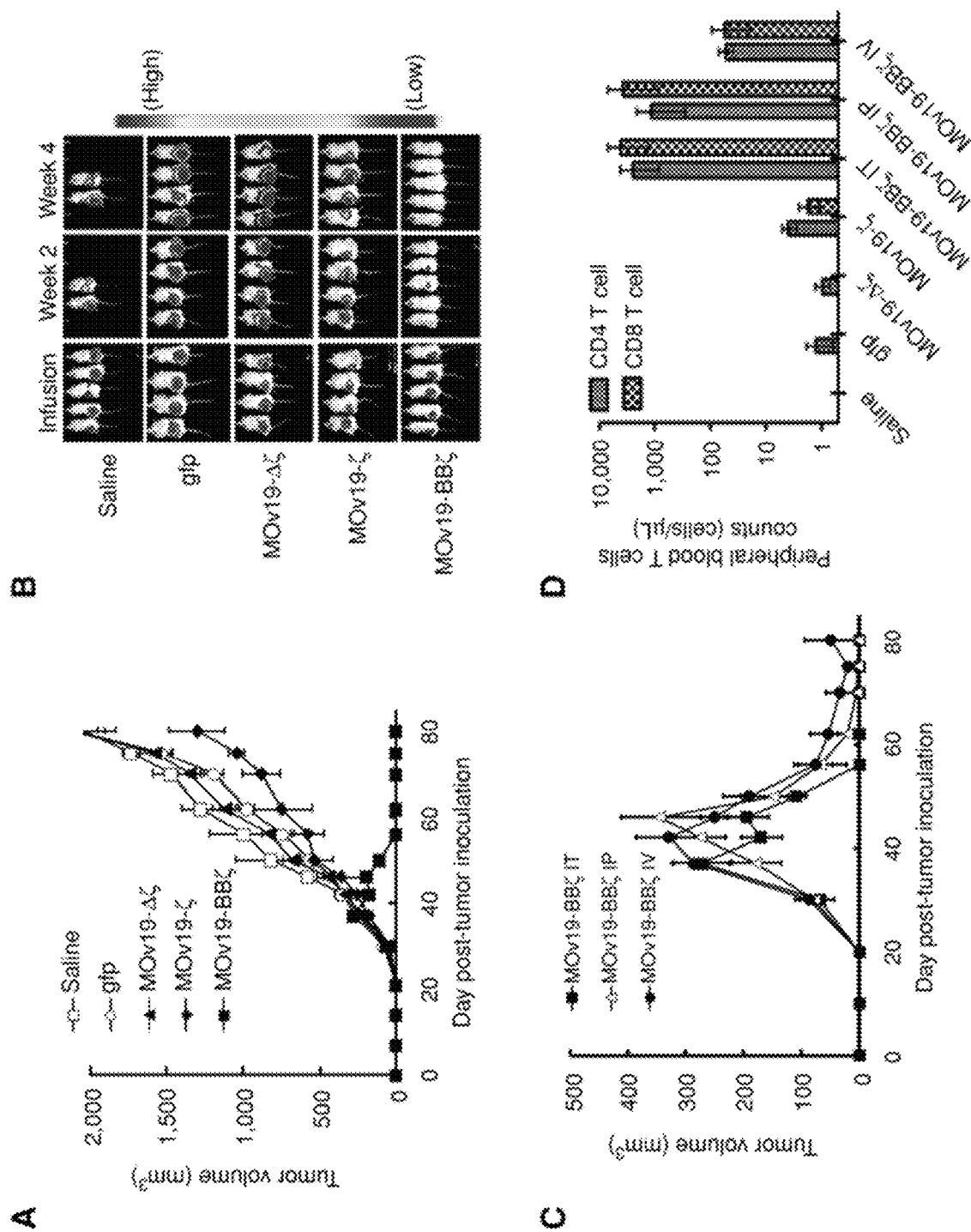
FIGS. 19A-19D are a series of graphs and images that show human MOv19-BBζ CAR T cells eradicate large pre-established tumors in vivo, and showing the effect of CD137 costimulatory signaling domains and route of administration. NSG mice bearing established s.c. tumor were treated with intratumoral injections of 8×10$^6$ CAR$^+$ T cells on days 0 and 5 and imaged every 2 weeks.

CAR functional activity in vitro cannot adequately predict the antitumor potential of transduced human T cells in vivo. The antitumor efficacy of FRα CAR constructs were evaluated in a xenograft model of large, established cancer. Immunodeficient NOD/SCID/IL-2Rγc$^{null}$ (NSG) mice were inoculated s.c. with firefly luciferase (fLuc)-transfected FRα⁺ SKOV3 human ovarian cancer cells on the flank and received intratumoral (i.t.) injections of CAR⁺ T cells on days 40 and 45 post-tumor inoculation (p.i.), when tumors were 250 mm³ or more in size. Tumors in mice receiving saline, MOv19-Δζ CAR T cells, or gfp T cells progressed beyond the time of T cell transfer as measured by caliper-based sizing and bioluminescence imaging (BLI; FIG. 19A and FIG. 19B). Tumor growth was modestly delayed in mice receiving MOv19-ζ T cells (P=0.027), compared with all 3 control groups at the latest evaluated time point (38 days after first T-cell dose). In contrast, mice receiving i.t. injection of MOv19-BBζ T cells experienced rapid tumor regression, which was significantly better than MOv19-ζ T cells (P<0.001), indicating that incorporation of CD137 signals enhances overall antitumor activity in vivo. Tumor-bearing mice treated with MOv19-BBζ-transduced T cells delivered via i.v., i.p. injection, or i.t. routes experienced tumor regression (FIG. 19C). Following i.v. or i.p. infusion of MOv19-BBζ T cells, antitumor activity was again observed, though delayed in regression by approximately 7 days relative to i.t. delivery, indicating that although local injection is optimal, systemically infused CAR T cells can marginalize upon adoptive transfer to mediate potent antitumor effects in vivo.

Figure 27:
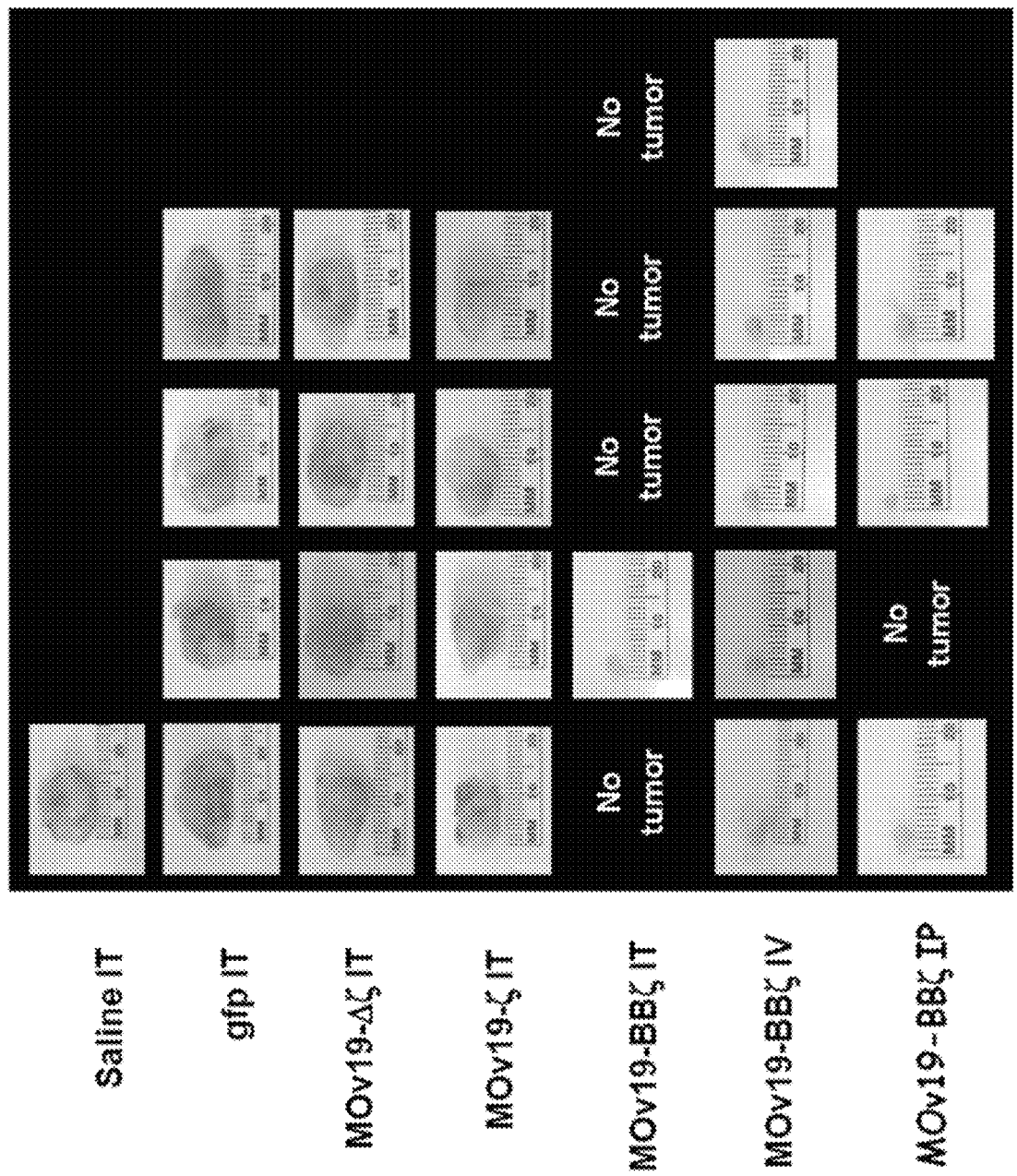
FIG. 27 is a series of images depicting macroscopic evaluation of resected tumor specimens following T cell therapy. Tumors were harvested from NSG mice injected intratumorally (i.t.) with saline or T cells bearing gfp, MOv19-Δζ, MOv19-ζ, MOv19-BBζ CARs; or injected intravenously (i.v.) or intraperitoneally (i.p.) with MOv19-BBζ T cells. "No tumor" represents mice in which tumors were not detected. Tumors were harvested from mice at the time of euthanasia, nearly 40 days after first T cell injection.

Persistence of Primary Human FRα CAR T Cells In Vivo is Increased by 4-1BB Signals Without wishing to be bound by any particular theory, it is believed that the persistence of transferred tumor-reactive T cells following adoptive T-cell therapy is highly correlated with tumor regression (Robbins et al., 2004, J Immunol 173:7125-30). In experiments described elsewhere herein, peripheral blood was collected from tumor-bearing mice 3 weeks after the last T-cell dose and quantified for persistent human CD4$^+$ and CD8$^+$ T cells (FIG. 19D). CD4$^+$ and CD8$^+$ T-cell counts were highest in mice receiving MOv19-BBζ CAR T cells, whether delivered by i.t., i.p., or i.v. routes of administration, compared with gfp, MOv19-Δζ, and MOv19-ζ treatment groups. Notably, human T-cell counts in mice receiving MOv19-BBζ CAR T cells by i.v. injection was significantly higher than those in the parallel MOv19-ζ CAR group (P<0.01), indicating a role for CD137 in T-cell survival in vivo. There was no significant difference in level of T-cell persistence among mice receiving MOv19-BBζ CAR T cells by i.v., i.t., or i.p. injection (P=0.2), despite a trend toward less cells in the i.v. injection group. Total T-cell counts in the MOv19-ζ treatment group was statistically similar to other control groups including mice receiving saline in the absence of human T-cell injection (FIGS. 26A-26D; P>0.05), suggesting that antigen specificity alone is not sufficient for T-cell maintenance in vivo. This was primarily attributed to poor CD4$^+$ T-cell persistence because circulating MOv19-ζ CAR CD8$^+$ T cells persisted at greater numbers than MOv19-Δζ CAR (P=0.026) or gfp (P=0.013) cells. Four weeks after last MOv19-BBζ CAR T-cell dose, the absolute number of human T cells persisting in the blood was inversely correlated with tumor burden of each group (FIGS. 26A-26D; r=−0.78). Tumor BLI results were consistent with the size of resected residual tumors (FIG. 27). While not wishing to be bound by any theory, enhanced persistence of MOv19-BBζ CAR T cells, compared with MOv19-ζ, seemed to be attributed in part to an increased upregulation of anti-apoptotic Bcl-X$_L$, protein expression after antigen stimulation (FIGS. 26A-26D). Thus, tumor regression was associated with the stable persistence of engineered human T cells in vivo and supported by provision of CD137 costimulation.

Tumor Regression and T-Cell Persistence are Antigen-Driven In Vivo

Figures 20A, 20B, 20C, 20D:
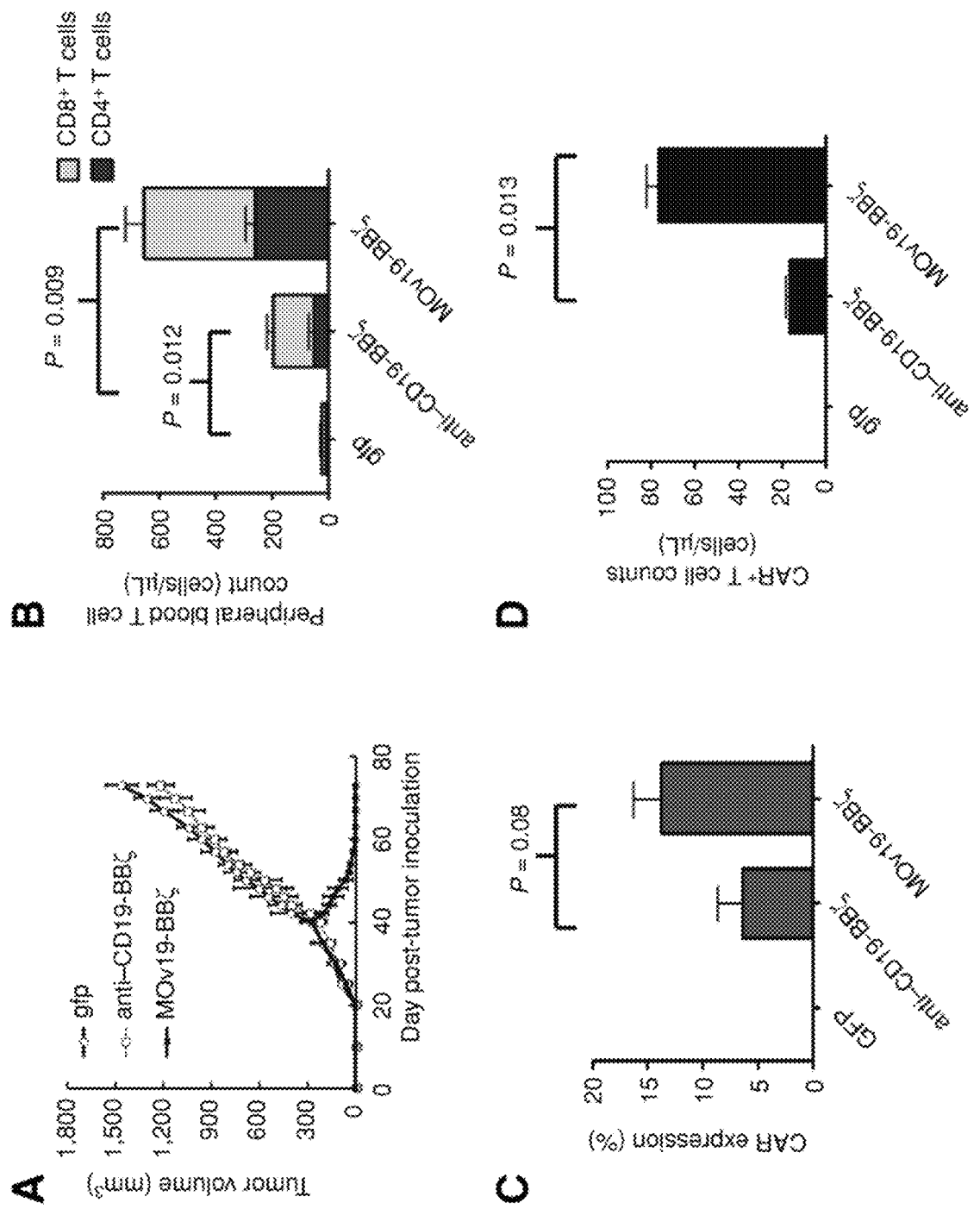
FIGS. 20A-20D are a series of graphs showing that tumor eradication by CAR T cells is antigen-specific. NSG mice with s.c. SKOV3 fLuc$^+$ tumor were treated with 8×10$^6$ T cells (40% transduction efficiency) expressing MOv19-BBζ, anti-CD19-BBζ, or gfp via i.t. infusion on days 0 and 5.
Figure 21:
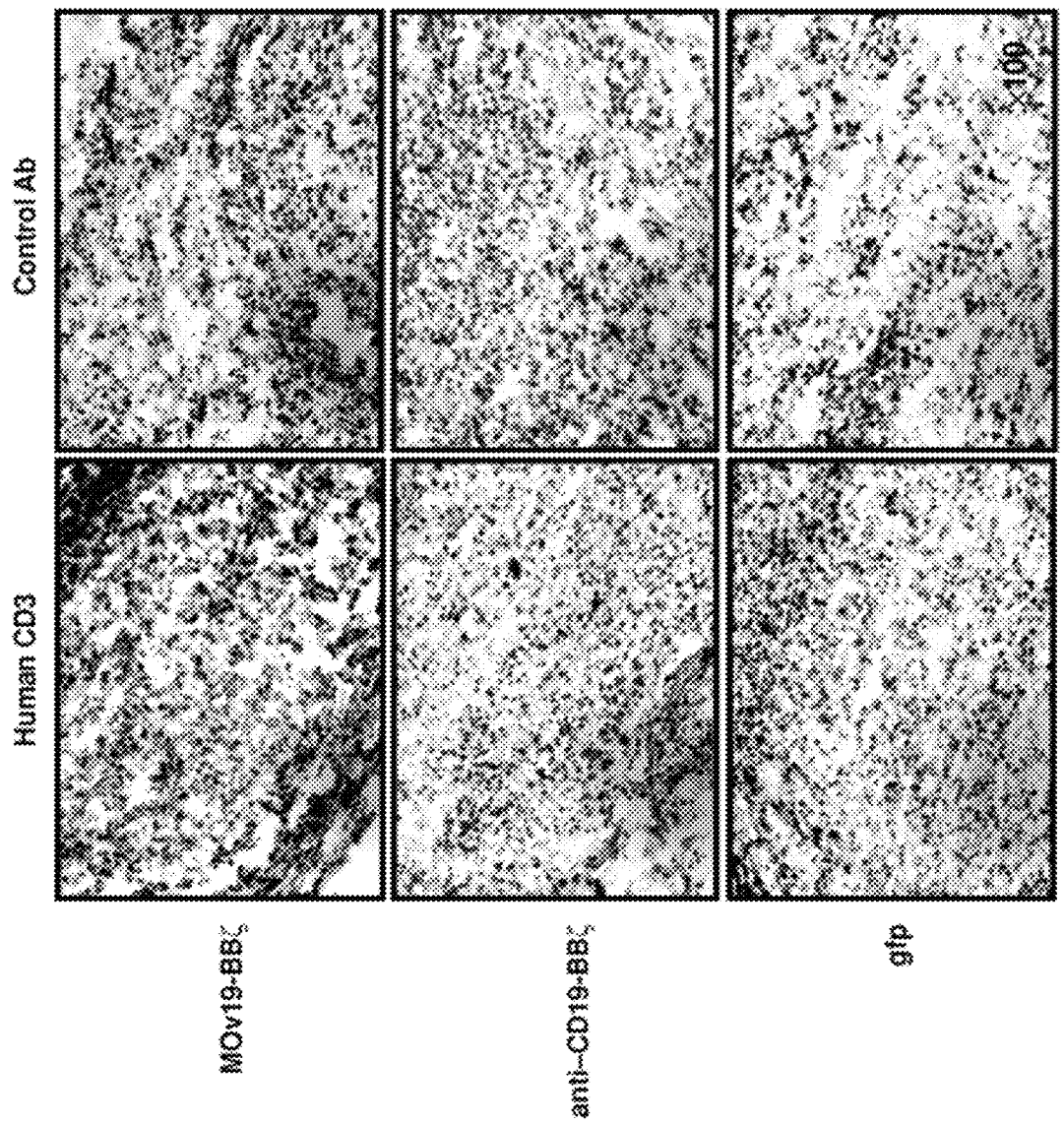
FIG. 21 is a series of images demonstrating that CAR T-cell localization to tumor in vivo is antigen-specific. NSG mice with s.c. SKOV3 fLuc$^+$ tumors were treated with i.v. injections of 8×10$^6$ T cells expressing MOv19-BBζ (top), anti-CD19-BBζ (middle), or gfp (bottom) on days 0 and 5. SKOV3 tumors grown for approximately 40 additional days were collected from euthanized mice and stained for human CD3 expression (brown). Representative sections are shown at ×100 magnifications.

To determine whether MOv19-BBζ CAR antitumor activity is antigen-specific, a comparative study was conducted with an anti-CD19-specific CAR also containing the CD137 signaling domain (Milone et al., 2009, Mol Ther 17:1453-64). NSG mice with established s.c. SKOV3 fLuc$^+$ tumor receiving 2 i.t. T-cell injections experienced rapid tumor regression, whereas tumor grew progressively in mice treated with T cells expressing gfp or CD19-BBζ CAR (FIG. 20A), excluding alloreactivity as a mechanism of tumor regression. Mice receiving MOv19-BBζ T cells had significantly higher human CD4$^+$ and CD8$^+$ T cell counts than mice in anti-CD19 CAR or gfp groups (FIG. 20B; P=0.009), indicating that tumor antigen recognition drives the survival of the adoptively transferred T cells in vivo. Interestingly, T-cell persistence was reproducibly higher in mice receiving anti-CD19-BBζ CAR T cells than gfp T cells (P=0.012), suggesting that persistence of CAR T cells can be promoted in part through a CD137-driven process that does not require scFv engagement with antigen. Nevertheless, there was no statistical difference in tumor control between anti-CD19-BBζ CAR and gfp groups (P=0.065) even at the latest time point studied (day 73), showing that persistence in the absence of antigen specificity is insufficient to mediate tumor response. In this line, CAR expressing T-cell frequency in the blood of tumor-bearing mice administered MOv19-BBζ T cells was higher than that observed in mice receiving CD19-BBζ CAR T cells, though not at statistical significance (FIG. 20C; P=0.08). However, coupled with increased T-cell counts, the total number of circulating CAR$^+$ T cells persisting 1 month after infusion were significantly higher in mice receiving MOv19-Bιg T cells (76±13 cells/μL; P=0.013); mice in CD19-BBζ CAR and gfp groups had little to no detectable persistence of CAR$^+$ T cells with counts of 12±4 cells/μL and 0±0 cells/μl, respectively (FIG. 20D). Consistent with the increased persistence of MOv19-BBζ T cells in the blood of treated animals, immunohistochemical analysis revealed robust accumulation of human CD3$^+$ T cells in regressing SKOV3 lesions 6 weeks after i.v. T-cell administration (FIG. 21). Few CD3$^+$ T cells were detected in tumors resected at the same time from mice that received anti-CD19-BBζ CAR or gfp-transduced T cells.

Tumor Regression in the Metastatic Disease Setting

Figures 22A, 22B, 22C, 22D:
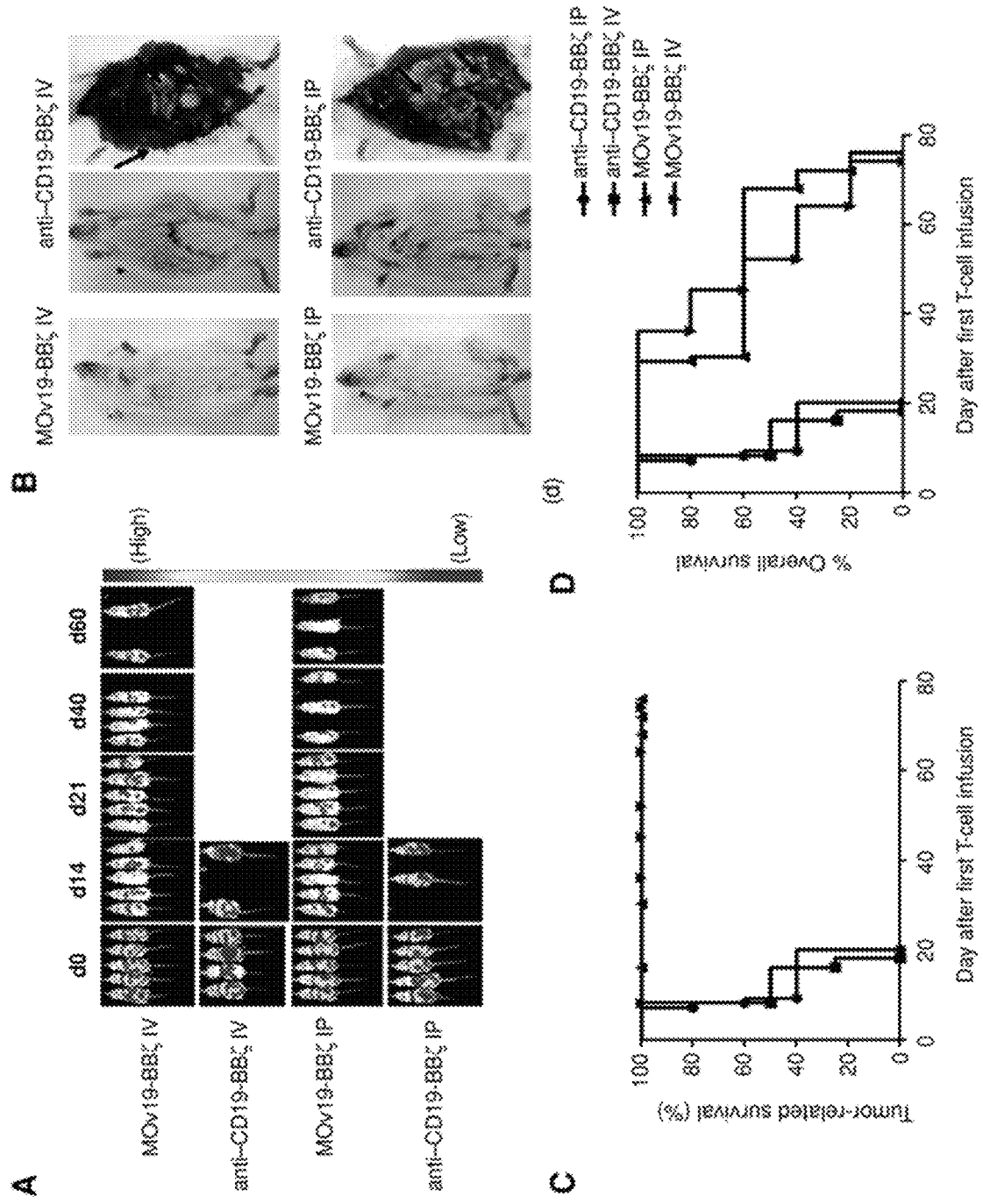
FIGS. 22A-22D are a series of images and a plots showing that Mov19-BBζ T cells inhibit tumor growth and ascites formation in SKOV3 murine model of peritoneal carcinomatosis.

Advanced ovarian cancer is a disease usually confined to the peritoneal cavity with occasional metastatic spread to the pleural compartment. A xenogeneic model of advanced i.p. metastatic cancer was established to evaluate the functional activity of FRα-specific T cells against tumor localized to a more physiologically relevant compartment. NSG mice that were inoculated i.p. with SKOV3 fLuc$^+$ cells efficiently developed peritoneal carcinomatosis which was readily evident 30 days p.i., when MOv19-BBζ or control anti-CD19-BBζ CAR T-cell therapy was administered (FIG. 22A). Within 3 weeks of T-cell transfer, all mice that received control anti-CD19-BBζ CAR T cells developed distended abdomens, marked bloody ascites of approximately 5 to 8 mL volume and multiple nodular peritoneal tumors, and had to be euthanized due to tumor-associated, abdominal distention (FIG. 22B and FIG. 22C). By comparison, mice treated with MOv19-BBζ CAR T cells did not develop distended abdomens or ascites, and exhibited a profound enhancement in tumor-related survival (P=0.0002) with no cases of tumor-related mortality in the MOv19-Bιg CAR group (FIG. 22C). At the time of euthanasia of mice treated with MOv19-BBζ, tumor burden was minimal to none, but mice required euthanizing due to signs of distress compatible with GVHD that develops in NSG mice following xenogeneic transfer of activated human lymphocytes (King et al., 2009, Clin Exp Immunol 157:104-18). Still, median survival times of 52 days after last T-cell infusion by i.v. injection and 68 days by the i.p. route were observed in mice treated with MOv19-BBζ CAR, compared with 9 and 12 days in the anti-CD19-BBζ CAR T-cell groups, respectively (MOv19-BBζ i.p. vs. anti-CD19-BBζ i.p., P=0.0023; MOv19-BBζ i.v. vs. anti-CD19-BBζ i.v., P=0.0025; FIG. 22D). Two months after treatment with MOv19-BBζ CAR cells via i.p. or i.v. routes, 60% (3 of 5) and 40% (2 of 5) of tumor-inoculated mice remained alive, respectively.

Figures 23A, 23B:
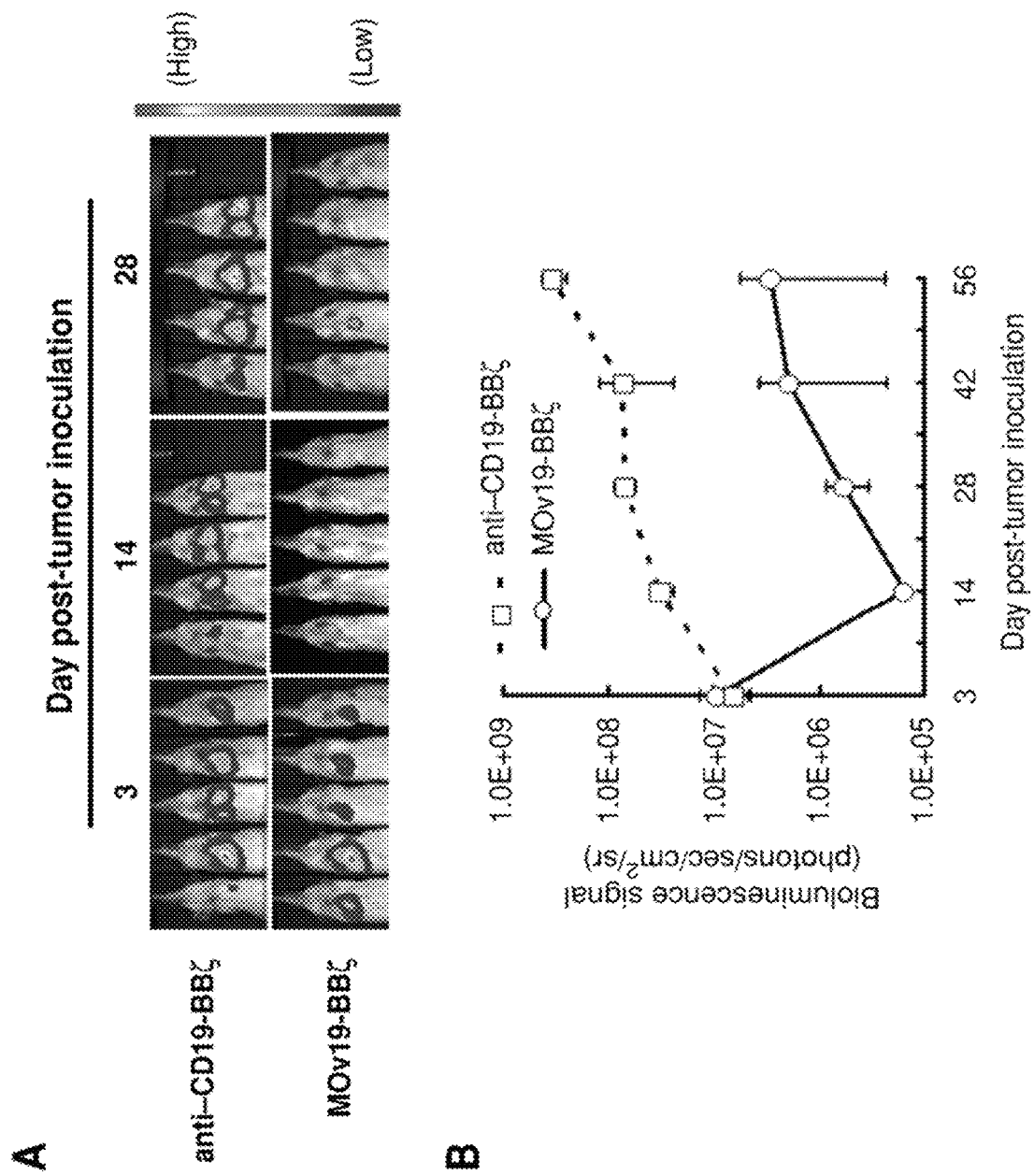
FIG. 23A-23B are a set of images and a plot showing that adoptive transfer of FRα-specific T cells induces regression of ovarian cancer lung metastasis. NSG mice with 3 day established SKOV3 fLuc$^+$ tumor in the lungs received tail-vein injections of 6×10$^6$ T cells expressing either MOv19-BBζ or anti-CD19-BBζ on day 3 and day 8.

Occasionally, ovarian cancer patients develop lung metastases and pleural ascites formation requiring thoracentesis or other supportive management procedures during disease progression (Sood et al., 1999, Clin Cancer Res 5:2485-90). A model of metastatic ovarian cancer of lung was generated by inoculation of NSG mice with SKOV3 fLuc$^+$ cells via tail-vein injection resulting in progressive lung metastases in 100% of mice 3 days p.i. (FIGS. 23A-23B). Two i.v. injections of MOv19-BBζ T cells resulted in rapid regression of lung metastasis in all treated animals 14 days p.i. and 80% (4 of 5) of mice had no evidence of recurrence after 1 month. By contrast, disease progression occurred in all mice receiving anti-CD19-BBζ T cells.

Tumor Response and T-Cell Persistence is Evoked by Provision of CD137 Costimulatory Signals to Anti-FRα CAR T Cells CARs combine the high affinity and specificity of antigen-specific antibody, which binds cell surface determinants in a non-MHC-restricted manner, with the potent effector functions of T lymphocytes (Gross et al., 1989, Proc Natl Acad Sci USA 86:10024-8). Genetically retargeting of primary human lymphocytes with CARs recognizing tumor-associated antigens offers a robust and rapid avenue toward the generation of tumor-reactive T cells for therapy. To date, CAR-based therapy has shown promising but often limited clinical activity, despite the reproducible demonstration of strong effector activity in vitro (Park et al., 2007, Mol Ther 15:825-33; Pule et al., 2005, Mol Ther 12:933-41; Kochenderfer et al., 2010, Blood 116:4099-102; Till et al., 2008, Blood 112:2261-71; Kershaw et al., 2006, Clin Cancer Res 12: 6106-15). Effective adoptive T-cell therapy not only requires antitumor activity, but also in vivo expansion and persistence of the infused tumor-reactive T cells (Robbins et al., 2004, J Immunol 173:7125-30). The experiments described herein have addressed the central issue of limited CAR T-cell persistence and tumor activity in vivo (Kershaw et al., 2006, Clin Cancer Res 12: 6106-15) through the introduction of the CD137 (4-1BB) costimulatory signaling domain into a Mov19 scFv-based CAR.

CD137 is a TNF receptor family member that plays an important role in T-cell proliferation and survival, particularly for T cells within the memory T-cell pool (Shuford et al., 1997, J Exp Med 186:47-55; Takahashi et al., 1999, J Immunol 162:5037-40; Suhoski et al., 2007, Mol Ther 15:981-8). CD137 was selected on the basis of its demonstrated capacity to support of CD8 T-cell expansion (Suhoski et al., 2007, Mol Ther 15:981-8), and upregulate important antiapoptotic protein Bcl-$X_L$ expression (Lee et al., 2002, Eur J Immunogenet 29:449-52), and results showing that adoptive transfer of tumor-specific T cells costimulated ex vivo with 4-1BBL supports persistence and antitumor activity in vivo (Yi et al., 2007, Cancer Res 67:10027-37). Like the "first-generation" Mov19-ζ CAR expressing CD3 signaling alone, T cells engineered to express a "second-generation" Mov19-BBζ CAR containing CD3 signaling and a CD137 signaling domain in tandem preferentially secrete high levels of Th1 cytokines including IFN-γ, TNF-α, and IL-2 upon tumor encounter and exert strong antitumor activity in vitro. Here, IFN-γ cytokine production levels were generally associated with the level of FRα expressed by tumor cell targets, and cytolysis of tumor cells by Mov19-ζ CAR and Mov19-BBζ CAR T cells was efficient even at a 3:1 effector to target cell (E/T) ratio in vitro. In all in vitro antitumor assays, engineered T cells expressing Mov19-BBζ CAR outperformed Mov19-ζ CAR T cells, albeit not always to the level of statistical significance. Interestingly, the single exception was in the level of Th2 cytokine secretion induced by tumor stimulation, where FRα engagement by Mov19-ζ CAR T cells induced greater IL-4 and IL-10 production, suggesting that combined CD3 and CD137 signaling enforces a Th1 skewed response.

The dichotomy between first- and second-generation CAR vectors was most evident in in vivo studies where CD137 bearing Mov19-BBζ CAR T cells facilitated superior regression of large vascularized tumors in an established human ovarian cancer xenograft model, whereas tumor progression was almost unabated with Mov19-ζ CAR T cells. Transfer of 16×10$^6$ total Mov19-BBζ CAR T cells eliminated an estimated 2.5×10$^8$ tumor cells (assuming that a 250 mm$^3$ tumor mass contains approximately 2.5×10$^8$ cells); in effect, an approximately 1:15 E/T ratio. Consistent with previous clinical observations (Dudley et al., 2002, Science 298:850-4; Robbins et al., 2008, J Immunol 180: 6116-31), tumor response was associated with enhanced T-cell persistence and tumor localization of Mov19-BBζ CAR T cells in vivo, which, without being held to any particular theory, seemed to be attributed in part to upregulated expression of Bcl-$X_L$ following stimulation with tumor. Tumor regression was antigen-specific, as transfer of anti-CD19-BBζ T cells had no impact on tumor progression. Tumor regression and T-cell persistence were attainable via systemic or local T-cell delivery, showing the capacity of transferred T cells to circulate, home to tumor and perform antitumor functions. Without being held to any particular theory, although i.v. injections are favorable in clinical application due to the ease of administration and effective in the model, data presented herein suggests that local administration of T cells may provide optimal therapeutic effect, which may be in part due to increased T-cell trafficking to tumor and provision of favorable E/T ratios. However, such delivery may not be applicable for tumors with multiple gross metastatic sites or micrometastases.

Although Mov19-BBζ and anti-CD19-BBζ T cells could be detected in the peripheral blood 3 weeks after T-cell infusion, the accumulation of Mov19-BBζ, but not anti-CD19-BBζ T cells, in FRα$^+$ tumor lesions suggests that antigen-selective retention of CAR bearing T cells in tumor occurs and may be requisite in part for tumor regression (Mukai et al., 1999, Cancer Res 59:5245-9). In a previous study, transferred TCR transgenic T cells migrated indiscriminately early after adoptive transfer but experienced antigen-dependent activation exclusively in antigen-positive tumor resulting in tumor destruction (Palmer et al., 2004, J Immunol 173:7209-16). Transfer of chemokine receptor expressing CAR T cells can enforce preferential migration to tumor sites to boost antitumor activity in vivo (Craddock et al., 2010, J Immunother 33:780-8). Results presented herein support the hypothesis that T-cell persistence, localization, and tumor activity in vivo are largely antigen-dependent, likely linked, processes. Notably, the use of anti-CD19-BBζ T cells as specificity control in the assays, however, shows that provision of CD137 signaling by CAR permitted improved T-cell persistence but not antitumor activity in vivo through a mechanism that is independent of scFv engagement with antigen, suggestive of low-level constitutive activity by the CD137 module, consistent with previous data (Milone et al., 2009, Mol Ther 17:1453-64). Without being held to any particular theory, it remains possible that persistence of nonspecific CD137-costimulated human T cells was driven by low-level TCR recognition of xenoantigens in mice combined with constitutive CD137 signaling by CAR, as shown by the occurrence of graft-versus-host manifestations, which is an inherent limitation of the xenogeneic NSG mouse model used.

In an earlier clinical study, retargeted T cells were generated for therapy by loading pre-activated T cells with a bispecific mouse mAb OC/TR, directed to the CD3 molecule on T lymphocytes and to FRα on EOC cells (Canevari et al., 1988, Int J Cancer Suppl 2:18-21). Administration of FRα-redirected T cells to women with minimal residual ovarian cancer resulted in antitumor responses in 27% of patients with mild to moderate immunotherapy-related toxicities; however, therapy was limited by the inability to generate stable anti-FRα-specific T-cell memory and the induction of human anti-mouse antibodies against the bispecific mAb in approximately 90% of treated patients (Canevari et al., 1995, J Natl Cancer Inst 87:1463-9). In a phase I study of anti-FRα CAR therapy for cancer, Kershaw and colleagues (Kershaw et al., 2006, Clin Cancer Res 12: 6106-15) transferred T cells that were retargeted to FRα by a first-generation MOv18 scFv-based CAR to immunocompetent patients with advanced ovarian cancer. The parental MOv18 antibody has a similar affinity for FRα ($10^8$-$10^9$ $M^{-1}$) as MOv19 used in the present CAR construct (Miotti et al., 1987, Int J Cancer 39:297-303; Figini et al., 1998, Cancer Res 58:991-6) though the relative affinities of their scFv products in CARs is not known. MOv18 and MOv19 also bind non-cross-reactive epitopes (Miotti et al., 1987, Int J Cancer 39:297-303), which may influence their relative ability to access surface antigen. Therapy using MOv18-ζ CAR was safe and feasible; however, no patient experienced a tumor response which was attributed to a lack of transferred T-cells persistence after infusion, poor tumor localization, and the development of a serum inhibitory factor that reduced CAR T-cell activity in in vivo study (Kershaw et al., 2006, Clin Cancer Res 12: 6106-15). Studies presented herein address these issues. Similar to the study of Kershaw and colleagues (Kershaw et al., 2006, Clin Cancer Res 12: 6106-15), first-generation MOv19-ζ CAR, which redirected T-cell cytotoxicity in vitro, only delayed tumor progression in vivo and CARs did not persist long-term in vivo. It is shown herein that tumor response and T-cell persistence can be evoked by provision of CD137 costimulatory signals to anti-FRα CAR T cells, which is facilitated principally by engagement of their CAR with tumor antigen. Moreover, transfer of MOv19-BBζ T cells leads to increased accumulation of human T cells in regressing ovarian cancer lesions. Although the mouse anti-human MOv19 scFv used in the construction of the MOv19-BBζ CAR is likely to elicit anti-mouse humoral responses in immunocompetent recipients, as seen in past CAR studies and trials using MOv18 scFv (Kershaw et al., 2006, Clin Cancer Res 12: 6106-15; Canevari et al., 1995, J Natl Cancer Inst 87:1463-9; Lamers et al., 2011, Blood 117:72-82), nonmyeloablative immunosuppressive preconditioning can disable host endogenous immunity to promote the in vivo persistence of T cells expressing CARs and TCRs of mouse origin, facilitating tumor regression (Kochenderfer et al., 2010, Blood 116: 4099-102; Berger et al., 2001, J Virol 75:799-808; Johnson et al., 2009, Blood 114:535-46). The use of immunodeficient NSG mice models T-cell transfer in the setting of host lymphodepletion, albeit in the absence of human derivatives and endogenous immune reconstitution. Based on the results presented herein, the use of fully human anti-FRα scFv candidates for the next generation of CAR-redirected therapy is worthy of investigation (Figini et al., 1998, Cancer Res 58:991-6; Figini et al., 2009, Cancer Immunol Immunother 58:531-46). Results presented herein support the notion that incorporation of the CD137 signaling domain in FRα-specific CARs overcomes the limitations of past CAR approaches by improving the persistence of transferred T cells in vivo, thereby increasing their retention in tumor and bolstering antitumor potency. Careful considerations must be made when targeting of self/tumor antigens with CARs or exogenous TCRs, which hold the potential for mediating serious adverse events (Johnson et al., 2009, Blood 114:535-46; Morgan et al., 2010, Mol Ther 18:843-51); however, FRα, which is present on normal tissues, is localized primarily to the apical surfaces of polarized epithelia, where it may be inaccessible to parenterally administered folate conjugates and redirected T cells (Low et al., 2004, Adv Drug Deliv Rev 56:1055-8).

Figure 28:
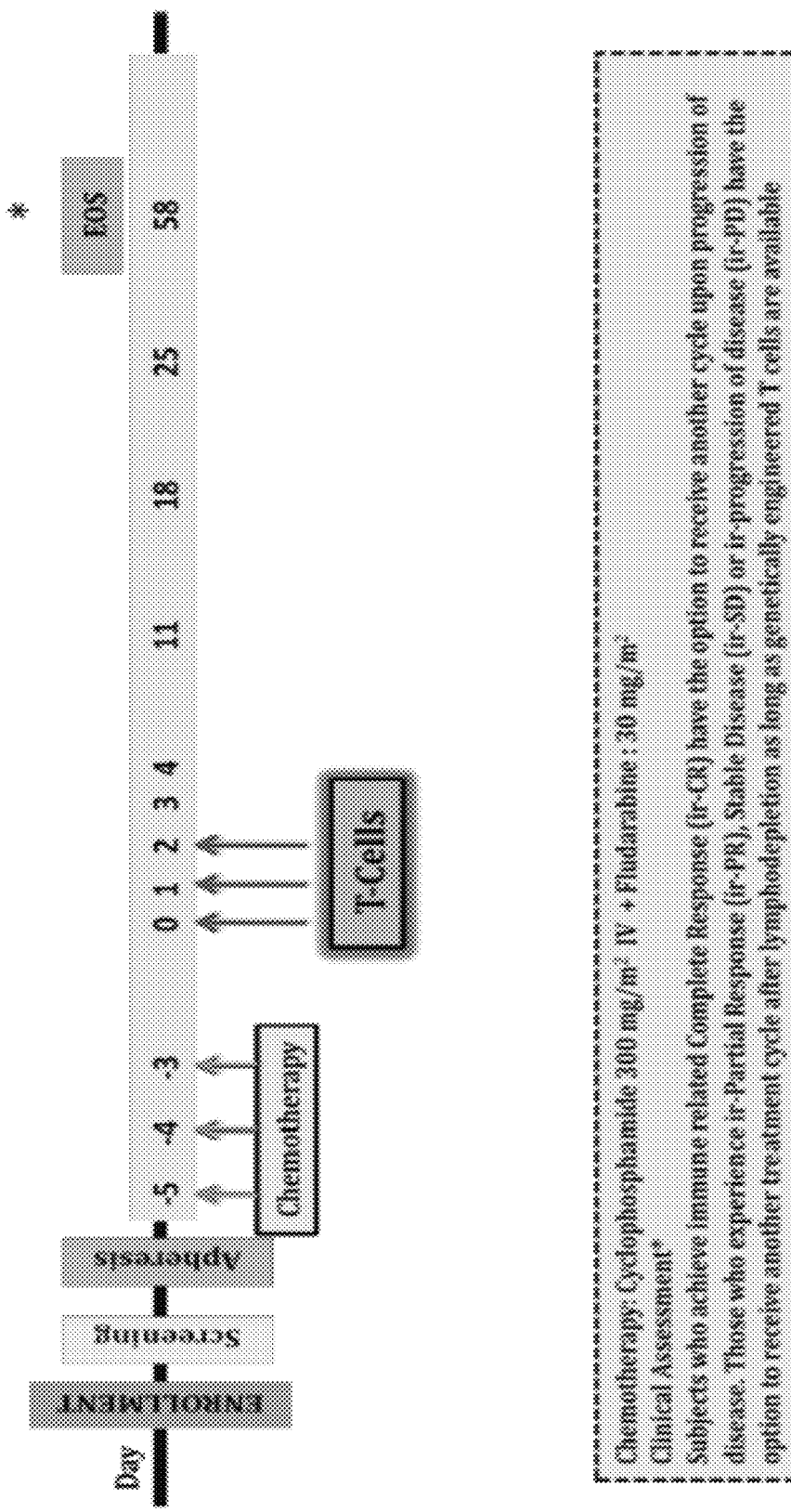
FIG. 28 is an image depicting the study protocol schema for the clinical trial detailed elsewhere herein.

Example 20: A Pilot Phase I Dose Escalation Study to Establish the Safety and Proof of Concept of Autologous Folate Receptor (α-FR)-Alpha Redirected T Cells Administration Intravenously in Patients with Recurrent Ovarian Cancer The major question in the development of CAR T cells for cancer therapy is identifying vector designs that enhance the persistence of the cells post infusion, and to optimize trafficking of CAR T cells to tumor sites. This study design tests the hypothesis that the changes in vector design improves the survival of CAR T cells in comparison to a previous study of ovarian cancer (Hwu et al., 2006, Clinical Cancer Research, 12(20): 6106-6115). Described herein is a phase I study to determine the safety, tolerability and feasibility of administering (CAR) T cells transduced with the anti-α-FR Chimeric Antigen Receptor (CAR) in subjects with ovarian cancer receiving anti-α-FR CAR T cells. The protocol schema is shown in FIG. 28. At entry subjects are screened and their eligibility is determined. Those who meet all eligibility criteria undergo apheresis within 4-6 weeks of screening to obtain peripheral blood mononuclear cells (PBMCs) for CAR T cell manufacturing. The T cells are purified from the PBMC, transduced with anti-α-FR scFv expanded in vitro and then frozen for future administration.

Investigational Agent and Dose

The study drug is autologous T cells that have been engineered to express a Chimeric Antigen Receptors (CAR) comprised of an extracellular single chain antibody (scFv) with specificity for α-FR and an intracellular TCRz chain and 4-1BB signaling domain. The CAR constructs were developed, and the clinical grade pELNS lentiviral vector carrying the MOv19-BBζ CAR has been already manufactured. The CAR T cells are cryopreserved in infusible cryomedia, and are administered in either 1 or 2 bags. Each bag contains an aliquot (volume dependent upon dose) of cryomedia containing the following infusible grade reagents (% v/v): 31.25 plasmalyte-A, 31.25 dextrose (5%), 0.45 NaCl, up to 7.50 DMSO, 1.00 dextran 40, 5.00 human serum albumin with the appropriate number of autologous T cells per bag.

Three T cell dose levels are tested, starting at the expected "Minimal Anticipated Biological Effect Level" (MABEL) dose of ~$3 \times 10^7$ CAR+ T cells/$m^2$ to reach an expected "No Observable Adverse Effect Level" (NOAEL) dose of ~$3 \times 10^8$ CAR+ T cells/$m^2$. For additional safety, a "split dose" approach to dosing is followed over 3 days, administering CAR-transduced T cells by intravenous infusion using 10% of the total intended on day 0, 30% on day 1 and 60% on day 2.

Patients receive a single dose of CAR T cells intravenously using a "split dose" regimen on day 0, 1 and 2 by rapid i.v. infusion. The infusion is scheduled to occur 2 days following chemotherapy.

Cohort 1 $3 \times 10^7$ CAR T cells/$m^2$ (with a minimally accepted dose of $2.5 \times 10^7$ and a maximally accepted dose of $3.5 \times 10^7$)

Cohort 2 $1 \times 10^8$ CAR T cells/$m^2$ (with a minimally accepted dose of $8 \times 10^7$ and a maximally accepted dose of $1.2 \times 10^8$)

Cohort 3 $3 \times 10^8$ CAR T cells/$m^2$ (with a minimally accepted dose of $2.6 \times 10^8$ and a maximally accepted dose of $3.4 \times 10^8$)

Preparation

The CAR T cells are prepared in a production facility and are not released from the production facility until release criteria for the infused cells (e.g., cell purity, sterility, average copy number of vectors/cell, etc.) are met. Upon release, the cells are taken to a clinic. Bags (50 to 100 ml capacity) containing CAR-transduced T cells are stored in blood bank conditions in a monitored −150° C. freezer at the University of Pennsylvania. Infusion bags are stored in the freezer until needed.

Cell Thawing

Transduced T cells are transported on dry ice from the production facility a stem cell unit at the clinic where the product is released. The transduced T cells are transported by the research nurse/coordinator to the patient's bedside in the clinic. The infusion takes place in an isolated room in the clinic. The cells are thawed at the bedside one bag at a time using a water bath maintained at 36° C. to 38° C. The bag is gently massaged until the cells have just thawed. It is made sure that there are no frozen clumps left in the container. If the CAR T cell product appears to have a damaged or leaking bag, or otherwise appears to be compromised, it is not infused, and is returned to the production facility.

Return or Destruction of Study Drug

CAR T cells may require return to the production facility for a variety of reasons, including but not limited to: 1) Mislabeled product; 2) Condition of patient prohibits infusion/injection, and 3) Subject refuses infusion/injection; any unused product are returned to production facility for disposal Premedication Side effects following T cell infusions include transient fever, chills, fatigue and/or nausea. It is recommended that the subjects be pre-medicated with acetaminophen 650 mg by mouth and diphenhydramine hydrochloride 25-50 mg by mouth or IV, prior to the infusion of CAR T cells. These medications may be repeated every six hours as needed. A course of non-steroidal anti-inflammatory medication may be prescribed if the patient continues to have fever not relieved by acetaminophen. It is recommended that patients not receive systemic corticosteroids such as hydrocortisone, prednisone, prednisolone (Solu-Medrol) or dexamethasone (Decadron) at any time, except in the case of a life-threatening emergency, since this may have an adverse effect on T cells. If corticosteroids are required for an acute infusional reaction, an initial dose of hydrocortisone 100 mg is recommended.

Administration of Study Drug

Cells are infused within approximately 10-40 minutes after thaw. The transduced T cells are administered on 3 consecutive days by rapid intravenous infusion at a flow rate of approximately 10 mL to 20 ml per minute through an 18-gauge latex free Y-type blood set with a 3-way stopcock. Dosing takes place by gravity infusion. If the infusion rate by gravity is too slow, the transduced T cell drug product is drawn into a 50 mL syringe via the stopcock and manually infused at the required rate. The duration of the infusion is approximately 15 minutes. One or two bags of CAR T cells are delivered to the bedside on ice, and the cells are administered to the subject while cold. Each infusion bag has affixed to it a label containing the following: "FOR AUTOLOGOUS USE ONLY." In addition the label has at least two unique identifiers such as the subject's initials, birth date, and study number. Prior to the infusion, two individuals independently verify all this information in the presence of the subject and so confirm that the information is correctly matched to the participant.

Emergency medical equipment (i.e., emergency trolley) is available during the infusion in case the subject has an allergic response, or severe hypotensive crisis, or any other reaction to the infusion. Vital signs (temperature, respiration rate, pulse, and blood pressure) are taken before and after infusion, then every 15 minutes for at least two hour and until these signs are satisfactory and stable. The subject is asked not to leave until the physician considers it is safe for him or her to do so.

Within 15 minutes (±5 minutes) following completion of dosing with transduced T cells, a blood sample is obtained for a baseline determination of the number of transduced T cells.

Screening and Baseline Evaluation:

Patients sign the informed consent before testing begins. Screening procedures are done within 4-6 weeks of apheresis, and include:

A review of inclusion/exclusion criteria

Confirm an ECOG performance status <2

Tumor Burden Evaluation: performed as standard of care to include CT scan chest, abdomen and pelvis. Does not have to be repeated if done within 4 weeks prior to visit Physical examination (including vital signs, height and weight, medical and medication history)

Review of concomitant medications

Hematology: Complete blood count (CBC), differential, platelets, Prothrombin Time (PT) and Partial Thromboplastin Time (PTT)

Serum Chemistries: BUN, creatinine, electrolytes, and glucose; calcium, magnesium, phosphate, SGOT, SGPT, alkaline phosphatase, LDH, total bilirubin, uric acid, total protein and albumin Virology (screening): HIV-1, 2, HTLV-1/2, Hepatitis B (HbsAg, α-HBc), Hepatitis C (αHCV).

Serum CA-125

Urinalysis

EKG (up to 6 weeks old, can be done outside of institution)

VSV-G antibody response and human anti-murine antibody (HAMA).

CT/MRI (up to 6 weeks old, can be done outside of institution)

Research Blood draws

Apheresis

A ~10-15 liter apheresis procedure is carried out at the apheresis center. PBMC are obtained for CAR T cells during this procedure. From a single leukapheresis, the intention is to harvest at least $50 \times 10^9$ white blood cells to manufacture CAR T cells. Baseline blood leukocytes for FDA look-back requirements and for research are also obtained and cryopreserved. Without being held to any particular theory, the cell product is expected to be ready for release approximately 4 weeks later. A repeat apheresis may be offered during the course of the study if the target number of T cells was not reached.

Transient Lymphodepletion Regimen (Day −5 Though −3)

Subjects receive a single course of outpatient conditioning lymphodepletion chemotherapy with intravenous cyclophosphamide (300 mg/m²/d for 3 days) and intravenous fludarabine (30 mg/m²/d for 3 days) on Day −5 through Day −3. This is a well-tolerated outpatient regimen. Dose reduction to cyclophosphamide 250 mg/m²/d and fludarabine 25 mg/m²/d is allowed at the discretion of the treating physician.

The following comprises a course of therapy for Day −5 through Day −3:

Subjects are pre-medicated with acetaminophen (Tylenol) 650 mg and hydrated with 0.9% Sodium Chloride with 10 meq/1 KCL at 2.6 ml/kg/hr (hydration is at the discretion of the Investigator).

Subjects receive daily Cyclophosphamide 300 mg/m$^2$/d IV in 250 ml D5W over 1 hr for 3 days. Maximum dose not to exceed doses calculated on body weights greater than 140% of the maximum ideal body weight.

Subjects receive daily Fludarabine 30 mg/m$^2$/day IVPB daily over 15-30 minutes for 3 days. Maximum dose not to exceed doses calculated on body weights greater than 140% of the maximum ideal body weight (Metropolitan Life Insurance Company). The fludarabine is started approximately 1-2 hours after the cyclophosphamide.

Antibiotics, Anti-fungals and Anti-virals are given to subjects as prophylaxis: The typical phrophylactic doses are: Altrex 500 mg daily, Bactrium DS one tablet q M W F and Fluconazole 200 mg daily. The duration of medication is until Absolute Lymphocyte count (ALC) and Absolute Neutrophil Count (ANC) count returns to pre medication baseline.

Patients are encouraged oral intake of fluids of 2-3 liters/day on the day prior to, during and following chemotherapy. Hematopoietic growth factors are given as clinically indicated.

CAR T Cell Administration for First Treatment Cycle (Day 0, 1 & 2)

Subjects receive infusions in an isolated room. The cells are thawed at the patient's bedside as described elsewhere herein. The thawed cells are given at an infusion rate as quickly as tolerated so that the duration of each infusion is approximately 10-15 minutes. In order to facilitate mixing, the cells are administered simultaneously using a Y-adapter. A blood sample for determination of baseline CAR T cell level is obtained before infusion and 20 minutes post infusion. Subjects are infused and premedicated as described elsewhere herein. Subjects are observed for at least 2 hours post infusion, with vital signs (temperature, respiration rate, pulse and blood pressure) monitored every 15 minutes for at least two hours and until these signs are satisfactory and stable. Pulse oximetry determination of blood oxygenation is used as means of pulmonary assessment prior to and 15 minutes post T cell infusion and every 15 min thereafter until the completion of the observation period.

Subject Assessments

Subjects have the following done on Day 0, 1&2 before T cell infusion:
ECOG Performance Status
Physical Exam (including vital signs, weight, ConMed and Adverse event assessment).
Hematology: CBC, differential and platelets, Prothrombin Time (PT) and Partial Thromboplastin Time (PTT).
Serum Chemistries: BUN, creatinine, electrolytes, glucose, calcium, SGOT, SGPT, alkaline phosphatase, total bilirubin, total protein, albumin.
Urinalysis: random urine protein, random urine creatinine to measure urine protein:creatinine (UPC) ratio. 24-hour urine protein is determined in subjects with proteinuria greater than +1 in the absence of UTI.
Serum CA-125
Serum HAMA and VSV-G level
Research blood draws Subjects have the following done on Day 7, 14, 25 and 39 post T cell infusion:
ECOG Performance Status
Physical Exam (including vital signs, weight, ConMed and Adverse event assessment).
Hematology: CBC, differential and platelets, Prothrombin Time (PT) and Partial Thromboplastin Time (PTT).
Serum Chemistries: BUN, creatinine, electrolytes, glucose, calcium, SGOT, SGPT, alkaline phosphatase, total bilirubin, total protein, albumin.
Urinalysis: random urine protein, random urine creatinine to measure urine protein:creatinine (UPC) ratio. 24-hour urine protein is determined in subjects with proteinuria greater than +1 in the absence of UTI.
EKG
Serum HAMA and VSV-G level
Research blood draws
Subjects undergo a CT guided tumor biopsy around Day 39.

Pre and Post Infusion Laboratories to Assess Safety and Engraftment

Subjects are asked to undergo ~100 ml phlebotomy (2 red tops and 3 green tops) to evaluate the presence and safety of CAR T cells and for collection of immunological data on the following time points during the first treatment cycle: Day −5 (prior to lymphodepletion), Day 0 (prior to T cell infusion), 15 minutes and 2 hours after each T cell infusion, then daily till Day 7, then again on Day 9, 11, 14, 18, 25 then once every 2 weeks until EOS.

At EOS (Day 58), an additional of ~200 ml phlebotomy (5 green tops and 3 red tops) is collected. All subjects undergo ~6 ml phlebotomy on first and third day of cyclophosphamide chemotherapy prior to chemotherapy infusion; and prior to T cell infusion; twice weekly thereafter till ANC and ALC reach pretreatment baseline or 1500 and 1000 respectively Serum CA-125 levels are recorded at least monthly during the study, but are not be included in clinical decision-making.

End of Study Evaluations (EOS, Day ~58)

Specific monitoring tests and procedures are completed on Day ~58 as follows:
ECOG Performance Status
Physical Exam (including vital signs, weight, ConMed and Adverse event assessment).
Hematology: CBC, differential and platelets, Prothrombin Time (PT) and Partial Thromboplastin Time (PTT).
Serum Chemistries: BUN, creatinine, electrolytes, glucose, calcium, SGOT, SGPT, alkaline phosphatase, total bilirubin, total protein, albumin, LDH, magnesium, phosphate, uric acid.
Serum CA-125
Tumor Burden Evaluation: CT/MRI scan of chest, abdomen and pelvis
EKG
Subjects have ~200 ml phlebotomy for immunologic monitoring (5 green tops and 2 red tops). C
CT/MRI On Day 58 (End of Study (EOS)), subjects have completed the first treatment cycle and have undergone immune and clinical assessment (as measured by immune-related response criteria). Subjects who achieve immune related Complete Response (ir-CR) have the option to receive another cycle upon progression of disease. Those who experience ir-Partial Response (ir-PR), ir-Stable Disease (ir-SD) or ir-progression of disease (ir-PD) have the option to receive another treatment cycle after lymphodepletion. Subjects only receive more than one cycle if the all safety parameters are met and it is safe to move to the next cycle. Subject has to also have genetically engineered T cells available.

Primary Endpoints

Primary endpoints of the study include:

Safety: Monitor the occurrence of study related adverse events (defined as ≥Grade 3 signs/symptoms, laboratory toxicities, and clinical events, with some exceptions noted previously) that are "possibly", "likely", or "definitely" related to study treatment any time from the first day of study treatment until EOS.

Feasibility: Feasibility is defined as the number of manufactured products that do not meet release criteria for vector transduction efficiency. T cell purity, viability, and sterility is determined (defined as "manufacturing failures").

Secondary Endpoints

The major secondary endpoints of the study include:

Persistence and Engraftment of CAR T cells: Engraftment of CAR T cells is evaluated post dosing by DNA PCR for vector copy number in PBMC. The number of anti-α-folate receptor CAR T cells in the blood is measured by RT-PCR performed ~15 minutes, 2 hours after each T cell infusion then daily till Day 7, then again on Day 9, 11, 14, 18, 25 then once every two weeks till end of study. The Optimal Biologic Dose (OBD) is defined by comparing the dose levels for safety profile and engraftment of CAR T cells in circulation and tumor biopsies; the OBD has the highest engraftment at day 28 with an acceptable toxicity profile.

Clinical Efficacy: Immune related response, the distribution of progression-free survival, overall survival and time to progression for patients treated with CAR T cells following lymphodepletion with cyclophosphamide/fludarabine is determined.

The effect of CAR T cells on tumor immunity and α-folate receptor expression is determined using research laboratory assays.

Persistence, Engraftment, Phenotype and Function of CAR+ T cells: FRα CAR+ T cells are readily identified by flow cytometry using PE conjugated goat anti-mouse IgG F(ab')2 (Jackson ImmunoResearch). CAR+ T cells are quantified in peripheral blood longitudinally (~15 minutes, 24 hrs, 48 hrs, 72 hrs, Day, 7, 14, 21, and 28 days as well as at 6, 8, 12, 16 weeks and every 6 months after dosing. In addition, CAR+ T cells are detected by DNA quantitative (q)PCR for vector copy number in PBMC, an acquisitively sensitive method to test for persistence of CAR+ T cells. Phenotypic analysis of CAR+ T cells includes detailed interrogation for memory cell (CCR7, CD62L, CD45RA, CD27, CD28, Fas etc) vs. effector cell markers (CD45RO, CCR6, CD25, CD38, HLADR, GITR, PD1 etc). CAR+ T cells are also phenotyped for IL-7 receptor CD127 and IL-15 receptor alpha expression. Ex vivo stimulation with PHA-ionomycin or cognate antigen followed by interrogation of intracellular cytokines (INFγ, TNFα, IL-2, IL-17, IL-4, TGFβ, IL-10), granzymes, CD137 and CD107a provides a detailed and longitudinal characterization of in vivo polarization and function post transfer. The presence of CAR+ T cells is quantified in tumor biopsies by DNA qPCR and correlated with FRα protein expression at baseline and end of study.

CAR immunogenicity: The development of host immune responses to the CAR T cells by HAMA and VSV-G ELISA is assessed and correlated with engraftment of CAR+ T cells.

Effect of CAR+ T cells on tumor microenvironment: Detailed leukocyte subset infiltrate analysis are performed by immunohistochemistry, and comprehensive immune analysis of the tumor microenvironment is done by multiplex qPCR and/or Affymetrix arrays.

Dose optimization: The OBD is defined by comparing the dose levels for safety profile and engraftment of CAR+ T cells in circulation and tumor biopsies; the OBD has the highest engraftment at day 28 with an acceptable toxicity profile.

Number of modified T-cells in serum, HAMA levels, serum ELISPOT measures of host immunity to anti-α-folate receptor and immune function, as well as VSV-G antibody response are displayed graphically as a function of time. The mean levels of α-folate receptor expression between tumors with and without intratumoral anti-α-folate transduced cells are computed for those patients who receive tissue biopsy. 95% confidence intervals for proportions and means are computed.

Cytokine measurements are conducted using Luminex and evaluating a panel of cytokines/chemokines/immune factors with potential to be modulated by the treatment. The panel is composed of all or a subset of the following factors: IL-1β, IL-1RA, IL-2, IL-2R, IL-4, IL-5, IL-6, IL-7, IL-8, IL-10, IL-12p40/p70, IL-13, IL-15, IL-17, TNF-α, IFN-α, IFN-γ, GM-CSF. These measurements are conducted on serum samples collected on Day −5 (prior to lymphodepletion), Day 0 (prior to T cell infusion), 15 minutes and 2 hours after each T cell infusion, then daily till Day 7, then again on Day 9, 11, 14, 18, 25 then once every 2 weeks until EOS. This helps to determine IL-7's profile in the first three cohorts and help better determine rhIL-7's administration schedule in a future cohort.

Clinical Efficacy

Anti-tumor activity is reported as a secondary trial endpoint. The purpose of this trial is to determine early on in clinical development of CAR T cells the persistence and engraftment of these cells using the IV route of administration. Response and progression is evaluated in this study using the new immune-related response criteria.

Definition of Tumor Response Using irRC

The sum of the products of diameters at tumor assessment using the immune-related response criteria (irRC) for progressive disease incorporates the contribution of new measurable lesions. Each net Percentage Change in Tumor Burden per assessment using irRC criteria accounts for the size and growth kinetics of both old and new lesions as they appear (Wolchok et al., 2009, Clinical Cancer Research, 15(23): 7412-7420; Hoos et al., 2010, Journal of the National Cancer Institute, 102(18): 1388-1397; Hodi, 2010, New England Journal of Medicine, 363(13): 1290)

Definition of Index Lesions Response Using irRC irComplete Response (irCR): Complete disappearance of all index lesions.

irPartial Response (irPR): Decrease, relative to baseline, of 50% or greater in the sum of the products of the two largest perpendicular diameters of all index and all new measurable lesions (ie., Percentage Change in Tumor Burden). Note: the appearance of new measurable lesions is factored into the overall tumor burden, but does not automatically qualify as progressive disease until the SPD increases by ≥25% when compared to SPD at nadir.

irStable Disease (irSD): Does not meet criteria for irCR or irPR, in the absence of progressive disease.

irProgressive Disease (irPD): At least 25% increase Percentage Change in Tumor Burden (i.e., taking sum of the products of all index lesions and any new lesions) when compared to SPD at nadir.

Definition of Non-Index Lesions Response Using irRC irComplete Response (irCR): Complete disappearance of all non-index lesions.

irPartial Response (irPR) or irStable Disease (irSD): non-index lesion(s) are not considered in the definition of PR, these terms do not apply.

irProgressive Disease (irPD): Increases in number or size of non-index lesion(s) does not constitute progressive disease unless/until the Percentage Change in Tumor Burden increases by 25% (i.e., the SPD at nadir of the index lesions increases by the required amount).

Impact of New Lesions on irRC

New lesions in and by themselves do not qualify as progressive disease. However their contribution to total tumor burden is included in the SPD, which in turn feeds into the irRC criteria for tumor response. Therefore, new non-measurable lesions do not discontinue any subject from the study.

Definition of Overall Response Using irRC

Overall response using irRC is based on these criteria:

Immune-Related Complete Response (irCR): Complete disappearance of all tumor lesions (index and nonindex together with no new measurable/unmeasurable lesions) for at least 4 weeks from the date of documentation of complete response.

Immune-Related Partial Response (irPR): The sum of the products of the two largest perpendicular diameters of all index lesions is measured and captured as the SPD baseline. At each subsequent tumor assessment, the sum of the products of the two largest perpendicular diameters of all index lesions and of new measurable lesions are added together to provide the Immune Response Sum of Product Diameters (irSPD). A decrease, relative to baseline of the irSPD compared to the previous SPD baseline, of 50% or greater is considered an immune Partial Response (irPR).

Immune-Related Stable Disease (irSD): irSD is defined as the failure to meet criteria for immune complete response or immune partial response, in the absence of progressive disease.

Immune-Related Progressive Disease (irPD): It is recommended in difficult cases to confirm PD by serial imaging. Any of the following constitutes progressive disease:

At least 25% increase in the sum of the products of all index lesions over baseline SPD calculated for the index lesions.

At least a 25% increase in the sum of the products of all index lesions and new measurable lesions (irSPD) over the baseline SPD calculated for the index lesions.

Yearly Evaluations 1 to 15 Years Post Infusion

At the end of the study, patients have long-term follow up for up to 15 years in accordance with recent guidelines for long term follow-up (LTFU) set forth by the ASGT and the FDA. LTFU requires 6 months visits for the first 5 years post infusion, and then annual visits if the vector modified cells are no longer detected in the blood. Visits involve blood draws and a physical exam.

Data Collection and Follow-Up for Withdrawn Subjects

Follow-up data collection after cell therapy clinical trials for subjects who receive the study drug is up to 15 years in accordance with FDA guidelines. As long as patients have detectable cells transduced with the scFv chimeric receptor, they are followed for toxicity, immune reactions, and any long-term adverse events. Many patients who respond to cell therapy may also have prolonged DFS but are also at risk for late relapse. The intent is to follow all patients treated with CAR T cells indefinitely at least until the time alternative treatment is required for their disease, and/or they are no longer at risk for toxicity from the infused cells (i.e. loss of engraftment). Therefore, data collection is continued regarding 1) engraftment as long as patients are at risk (until evidence of loss of detectable transduced T cells); 2) DFS until there is disease progression; 3) survival until the time of death or 4) until the patient withdraws consent for clinical data collection.

Patients who are followed at other institutions or practices, because of preference or geographical concerns have follow-up via notes from their local physician and/or phone interviews with periodic study assessments. An example would be a patient referred from out of state but cared for at another center. Toxicity and other clinical assessments are obtained from the treating physician. Every effort is made to contact subjects who appear to be lost to follow-up in order to at least obtain survival data. In the event a subject fails to complete the follow-up requirements, documentation of all attempts to contact the subject includes at least 3 telephone contacts (on different days and at different times of the day), and a certified letter. Subjects are withdrawn from DFS assessments if 1) there is evidence for lack of response, relapse or progressive disease after 6 months of follow-up or 2) at any time they require new treatment for their disease (i.e. conventional chemotherapy). Subjects are withdrawn from survival assessments at the time of death.

Figures 29A, 29B:
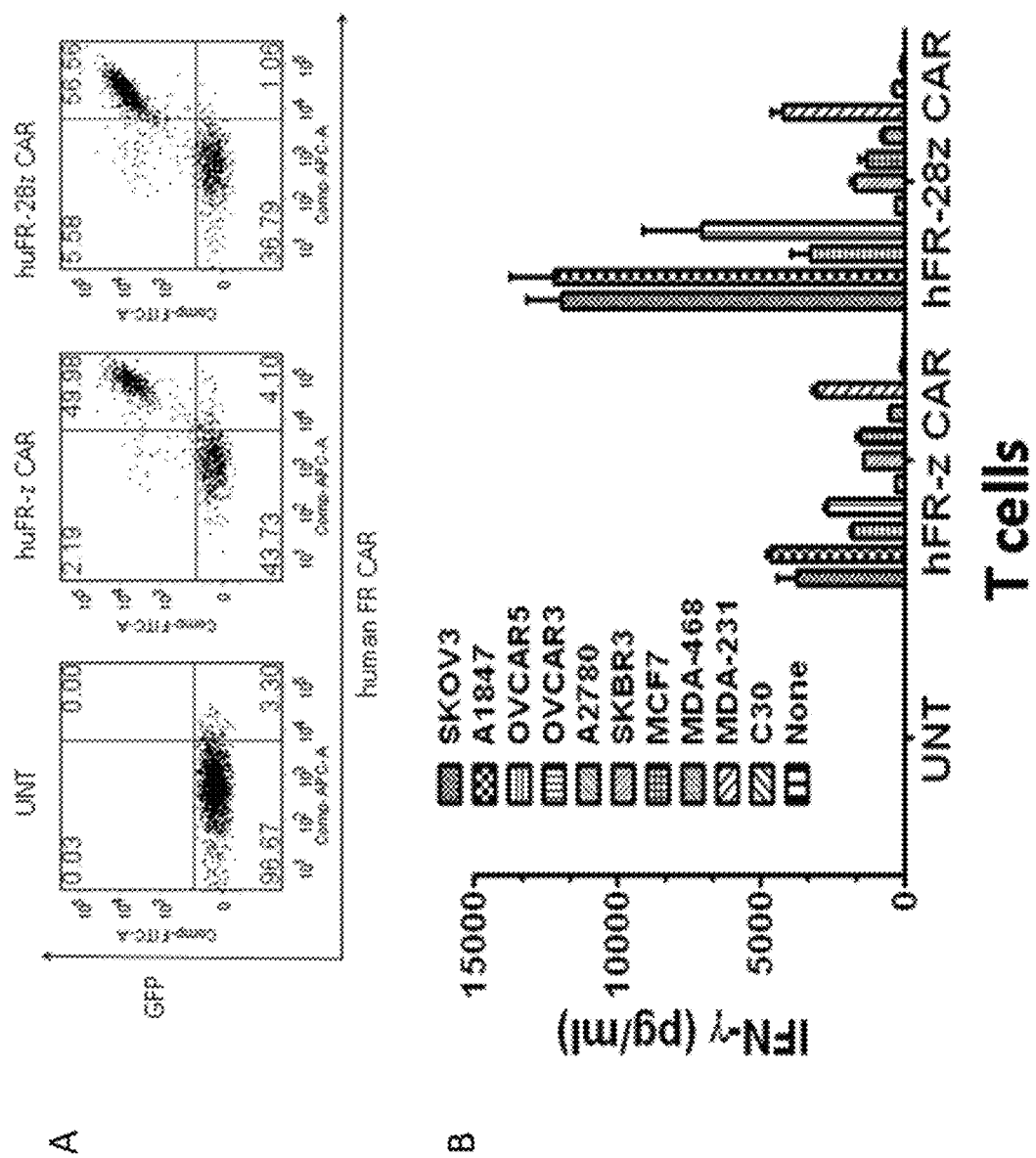
FIGS. 29A-29B are a set of plots showing that primary human T cells engineered to express a fully-human anti-FR CAR containing the humanized C4 scFv recognize and respond to FR expressing cancer cell lines in vitro. scFv was efficiently expressed on the surface of T cells transduced to express a first (-z) or second (-28z) CAR (FIG. 29A; using a bicistronic vector for gfp co-expression). CAR transduced, but not untransduced (UNT) T cells secreted IFN-g when co-cultured over night with ovarian or breast cancer cells expressing FR. Cell lines expressing little to no FR (A2780 and C30) were not recognized (FIG. 29B).

Example 21: Humanized Anti-FR CAR Recognize and Respond to FR Expressing Cancer Cell Lines A fully-human anti-FR CAR was constructed comprising the humanized C4 scFV. Primary human T cells were transduced to express the humanized anti-FR CAR, and the humanized anti-FR CAR was efficiently expressed on the surface of transduced T cells (FIGS. 29A-29B). Transduced and untransduced T cells were co-cultured overnight with ovarian or breast cancer cells. Humanized anti-FR CAR transduced T cells recognized FR expressing cell lines in vitro, as transduced, but not untransduced, T cells secreted IFN-γ when co-cultured with FR expressing cell lines. Cell lines that expressed little or no FR (A2780 and C30) were not recognized by transduced T cells (FIGS. 29A-29B).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A cell comprising a nucleic acid sequence encoding a chimeric antigen receptor (CAR), wherein the nucleic acid sequence comprises a sequence encoding an α-folate receptor (FRα) antibody comprising the amino acid sequence of SEQ ID NO: 23.

2. The cell of claim 1, wherein the CAR further comprises a CD3 zeta signaling domain.

3. The cell of claim 2, wherein the CD3 zeta signaling domain comprises an amino acid sequence of SEQ ID NO: 19.

4. The cell of claim 2, wherein the CD3 zeta signaling domain is encoded by a nucleic acid sequence of SEQ ID NO: 7.

5. The cell of claim 1, wherein the CAR further comprises a transmembrane domain.

6. A cell comprising a chimeric antigen receptor (CAR), wherein the CAR comprises an α-folate receptor (FRα) antibody comprising the amino acid sequence of SEQ ID NO: 23.

7. The cell of claim 6, wherein the CAR further comprises a CD3 zeta signaling domain.

8. The cell of claim 7, wherein the CD3 zeta signaling domain comprises an amino acid sequence of SEQ ID NO: 19.

9. The cell of claim 7, wherein the CD3 zeta signaling domain is encoded by a nucleic acid sequence of SEQ ID NO: 7.

10. The cell of claim 6, wherein the CAR further comprises a transmembrane domain.

11. The cell of claim 6, wherein the CAR further comprises a 4-1BB costimulatory domain.

12. The cell of claim 11, wherein the 4-1BB costimulatory domain comprises an amino acid sequence of SEQ ID NO: 18.

13. The cell of claim 11, wherein the 4-1BB costimulatory domain is encoded by the nucleic acid sequence of SEQ ID NO: 6.

14. The cell of claim 1, wherein the CAR further comprises a 4-1BB costimulatory domain.

15. The cell of claim 14, wherein the 4-1BB costimulatory domain comprises an amino acid sequence of SEQ ID NO: 18.

16. The cell of claim 14, wherein the 4-1BB costimulatory domain is encoded by the nucleic acid sequence of SEQ ID NO: 6.

17. The cell of claim 1, wherein the cell is a mammalian cell.

18. The cell of claim 6, wherein the cell is a mammalian cell.

19. The cell of claim 1, wherein the cell is an immune cell.

20. The cell of claim 6, wherein the cell is an immune cell.

21. The cell of claim 19, wherein the immune cell is a T cell.

22. The cell of claim 20, wherein the immune cell is a T cell.

* * * * *